(12) United States Patent
Sarabu

(10) Patent No.: US 8,178,689 B2
(45) Date of Patent: May 15, 2012

(54) TRICYCLIC COMPOUNDS

(75) Inventor: Ramakanth Sarabu, Towaco, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 13/156,394

(22) Filed: Jun. 9, 2011

(65) Prior Publication Data

US 2011/0313002 A1 Dec. 22, 2011

Related U.S. Application Data

(60) Provisional application No. 61/355,619, filed on Jun. 17, 2010.

(51) Int. Cl.
*C07D 277/44* (2006.01)
*C07D 487/02* (2006.01)
*C07D 213/00* (2006.01)
*A61K 31/44* (2006.01)
*A61K 31/427* (2006.01)
*A61K 31/4155* (2006.01)

(52) U.S. Cl. .................. 548/195; 548/364.4; 546/267.7; 514/338; 514/371; 514/407

(58) Field of Classification Search .................. None
See application file for complete search history.

(56) References Cited

FOREIGN PATENT DOCUMENTS

| WO | 02/48106 | 6/2002 |
|---|---|---|
| WO | 2007/143434 | 12/2007 |
| WO | 2009/127546 | 10/2009 |

OTHER PUBLICATIONS

"PCT International Search Report dated Jul. 22, 2011".
Sarabu et al., "Expert Opinion on Therapeutic Patents" 18:759-768 (2008).

*Primary Examiner* — Kamal Saeed
*Assistant Examiner* — Nyeemah A Grazier
(74) *Attorney, Agent, or Firm* — George W. Johnston; Patricia S. Rocha-Tramaloni; Gene J. Yao

(57) ABSTRACT

The present invention provides novel compounds of formula I,

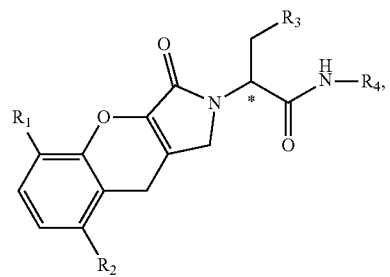

wherein the substituents are as those disclosed in the specification. These compounds, and the pharmaceutical compositions containing them, are useful for the treatment of metabolic diseases and disorders such as, for example, type II diabetes mellitus.

20 Claims, No Drawings

TRICYCLIC COMPOUNDS

PRIORITY TO RELATED APPLICATIONS

This application claims the benefit of U.S. Provisional Application No. 61/355,619, filed Jun. 17, 2010, which is hereby incorporated by reference in its entirety.

FIELD OF THE INVENTION

The present invention relates to organic compounds useful for therapy and/or prophylaxis in a mammal, and in particular to activators of glucokinase useful for treating metabolic diseases and disorders such as type II diabetes mellitus.

BACKGROUND OF THE INVENTION

Glucokinase (GK) is one of four hexokinases that are found in mammals. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10-15 mM) levels following a carbohydrate-containing meal. These findings contributed over a decade ago to the hypothesis that GK functions as a glucose sensor in β-cells and hepatocytes. In recent years, studies in transgenic animals have confirmed that GK does indeed play a critical role in whole-body glucose homeostasis. Animals that do not express GK die within days of birth with severe diabetes while animals overexpressing GK have improved glucose tolerance. An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans. Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin. While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

The present invention provides novel compounds according to formula I,

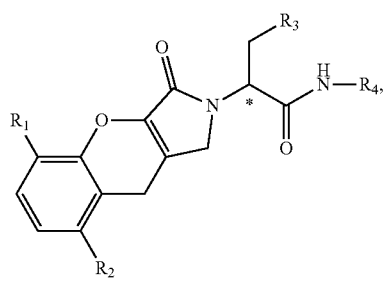

or a pharmaceutically acceptable salt thereof.
$R_1$, $R_2$, $R_3$, and $R_4$ are as defined herein.

The compounds of the present invention may be used, for example, in the treatment of a metabolic disease or disorder.

The present invention also provides a composition comprising a compound of formula I, or a pharmaceutically acceptable salt thereof, and a pharmaceutically acceptable carrier.

In addition, the present invention provides a method for activating glucokinase in a patient comprising administering, to said patient, an amount of a compound of formula I, or a pharmaceutically acceptable salt thereof, that is effective in activating glucokinase.

A further aspect of the present invention is a method for treating a metabolic disease or disorder in a patient comprising administering, to a patient in need thereof, a therapeutically effective amount of a compound of formula I, or a pharmaceutically acceptable salt thereof.

Yet another aspect of the present invention is a process for the preparation of a compound of formula I.

The present invention also relates to the use of a compound according to the present invention in the manufacture of a medicament for the treatment of a metabolic disease or disorder.

In another embodiment of the invention, the present invention relates to the use of a compound of the present invention for the treatment of a metabolic disease or disorder, for example, type II diabetes mellitus.

DETAILED DESCRIPTION OF THE INVENTION

Definitions

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, bornyl, adamantyl, indenyl and the like. In a preferred embodiment, the "cycloalkyl" moieties can optionally be substituted with one, two, three or four substituents with the understanding that said substituents are not, in turn, substituted further unless indicated otherwise in the Examples or claims below. Each substituent can independently be, for example, alkyl, alkoxy, halogen, amino, hydroxyl or oxygen (O=) unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate, with the understanding that said substituents are not, in turn, substituted further unless indicated otherwise in the Examples or claims below.

The term "lower alkyl", alone or in combination with other groups, refers to a branched or straight-chain alkyl radical of one to nine carbon atoms, preferably one to six carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "lower cycloalkyl", alone or in combination with other groups, refers to a cycloalkyl radical of three to ten, preferably three to six carbon atoms The term "aryl" refers to an aromatic mono- or polycarbocyclic radical of 6 to 12 carbon atoms having at least one aromatic ring. Examples of such groups include, but are not limited to, phenyl, napthyl. 1,2,3,4-tetrahydronaphthalene, 1,2-dihydronaphthalene, indanyl, 1H-indenyl and the like.

The alkyl, lower alkyl and aryl groups may be substituted or unsubstituted. When substituted, there will generally be, for example, 1 to 4 substituents present, with the understanding that said substituents are not, in turn, substituted further unless indicated otherwise in the Examples or claims below. These substituents may optionally form a ring with the alkyl, loweralkyl or aryl group they are connected with. Substituents may include, for example: carbon-containing groups such as alkyl, aryl, arylalkyl; halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, more preferably, for example, methoxy and ethoxy), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group.

The heteroaryl group described above may be substituted independently with one, two, or three substituents, with the understanding that said substituents are not, in turn, substituted further unless indicated otherwise in the Examples or claims below. These substituents may optionally form a ring with the heteroaryl group to which they are connected. Substituents may include, for example: carbon-containing groups such as alkyl, cycloalkyl, aryl, and arylalkyl; halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl); and —$CH_2$-heterocycloalkyl.

As used herein, the term "alkoxy" means alkyl-O—; and "alkoyl" means alkyl-CO—. Alkoxy substituent groups or alkoxy-containing substituent groups may be substituted by, for example, one or more alkyl groups with the understanding that said substituents are not, in turn, substituted further unless indicated otherwise in the Examples or claims below.

As used herein, the term "halogen" means a fluorine, chlorine, bromine or iodine radical, preferably a fluorine, chlorine or bromine radical, and more preferably a fluorine or chlorine radical.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

As used herein, the term "pharmaceutically acceptable carrier" indicates that the indicated carrier does not have properties that would cause a reasonably prudent medical practitioner to avoid administration thereof to a patient, taking into consideration the disease or conditions to be treated and the respective route of administration.

As used herein, the term "therapeutically effective" means an amount of drug, or combination or composition, which is effective for producing a desired therapeutic effect upon administration to a patient.

Compound

The present invention provides a compound according to formula I,

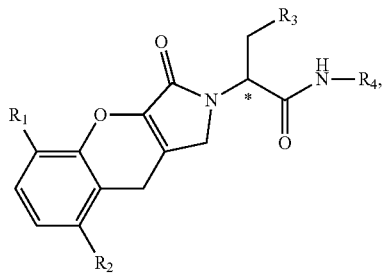

wherein:
$R_1$ and $R_2$ are each independently selected from the group consisting of H, Cl, Br, F and $OCH_3$;
$R_3$ is selected from the group consisting of lower alkyl, cycloalkyl, and heterocycloalkyl; and
$R_4$ is an unsubstituted or substituted heteroaryl connected by a ring carbon atom to the adjacent amine group, with at least one heteroatom being nitrogen which is adjacent to the connecting ring carbon atom, said substituted heteroaryl being substituted at a position other than adjacent to said connecting carbon atom independently with halogen, lower alkyl, ester, cyano, acid, cycloalkyl, aryl, —$CH_2$-aryl, heterocycloalkyl or —$CH_2$-heterocycloalkyl; or a pharmaceutically acceptable salt thereof.

The compounds of the present invention may be used, for example, in the treatment of a metabolic disease or disorder.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with chiral adsorbents or eluant). The invention embraces all of these forms.

In another embodiment, the invention relates to a compound according to formula I, or a pharmaceutically acceptable salt thereof, wherein $R_1$ and $R_2$ are each independently selected from the group consisting of H, Cl, and $OCH_3$.

In another embodiment, the invention relates to a compound according to formula I, or a pharmaceutically acceptable salt thereof, wherein $R_1$ is selected from the group consisting of H, Cl, and $OCH_3$.

In another embodiment, the invention relates to a compound according to formula I, or a pharmaceutically acceptable salt thereof, wherein $R_1$ is H.

In another embodiment, the invention relates to a compound according to formula I, or a pharmaceutically acceptable salt thereof, wherein $R_1$ is Cl.

In another embodiment, the invention relates to a compound according to formula I, or a pharmaceutically acceptable salt thereof, wherein $R_1$ is $OCH_3$.

In another embodiment, the invention relates to a compound according to formula I, or a pharmaceutically acceptable salt thereof, wherein $R_2$ is selected from the group consisting of H, Cl, and $OCH_3$.

In another embodiment, the invention relates to a compound according to formula I, or a pharmaceutically acceptable salt thereof, wherein $R_2$ is H.

In another embodiment, the invention relates to a compound according to formula I, or a pharmaceutically acceptable salt thereof, wherein $R_2$ is Cl.

In another embodiment, the invention relates to a compound according to formula I, or a pharmaceutically acceptable salt thereof, wherein $R_2$ is $OCH_3$.

In another embodiment, the invention relates to a compound according to formula I, or a pharmaceutically acceptable salt thereof, wherein $R_3$ is lower alkyl or lower cycloalkyl.

In another embodiment, the invention relates to a compound according to formula I, or a pharmaceutically acceptable salt thereof, wherein $R_3$ is lower alkyl.

In another embodiment, the invention relates to a compound according to formula I, or a pharmaceutically acceptable salt thereof, wherein $R_3$ is 2-propyl.

In another embodiment, the invention relates to a compound according to formula I, or a pharmaceutically acceptable salt thereof, wherein $R_3$ is lower cycloalkyl.

In another embodiment, the invention relates to a compound according to formula I, or a pharmaceutically acceptable salt thereof, wherein $R_3$ is cyclohexyl or cyclopentyl.

In another embodiment, the invention relates to a compound according to formula I, or a pharmaceutically acceptable salt thereof, wherein $R_3$ is 2-propyl or cyclohexyl.

In another embodiment, the invention relates to a compound according to formula I, or a pharmaceutically acceptable salt thereof, wherein $R_3$ is cyclohexyl.

In another embodiment, the invention relates to a compound according to formula I, or a pharmaceutically acceptable salt thereof, wherein $R_3$ is cyclopentyl.

In another embodiment, the invention relates to a compound according to formula I, or a pharmaceutically acceptable salt thereof, wherein $R_4$ is an unsubstituted or substituted heteroaryl selected from the group consisting of pyridinyl, thioazolyl, and pyrrolyl, said substituted heteroaryl being substituted at a position other than adjacent to said connecting carbon atom independently with halogen, lower alkyl, ester, cyano, acid, cycloalkyl, aryl, —CH$_2$-aryl, heterocycloalkyl or —CH$_2$-heterocycloalkyl.

In another embodiment, the invention relates to a compound according to formula I, or a pharmaceutically acceptable salt thereof, wherein R$_4$ is an unsubstituted or substituted heteroaryl selected from the group consisting of pyridinyl, thioazolyl, and pyrazolyl, said substituted heteroaryl being substituted at a position other than adjacent to said connecting carbon atom independently with halogen, ester, or lower alkyl.

In another embodiment, the invention relates to a compound according to formula I, or a pharmaceutically acceptable salt thereof, wherein R$_4$ is an unsubstituted or substituted heteroaryl which is pyridinyl or thioazolyl, said substituted heteroaryl being substituted at a position other than adjacent to said connecting carbon atom independently with chloro or methyl ester.

In another embodiment, the invention relates to a compound according to formula I, or a pharmaceutically acceptable salt thereof, wherein R$_4$ is pyrazolyl substituted at a position other than adjacent to said connection carbon atom with lower alkyl, said lower alkyl being substituted once or twice by hydroxyl.

In another embodiment, the invention relates to a compound according to formula I, or a pharmaceutically acceptable salt thereof, wherein:
R$_1$ and R$_2$ are each independently selected from the group consisting of H, Cl, and OCH$_3$;
R$_3$ is lower alkyl or lower cycloalkyl; and
R$_4$ is an unsubstituted or substituted heteroaryl connected by a ring carbon atom to the adjacent amine group, with at least one heteroatom being nitrogen which is adjacent to the connecting ring carbon atom, said substituted heteroaryl being substituted at a position other than adjacent to said connecting carbon atom independently with halogen, lower alkyl, ester, cyano, acid, cycloalkyl, aryl, —CH$_2$-aryl, heterocycloalkyl or —CH$_2$-heterocycloalkyl.

In another embodiment, the invention relates to a compound according to formula I, or a pharmaceutically acceptable salt thereof, wherein:
R$_1$ and R$_2$ are each independently selected from the group consisting of H, Cl, and OCH$_3$;
R$_3$ is selected from the group consisting of: 2-propyl, cyclohexyl, and cyclopentyl; and
R$_4$ is an unsubstituted or substituted heteroaryl selected from the group consisting of pyridinyl, thioazolyl, and pyrazolyl, said substituted heteroaryl being substituted at a position other than adjacent to said connecting carbon atom independently with halogen, ester, or lower alkyl.

In another embodiment, the invention relates to a compound according to formula I, or a pharmaceutically acceptable salt thereof, wherein:
R$_1$ and R$_2$ are each independently H or OCH$_3$;
R$_3$ is 2-propyl or lower cycloalkyl; and
R$_4$ is an unsubstituted or substituted pyrazine or pyrazolyl.

In another embodiment, the compound according to formula I is selected from the group consisting of:
(S)-2-(8-Chloro-3-oxo-3,9-dihydro-1H-chromeno[2,3-c]pyrrol-2-yl)-3-cyclohexyl-N-pyridin-2-yl-propionamide;
(S)-2-(8-Chloro-3-oxo-3,9-dihydro-1H-chromeno[2,3-c]pyrrol-2-yl)-3-cyclohexyl-N-thiazol-2-yl-propionamide;
(S)-2-(8-Chloro-3-oxo-3,9-dihydro-1H-chromeno[2,3-c]pyrrol-2-yl)-4-methyl-pentanoic acid pyridin-2-ylamide;
(S)-2-(8-Chloro-3-oxo-3,9-dihydro-1H-chromeno[2,3-c]pyrrol-2-yl)-4-methyl-pentanoic acid (5-chloro-pyridin-2-yl)-amide;
(S)-2-(8-Chloro-3-oxo-3,9-dihydro-1H-chromeno[2,3-c]pyrrol-2-yl)-4-methyl-pentanoic acid thiazol-2-ylamide;
6-[(S)-2-(8-Chloro-3-oxo-3,9-dihydro-1H-chromeno[2,3-c]pyrrol-2-yl)-4-methyl-pentanoylamino]-nicotinic acid methyl ester;
(S)-3-Cyclohexyl-2-(8-methoxy-3-oxo-3,9-dihydro-1H-chromeno[2,3-c]pyrrol-2-yl)-N-pyridin-2-yl-propionamide;
(S)—N-(5-Chloro-pyridin-2-yl)-3-cyclohexyl-2-(8-methoxy-3-oxo-3,9-dihydro-1H-chromeno[2,3-c]pyrrol-2-yl)-propionamide;
(S)-3-Cyclohexyl-2-(8-methoxy-3-oxo-3,9-dihydro-1H-chromeno[2,3-c]pyrrol-2-yl)-N-thiazol-2-yl-propionamide;
6-[(S)-3-Cyclohexyl-2-(8-methoxy-3-oxo-3,9-dihydro-1H-chromeno[2,3-c]pyrrol-2-yl)-propionylamino]-nicotinic acid methyl ester;
(S)-2-(8-Methoxy-3-oxo-3,9-dihydro-1H-chromeno[2,3-c]pyrrol-2-yl)-4-methyl-pentanoic acid thiazol-2-ylamide;
6-[(S)-2-(8-Methoxy-3-oxo-3,9-dihydro-1H-chromeno[2,3-c]pyrrol-2-yl)-4-methyl-pentanoylamino]-nicotinic acid methyl ester;
(S)-3-Cyclohexyl-2-(5,8-dimethoxy-3-oxo-3,9-dihydro-1H-chromeno[2,3-c]pyrrol-2-yl)-N-pyridin-2-yl-propionamide;
(S)—N-(5-Chloro-pyridin-2-yl)-3-cyclohexyl-2-(5,8-dimethoxy-3-oxo-3,9-dihydro-1H-chromeno[2,3-c]pyrrol-2-yl)-propionamide;
(S)-3-Cyclohexyl-2-(5,8-dimethoxy-3-oxo-3,9-dihydro-1H-chromeno[2,3-c]pyrrol-2-yl)-N-thiazol-2-yl-propionamide;
6-[(S)-3-Cyclohexyl-2-(5,8-dimethoxy-3-oxo-3,9-dihydro-1H-chromeno[2,3-c]pyrrol-2-yl)-propionylamino]-nicotinic acid methyl ester;
(S)-2-(5,8-Dimethoxy-3-oxo-3,9-dihydro-1H-chromeno[2,3-c]pyrrol-2-yl)-4-methyl-pentanoic acid (5-chloro-pyridin-2-yl)-amide;
(S)-2-(5,8-Dimethoxy-3-oxo-3,9-dihydro-1H-chromeno[2,3-c]pyrrol-2-yl)-4-methyl-pentanoic acid pyridin-2-ylamide;
6-[(S)-2-(5,8-Dimethoxy-3-oxo-3,9-dihydro-1H-chromeno[2,3-c]pyrrol-2-yl)-4-methyl-pentanoylamino]-nicotinic acid methyl ester;
(S)-2-(5-Chloro-3-oxo-3,9-dihydro-1H-chromeno[2,3-c]pyrrol-2-yl)-3-cyclohexyl-N-pyridin-2-yl-propionamide;
(S)-2-(5-Chloro-3-oxo-3,9-dihydro-1H-chromeno[2,3-c]pyrrol-2-yl)-3-cyclohexyl-N-thiazol-2-yl-propionamide;
6-[(S)-2-(5-Chloro-3-oxo-3,9-dihydro-1H-chromeno[2,3-c]pyrrol-2-yl)-4-methyl-pentanoylamino]-nicotinic acid methyl ester;
(S)-2-(5-Chloro-3-oxo-3,9-dihydro-1H-chromeno[2,3-c]pyrrol-2-yl)-4-methyl-pentanoic acid pyridin-2-ylamide;
(S)-2-(5-Chloro-3-oxo-3,9-dihydro-1H-chromeno[2,3-c]pyrrol-2-yl)-4-methyl-pentanoic acid thiazol-2-ylamide;
(S)-3-Cyclohexyl-N-[1-((R)-2,3-dihydroxy-propyl)-1H-pyrazol-3-yl]-2-(8-methoxy-3-oxo-3,9-dihydro-1H-chromeno[2,3-c]pyrrol-2-yl)-propionamide; and
(S)-3-Cyclopentyl-N-[1-(2-hydroxy-2-methyl-propyl)-1H-pyrazol-3-yl]-2-(3-oxo-3,9-dihydro-1H-chromeno[2,3-c]pyrrol-2-yl)-propionamide.

It will be appreciated, that the compounds of formula I in this invention may be derivatized at functional groups to provide derivatives which are capable of conversion back to the parent compound in vivo. Physiologically acceptable and metabolically labile derivatives, which are capable of producing the parent compounds of formula I in vivo are also within the scope of this invention.

Compositions and Methods

The present invention also relates to a composition comprising a compound as described above, or a pharmaceutically acceptable salt thereof, and a pharmaceutically acceptable carrier.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient. The composition can also be in the form of an oil emulsion or dispersion in conjunction with a lipophilic salt such as pamoic acid, or in the form of a biodegradable sustained-release composition for subcutaneous or intramuscular administration.

The present invention further relates to a method for activating glucokinase in a patient comprising administering, to said patient, an amount of a compound as described above that is effective in activating glucokinase.

The present invention further relates to a method for treating a metabolic disease or disorder in a patient comprising administering, to a patient in need thereof, a therapeutically effective amount of a compound as described above, or a pharmaceutically acceptable salt thereof. In a particular embodiment, the disorder or disease is type II diabetes mellitus.

In the practice of the method of the present invention, a therapeutically effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum.

The therapeutically effective amount of a compound of the present invention depends on a number of factors, such as, for example, the manner of administration, the age and the body weight of the subject, and the condition of the subject to be treated, and ultimately will be decided by the attending physician or veterinarian. For example, the dose of a compound of the present invention is typically in the range of about 1 to about 1000 mg per day. Preferably, the therapeutically effective amount is in an amount of from about 1 mg to about 500 mg per day.

The present invention also relates to the use of a compound according to the present invention in the manufacture of a medicament for the treatment of a metabolic disease or disorder, for example, type II diabetes mellitus.

In another embodiment of the invention, the present invention relates to the use of a compound according to the present invention for the treatment of a metabolic disease or disorder, for example, type II diabetes mellitus.

Synthesis

The present invention relates also to a process for the preparation of a compound according to the present invention.

Compounds of the present invention can be prepared beginning with commercially available starting materials and utilizing general synthetic techniques and procedures known to those skilled in the art. Outlined below are reaction schemes suitable for the preparation of such compounds. Chemicals may be purchased from companies such as for example Aldrich, Argonaut Technologies, VWR and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Multigram II Mettler Toledo Instrument Newark, Del. Biotage, ISCO and Analogix columns are pre-packed silica gel columns used in standard chromatography.

Preferably, the compounds of formula I can be prepared by the following general reaction Scheme I.

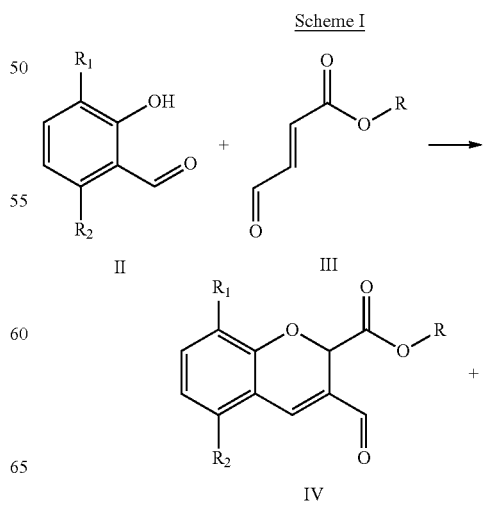

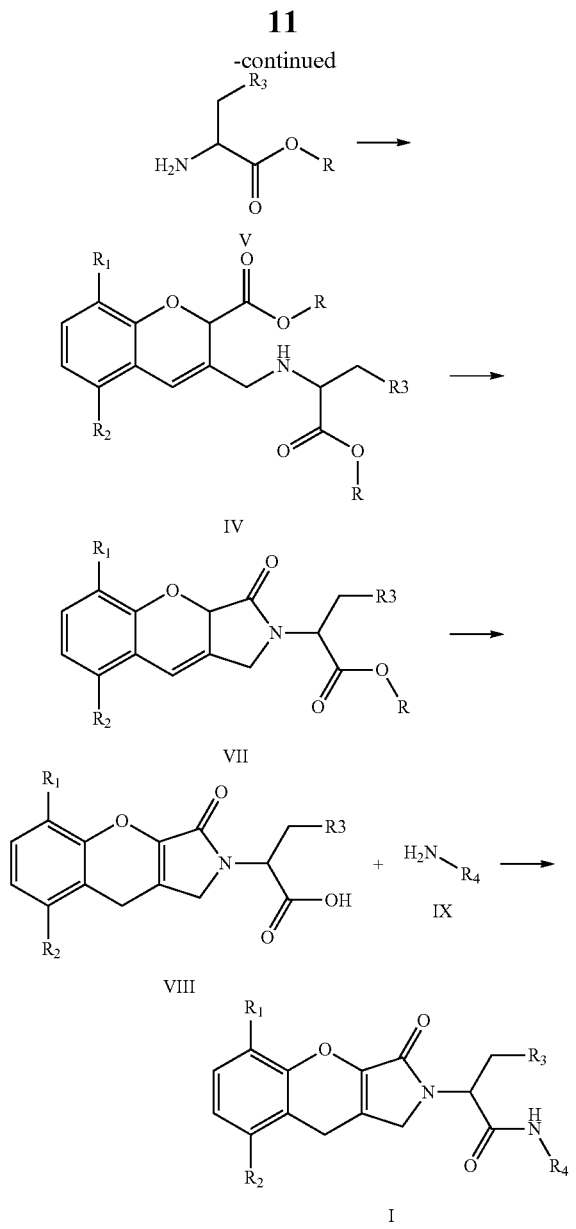

An embodiment of the present invention is a process for the preparation of a compound of the present invention comprising the steps of:

(A) reacting a compound of formula II with a compound of formula III to produce a compound of formula IV;
(B) reacting said compound of formula IV with a compound of formula V to produce a compound of formula VI;
(C) heating said compound of formula VI in presence of a base to produce a compound of formula VII;
(D) hydrolyzing said compound of formula VII to yield a compound of formula VIII; and
(E) reacting a compound of formula VIII with a compound of formula IX to produce a compound of formula I.

Another embodiment of the present invention provides a process for the preparation of a compound of the present invention comprising the step of reacting a compound of formula VIII with a compound of formula IX to produce a compound of formula I.

Compounds of formula II, wherein $R_1=R_2=H$; $R_1=H$, $R_2=Cl$; $R_1=Cl$, $R_2=H$; $R_1=Br$, $R_2=H$; $R_1=H$, $R_2=Br$; $R_1=H$, $R_2=F$; $R_1=F$, $R_2=H$; $R_1=OCH_3$, $R_2=H$; $R_1=H$, $R_2=OCH_3$; $R_1=R_2=OCH_3$; $R_1=R_2=Cl$; $R_1=R_2=F$; $R_1=OCH_3$, $R_2=Br$; $R_1=F$, $R_2=OCH_3$; $R_1=Br$, $R_2=Cl$; are commercially available. Compounds of formula II, where $R_1=Br$, $R_2=Br$; $R_1=Cl$, $R_2=OCH_3$; $R_1=Br$, $R_2=OCH_3$; $R_1=OCH_3$, $R_2=Cl$; $R_1=OCH_3$, $R_2=F$; $R_1=Cl$, $R_2=Br$; $R_1=Br$, $R_2=F$; $R_1=F$, $R_2=Br$; $R_1=F$, $R_2=Cl$; $R_1=Cl$, $R_2=F$, can be prepared from the corresponding commercially available phenols, via the sequence of reactions described in the general Scheme 2.

Scheme 2

MgCl$_2$, Et$_3$N, paraformaldehyde,
CH$_3$CN, reflux

1. K$_2$CO$_3$, H$_3$COCH$_2$Cl, H$_3$CCOCH$_3$
2. nBuLI, THF, -78° C. to RT then DMF, -78° C. to RT
3. Conc. HCl, CH$_3$OH, reflux The phenols can be converted to the compounds of formula II via either the MgCl$_2$ method or via the ortho-metallation method as shown in scheme 2, as described in PCT Int. Appl. WO 2008121602.

The compound of formula II may be reacted with commercially available (E)-4-oxo-but-2-enoic acid ethyl ester (the compound of formula III) in presence of catalytic amounts of pyrrolidine and 2-nitrobenzoic acid at room temperature to yield the corresponding 3-formyl-chromene-2-carboxylic acid ethyl ester derivatives (compound of formula IV).

A compound of formula V can then be condensed with a compound of formula IV under reductive amination conditions to yield a compound of formula VI.

The compounds of formula V wherein R is H are amino acids, a number of which are available from commercial sources. Several natural and unnatural amino acids are commercially available or readily available via several methods reported in the literature (under similar conditions to those described in D. J. Ager, in *Handbook of chiral chemicals, 2$^{nd}$* Edition, p 11-30, CRC Press). Among these methods are asymmetric hydrogenation of the corresponding enamides (under similar conditions to those described in Ager, D. J., Laneman, S. A., *The Synthesis of Unnatural Amino Acids, in Asymmetic Catalysis on Industrial Scale*, Blaser, H.-U., Schmidt, E., Wiley-VCH: Weinheim, 2004, p 23), chiral auxiliary derived asymmetric induction methods (under similar conditions to those described in *Pure and App. Chem.* 1983, 55, 1799; *Tetrahedron,* 1988, 44, 5541; *J. Amer. Chem. Soc.,* 1990, 112, 4011), asymmetric methods using chiral phase transfer catalyzed alkylations (under similar conditions to those described in *Acc. Chem. Research* 2004, 37, 506), condensation of the corresponding aldehydes with glycine, protected glycine or protected glycine phosphonate derivatives followed by hydrogenation (under similar conditions to those described in *J. Org. Chem.* 1989, 54, 4511; *Org. Lett.* 2005, 7, 5433; *J. Org. Chem.* 2005, 70, 5840), alkylating 2-(acetylamino)-propanedioic acid diesters with appropriate alkylating reagents followed by either enzymatic resolution or decarboxylation (under similar conditions to those described in Chemistry & Biology, 2006, 13, 607; Acc. Chem. Research 2004, 37, 506 and references cited therein), and alkylating (benzhydrylidene-amino)-acetic acid alkyl esters with halides, triflate, tosylate or mesylate derivatives and converting the resulting benzhydrylidene derivatives to amino acids using standard procedures (under similar conditions to those described in J. Med. Chem.; 2006 49, 6074). The halides, triflates, tosylates or mesylates can be prepared from the corresponding alcohols using any conditions known for converting an alcohol to a halide, triflate, tosylate or mesylate. Aldehydes may be prepared by oxidizing the corresponding alcohols using standard conditions, or by reducing the corresponding acids, esters, or Weinreb amides using standard conditions. Alcohols may be purchased or prepared from the corresponding acids, esters, or aldehydes using any conditions known for preparing an alcohol. Using these methods, compounds of formula V, where $R_3$ is alkyl, cycloalkyl, heterocycloalkyl, aryl or heteroaryl groups can be prepared.

The alkyl and cycloalkyl amino acids such as, cyclopentyl alanine, cyclohexyl alanine, and cyclobutyl alanine are either commercially available or are readily available from corresponding halides or tosylates or mesylates via the general methods described above. Similarly, aryl and heteroaryl containing amino acids are either commercially available or can be prepared from readily accessible aryl or heteroaryl methyl halides, using the standard methods described before. Amino acids such as, 2,6-difluorophenyl alanine, 2-thienyl alanine, 2-amino-3-isoxazol-5-yl-propionic acid can be prepared. Several fluoro- and chloro-substituted leucines, for example, 2-amino-4-fluoro-4-methyl-pentanoic acid, 2-amino-4-chloro-4-methyl-pentanoic acid, 2-amino-5,5,5-trifluoro-4-methyl-pentanoic acid, 2-amino-4,4-difluoro-butyric acid and 2-amino-4,4-dichloro-butyric acid are readily accessible from known methods described in the literature (under similar conditions to those described in Bioorg. & Med. Chem. Lett., 2008, 923; Synthesis 1996, 12, 1419). Alternatively fluorinated compounds can be prepared from the corresponding alcohols, aldehydes or ketones by treatment with fluorinated agents such as diethylaminosulfurtrifluoride (under similar conditions to those described in Organic Syn. 1977, 57, 50; Chimia, 1985, 35, 134). For example 2-amino-4,4-difluoro-pentanoic acid can be prepared from the corresponding ketone, (S)-2-benzyloxycarbonylamino-4-oxo-pentanoic acid methyl ester (under similar conditions to those described in WO 2005040142) using diethylaminosulfurtrifluoride. 2-amino-4,4-difluoro-butyric acid may be prepared by alkylating a 2-(acetylamino)-propanedioic acid diester with trifluoro-methanesulfonic acid 2,2-difluoro-ethyl ester. Trifluoro-methanesulfonic acid 2,2-difluoro-ethyl ester can be prepared as described in the literature (under similar conditions to those described in WO 9964442). Hydroxy substituted leucine, 2-amino-4-hydroxy-4-methyl-pentanoic acid, can be prepared from appropriately substituted leucine, via its reaction with N-bromosuccinimide, as reported (under similar conditions to those described in Tetrahedron Lett., 1990, 31, 7059). Similarly, fluoro-substituted amino acids can be obtained via known methods (under similar conditions to those described in Tetrahedron, 2004, 60, 6711). If a gem-difluoro cycloalkyl is required, it can be obtained via the corresponding keto-derivative, using diethylaminosulfurtrifluoride (under similar conditions to those described in Organic Syn., 1977, 57, 50; Chimia, 1985, 35, 134). The vicinal difluorocyclopentane derivative 2-amino-3-((1R,3S,4R)-3,4-difluoro-cyclopentyl)-propionic acid methyl ester can be prepared by reacting the corresponding aldehyde with a protected glycine phosphonate derivative followed by hydrogenation (under similar conditions to those described in J. Org. Chem. 1989, 54, 4511; Org. Lett. 2005, 7, 5433; J. Org. Chem. 2005, 70, 5840). The aldehyde may be prepared from the corresponding alcohol using any known procedure for oxidizing an alcohol to an aldehyde such as a Swern oxidation. The corresponding alcohol, ((1R,3S,4R)-3,4-difluoro-cyclopentyl)-methanol, can be prepared under similar conditions to those described in WO2008111473.

Cycloalkanone containing amino acids, for example, cyclopentan-3-one, can be prepared using the appropriately protected cyclopentane-3-one methyl tosylate or mesylate (under similar conditions to those described in PCT Int. Appl. WO2003095438; PCT Int. Appl. WO2007115968) resulting in the preparation of protected amino acid, 2-amino-3-(8,8-dimethyl-6,10-dioxa-spiro[4.5]dec-2-yl)-propionic acid via the general methods of amino acid synthesis described above. Amino acid derivatives with a pyrrolidinone ring in the side chain such as 2-amino-3-(2-oxo-pyrrolidin-3-yl)-propionic acid can be prepared using literature reports (WO9957135). Heterocycloalkyl containing amino acid 2-amino-3-(tetrahydro-pyran-4-yl)-propionic acid is commercially available, while the corresponding analog 2-amino-3-(tetrahydro-pyran-2-yl)-propionic acid can be prepared using reported procedures (under similar conditions to those described in PCT Int. Appl. WO2001005783; PCT Int. Appl. WO2007070201). The amino acids with 2-tetrahydrofuran ring, 2-amino-3-(tetrahydro-furan-2-yl)-propionic acid can be prepared from the 2-furyl derivative via the hydrogenation of 2-furyl ring and subsequent diastereomer separation using standard methods (under similar conditions to those described in PCT Int. Appl. WO 2004033462; PCT Int. Appl. WO9214706).

Amino acids with bicyclic systems such as norbornyl rings can be prepared by reacting the corresponding aldehydes with a protected glycine phosphonate derivative followed by hydrogenation (under similar conditions to those described in J. Org. Chem. 1989, 54, 4511; Org. Lett. 2005, 7, 5433; J. Org. Chem. 2005, 70, 5840). The aldehydes may be prepared from the corresponding alcohols using any known procedure for oxidizing an alcohol to an aldehyde such as a Swern oxidation. The corresponding alcohols are either commercially available (such as 2-norborananemethanol) or can be prepared using literature methods (such as bicyclo[2.2.1]hept-7-yl-methanol, under similar conditions to those described in J. Med. Chem. 2005, 48, 8103).

Amino acid derivatives of formula V where $R_3$ is cycloalkyl substituted with a fluorine on the methine ring attachment carbon atom, such as 2-amino-3-(1-fluoro-cyclobutyl)-propionic acid, 2-amino-3-(1-fluoro-cyclopentyl)-propionic acid, or 2-amino-3-(1-fluoro-cyclohexyl)-propionic acid, can be prepared by alkylating (benzhydrylidene-amino)-acetic acid alkyl esters with triflate, tosylate or mesylate derivatives of the corresponding (1-fluoro-cycloalkyl)-methanol analogs or the corresponding bromides. The resulting benzhydrylidene derivatives can be converted to the amino acids using standard procedures (under similar conditions to those described in J. Med. Chem.; 2006 49, 6074). The triflate, tosylate or mesylate derivatives of the corresponding (1-fluoro-cycloalkyl)-methanol analogs can be prepared from the alcohols using any conditions known for converting an alcohol to a triflate, tosylate or mesylate. The bromide derivatives can be prepared from the alcohols using any conditions known for converting an alcohol to a bromide. The (1-fluoro-cycloalkyl)-methanol analogs are known in the literature (under similar conditions to those described in Synthesis 1988, 4, 310; PCT Int. Appl. WO 2006064286) or can be prepared from the corresponding epoxide (under similar conditions to those described in *Chem. Ber.* 1922, 55, 2725) by treatment with an appropriate fluorinating reagent, for example pyridine hydrofluoride (under similar conditions to those described in *J. Fluorine Chem.;* 1995; 74; 283). The corresponding epoxides can be prepared from the corresponding exocyclic alkenes directly or via the halohydrins using standard conditions (under similar conditions to those described in *J. Amer. Chem. Soc.* 1954, 76, 4373). The corresponding halohydrins can be prepared under similar conditions to those described in *J. Org. Chem.* 1971, 36, 2915. The related acyclic analog, 4-fluoro-leucine ethyl ester, can be prepared via literature procedures (under similar conditions to those described in *J. Org. Chem.* 2005, 70, 2372).

Amino acid derivatives of formula V where $R_3$ is alkyl or cycloalkyl substituted with a hydroxyl group on the methine ring attachment carbon atom, such as 2-amino-4-hydroxy-4-methyl-pentanoic acid, 2-amino-3-(1-hydroxy-cyclobutyl)-propionic acid, 2-amino-3-(1-hydroxy-cyclopentyl)-propionic acid, or 2-amino-3-(1-hydroxy-cyclohexyl)-propionic acid, can be prepared by alkylating (benzhydrylidene-amino)-acetic acid alkyl esters with triflate, tosylate or mesylate derivatives of the corresponding (1-hydroxy-cycloalkyl)-methanol analogs (1-hydroxymethyl-cyclohexane is commercially available, for 2-methyl-propane-1,2-diol see *J. Org. Chem.* 1989, 54, 4677; *J. Org. Chem.* 1989, 54, 3523; for 1-hydroxymethyl-cyclopentanol see *Tetrahedron Lett.* 1984, 25, 4245, for 1-hydroxymethyl-cyclobutanol see *J. Am. Chem. Soc.* 1949, 71, 3925; *J. Org. Chem.* 1993, 58, 3140), corresponding bromides (for 1-halo-2-methyl-propan-2-ol see *Organometal. Chem. Syn.* 1971, 1, 127; for 1-halomethyl-cyclopentanol see *Tetrahedron* 1959, 7, 165; *Bull. Chem. Soc. Jpn* 1982, 55, 1498; *J. Org. Chem.* 1984, 49, 4497; *Tetrahedron Lett.* 1986, 27, 3891; *Can. J. Chem.* 1988, 66, 168; *Green Chem.* 2005, 7, 100; for 1-halomethyl-cyclobutanol see *Tetrahedron* 1959, 7, 165; *J. Org. Chem.* 1971, 36, 2915; *J. Org. Chem.* 1973, 38, 1463, for 1-halomethyl-cyclohexanol see *J. Org. Chem.* 1980, 45, 924; *J. Org. Chem.* 1981, 46, 1283; *J. Org. Chem.* 1984, 49, 4497), or corresponding tertiary alcohol protected analogs (for 1-hydroxy-2-methyl-propan-2-ol see *J. Am. Chem. Soc.* 2000, 122, 8837; for 1-hydroxymethyl-cyclopentanol see PCT Inter. Appl. WO19960117; for 1-hydroxymethyl-cyclohexanol see *J. Org. Chem.* 1998, 63, 2422). The resulting benzhydrylidene derivatives can be converted to the amino acids using standard procedures (under similar conditions to those described in *J. Med. Chem.;* 2006 49, 6074). The triflate, tosylate or mesylate derivatives can be prepared from the alcohols using any conditions known for converting an alcohol to a triflate, tosylate or mesylate. The bromide derivatives can be prepared from the alcohols using any conditions known for converting an alcohol to a bromide. Alternatively these compounds can be prepared by condensing the corresponding aldehydes with glycine, protected glycine or protected glycine phosphonate derivatives followed by hydrogenation (under similar conditions to those described in *J. Org. Chem.* 1989, 54, 4511; *Org. Lett.* 2005, 7, 5433; *J. Org. Chem.* 2005, 70, 5840). The corresponding alcohol protected aldehydes are known in the literature (for protected 2-hydroxy-2-methyl-propionaldehyde see *J. Am. Chem. Soc.* 2000, 122, 8837; *Tetrahedron Lett.* 2005, 46, 6495; for protected 1-hydroxy-cyclopentanecarbaldehyde see *J. Chem. Soc., Perkin Trans.* 1 1988, 1119, for protected 1-hydroxy-cyclohexanecarbaldehyde see *Synlett* 1991, 479; *Tetrahedron* 1994, 50, 2821; *J. Org. Chem.* 1998, 63, 2422) or can be prepared from the alcohols using any method suitable for oxidizing a primary alcohol to an aldehyde. Unmasking of the alcohol functionality can be accomplished using any conditions known for converting a protected alcohol such as a silyl protected alcohol or an ester protected alcohol to an alcohol.

Amino acid derivatives of formula V where $R_3$ is a geminal dihaloalkyl group, such as 2-amino-4,4-difluoro-butyric acid, 2-amino-4,4-dichloro-butyric acid or 2-amino-4,4-difluoro-pentanoic acid, can be prepared as described in the literature (under similar conditions to those described in PCT Int. Appl. WO 2005040142; *Synthesis* 1996, 12, 1419).

Compounds of formula V in which R is a lower alkyl can be readily produced from the corresponding acids via an esterification reaction.

Following the formation of the compound of formula VI, the compound of formula VI can be heated in presence of a base, for example a tertiary amine, in a solvent, for example acetonitrile, to yield a compound of formula VII. The compound of formula VII can then be hydrolyzed to yield the corresponding carboxylic acid of the formula VIII.

The carboxylic acid of the compounds of formula VIII and the amines of formula IX may be converted to the compounds of formula I through any conventional means to form an amide bond between a carboxylic acid and an amine (see for example, Montalbetti, C. A. G. N., Falque, V., *Tetrahedron*, 2005, 61, 10827-10852). If the compounds of formula I are a mixture of enantiomers or diastereomers, the appropriate chromatographic techniques, such as supercritical fluid chromatography, may be utilized to produce chirally pure or chirally enriched compounds of formula I.

Compounds of formula IX may include unsubstituted or substituted heteroaryl or heterocycloalkyl groups which are commercially available or known in the literature. More preferred heteroaryl groups include 2H-[1,2,3]triazol-4-yl, 2H-[1,2,4]triazol-3-yl, pyrimidin-4-yl, furazan-3-yl, pyridazin-3-yl, thiazol-4-yl, dihydro-1H-[1,2,4]triazol-3-yl, 1H-imidazol-2-yl, 1H-benzoimidazol-2-yl, [1,2,5]thiadiazol-3-yl, oxazol-2-yl, benzooxazol-2-yl, 4,5-dihydro-oxazol-2-yl, pyrimidin-2-yl, [1,2,4]oxadiazol-5-yl, isoxazol-3-yl, [1,2,4]triazin-3-yl, [1,2,4]triazolo[1,5-a]pyridin-2-yl, isoquinolin-3-yl, and quinolin-2-yl. Most preferred heteroaryl groups include 1H-pyrazol-3-yl, pyrazin-2-yl, pyridin-2-yl, thiazol-2-yl, [1,3,4]thiadiazol-2-yl, and [1,2,4]thiadiazol-5-yl.

Compounds of formula IX, wherein $R_4$ is 1,5-dimethyl-1H-pyrazol-3-yl or 5-methyl-1H-pyrazol-3-yl, are commercially available.

The compound of formula IX, wherein $R_4$ is 1-t-butoxycarbonyl-5-methyl-1H-pyrazol-3-yl, can be prepared as described in PCT Int. Appl., 2005121110.

Compounds of formula IX, wherein $R_4$ is 1-(2-t-butoxycarbonylamino-ethyl)-1H-pyrazol-3-yl, 1-(2-isopropoxy-ethyl)-1H-pyrazol-3-yl, 1-(2-methoxy-2-methyl-propyl)-1H-pyrazol-3-yl, 1-(2-hydroxy-2-methyl-propyl)-1H-pyrazol-3-yl, 1-(2-hydroxy-propyl)-1H-pyrazol-3-yl, 1-(2-methyl-2-triethylsilanyloxy-propyl)-1H-pyrazol-3-yl, 1-(1-hydroxy-cyclopropylmethyl)-1H-pyrazol-3-yl, 1-(4-methoxycarbonyl-cyclohexylmethyl)-1H-pyrazol-3-yl, 1-2-(t-butyl-dimethyl-silanyloxy)-ethyl-1H-pyrazol-3-yl, 1-(3-carboxy-benzyl)-1H-pyrazol-3-yl, 1-1-(4-methoxycarbonyl-phenyl)-butyl-1H-pyrazol-3-yl, 1-(3-t-butoxycarbonylamino-benzyl)-1H-pyrazol-3-yl, 1-(3-methoxycarbonyl-benzyl)-1H-pyrazol-3-yl, 1-(4-t-butoxycarbonylamino-but-2-ynyl)-1H-pyrazol-3-yl, 1-(4-hydroxy-but-2-ynyl)-1H-pyrazol-3-yl, 1-(3-methyl-but-2-enyl)-1H-pyrazol-3-yl, 1-(3-hydroxy-3-methyl-butyl)-1H-pyrazol-3-yl, 1-(4-methoxycarbonyl-benzyl)-1H-pyrazol-3-yl, 1-(3-methyl-butyl)-1H-pyrazol-3-yl, 1-isobutyl-1H-pyrazol-3-yl, 1-octyl-1H-pyrazol-3-yl, 1-hexyl-1H-pyrazol- 3-yl, 1-(3-hydroxy-3-methyl-butyryl)-1H-pyrazol-3-yl, 1-((R)-2,3-dihydroxy-propyl)-1H-pyrazol-3-yl, 1-((S)-2,3-dihydroxy-propyl)-1H-pyrazol-3-yl, 1-ethanesulfonyl-1H-pyrazol-3-yl, 1-(4-methoxy-benzyl)-1H-pyrazol-3-yl, 1-(4-cyano-benzyl)-1H-pyrazol-3-yl, 1-(3-hydroxy-propyl)-1H-pyrazol-3-yl, 1-methanesulfonylmethyl-1H-pyrazol-3-yl, 1-(4-methanesulfonyl-benzyl)-1H-pyrazol-3-yl, 1-carbamoylmethyl-1H-pyrazol-3-yl, 1-(2-t-butoxycarbonyl-ethyl)-1H-pyrazol-3-yl, 1-t-butoxycarbonylmethyl-1H-pyrazol-3-yl, 1-propyl-1H-pyrazol-3-yl, 1-(4-chloro-benzyl)-1H-pyrazol-3-yl, 1-(2-methoxy-ethyl)-1H-pyrazol-3-yl, 1-cyclopropylmethyl-1H-pyrazol-3-yl, 1-(3,4-dichloro-benzyl)-1H-pyrazol-3-yl, 1-phenethyl-1H-pyrazol-3-yl, 1-t-butoxycarbonyl-1H-pyrazol-3-yl, 1-isopropyl-1H-pyrazol-3-yl, 1-(4-methyl-benzyl)-1H-pyrazol-3-yl, 1-(4-hydroxy-butyl)-1H-pyrazol-3-yl, 1-butyl-1H-pyrazol-3-yl, 1-ethyl-1H-pyrazol-3-yl, 1-benzyl-1H-pyrazol-3-yl, 1-methyl-1H-pyrazol-3-yl, or 1H-pyrazol-3-yl, are commercially available or can be prepared as described in U.S. Pat. Appl. US 2008021032.

Compounds of formula IX, wherein $R_4$ is 1-(dimethylphosphinoylmethyl)-1H-pyrazol-3-yl, 1-(diethoxy-phosphorylmethyl)-5-methyl-1H-pyrazol-3-yl, 1-(diethoxy-phosphorylmethyl)-1H-pyrazol-3-yl, or 1-(ethoxy-methyl-phosphinoylmethyl)-1H-pyrazol-3-yl, can be prepared as described in PCT Int. Appl. WO2008005964.

The compound of formula IX, wherein $R_4$ is 1-difluoromethyl-1H-pyrazol-3-yl, can be prepared as described in PCT Int. Appl. WO2005090332.

Compounds of formula IX, wherein $R_4$ is 5-cyano-pyrazin-2-yl, 5-methylsulfanyl-pyrazin-2-yl, 5-chloro-pyrazin-2-yl, pyrazin-2-yl, 5-methoxy-pyrazin-2-yl, 5-methyl-pyrazin-2-yl or 5-bromo-pyrazin-2-yl, are commercially available.

Compounds of formula IX, wherein $R_4$ is 5-(diethoxy-phosphorylmethyl)-pyrazin-2-yl, 5-(diisopropoxy-phosphorylmethyl)-pyrazin-2-yl or 5-(ethoxy-methyl-phosphinoylmethyl)-pyrazin-2-yl, can be prepared as described in PCT Int. Appl. WO2008005964.

Compounds of formula IX, wherein $R_4$ is 5-methoxycarbonyl-pyrazin-2-yl, 5-dimethylamino-pyrazin-2-yl, 5-thiophen-2-yl-pyrazin-2-yl, 5-(3-methoxy-phenyl)-pyrazin-2-yl, 5-(2-hydroxy-phenyl)-pyrazin-2-yl, 5-(2-methoxy-phenyl)-pyrazin-2-yl, 5-vinyl-pyrazin-2-yl, 5-methanesulfonylamino-pyrazin-2-yl, 5-dimethoxymethyl-pyrazin-2-yl, 5-{1-[(E)-t-butoxyimino]-ethyl}-pyrazin-2-yl, 5-t-butoxycarbonyl-pyrazin-2-yl, 5-methylsulfanylmethyl-pyrazin-2-yl, 5-cyanomethyl-pyrazin-2-yl, 5-(1,1-dimethoxy-ethyl)-pyrazin-2-yl, 5-(bis-ethoxycarbonyl-methyl)-pyrazin-2-yl, 5-[1,3]dioxolan-2-yl-pyrazin-2-yl, 5-[1,3]dioxolan-2-ylmethyl-pyrazin-2-yl, 5-(2-methoxy-ethoxy)-pyrazin-2-yl, 5-allyloxy-pyrazin-2-yl, 5-(2,2-dimethoxyethyl)-pyrazin-2-yl, 5-(2,2-dimethyl-[1,3]dioxolan-4-yl)-pyrazin-2-yl, 5-(2-benzyloxy-1-benzyloxymethyl-ethoxycarbonyl)-pyrazin-2-yl, 5-[2-(tetrahydro-pyran-2-yloxy)-ethoxy]-pyrazin-2-yl, 5-(2-methyl-propenyl)-pyrazin-2-yl, 5-(4-methyl-2,5-dioxo-imidazolidin-4-yl)-pyrazin-2-yl, 5-(tetrahydro-furan-2-yl)-pyrazin-2-yl, 5-(2-methoxy-ethylamino)-pyrazin-2-yl, 5-(2-triethylsilanyloxy-ethylamino)-pyrazin-2-yl, 5-(1H-indol-5-yl)-pyrazin-2-yl, 5-(5,6-dihydro-4H-pyran-2-yl)-pyrazin-2-yl, 5-thiophen-3-yl-pyrazin-2-yl, 5-furan-3-yl-pyrazin-2-yl, 5-(5-cyano-thiophen-2-yl)-pyrazin-2-yl, 5-(4,5-dihydro-1H-imidazol-2-yl)-pyrazin-2-yl, or 5-allyl-pyrazin-2-yl, can be prepared as described in PCT Int. Appl. WO2004052869.

Compounds of formula IX, wherein $R_4$ is 5-cyclopropyl-pyrazin-2-yl, 5-t-butoxycarbonylamino-pyrazin-2-yl, 5-(t-butoxycarbonyl-methyl-amino)-pyrazin-2-yl, 5-(2-oxo-pyrolidin-1-yl)-pyrazin-2-yl, 5-[2-(t-butyl-dimethyl-silanyloxy)-ethoxy]-pyrazin-2-yl, 5-isopropoxy-pyrazin-2-yl, or 5-(4-acetyl-3-methyl-piperazin-1-ylmethyl)-pyrazin-2-yl, can be prepared as described in PCT Int. Appl. WO2007007886.

Compounds of formula IX, wherein $R_4$ is 4-(4-isopropyl-phenyl)-thiazol-2-yl, 4,5,6,7-tetrahydro-benzothiazol-2-yl, 4,5-dimethyl-thiazol-2-yl, 4,5-dimethyl-thiazol-2-yl, 4-acetyl-thiazol-2-yl, 4-carbamoyl-thiazol-2-yl, 4-carboxymethyl-thiazol-2-yl, 4-chloromethyl-thiazol-2-yl, 4-cyano-thiazol-2-yl, 4-ethoxycarbonyl-4,5,6,7-tetrahydro-benzothiazol-2-yl, 4-ethoxycarbonylmethyl-5-ethyl-thiazol-2-yl, 4-ethoxycarbonylmethyl-5-methyl-thiazol-2-yl, 4-ethoxycarbonylmethyl-thiazol-2-yl, 4-ethoxycarbonyl-thiazol-2-yl, 4-ethoxyoxalyl-thiazol-2-yl, 4-formyl-thiazol-2-yl, 4-hydroxymethyl-thiazol-2-yl, 4-isopropyl-thiazol-2-yl, 4-methoxycarbonylmethyl-thiazol-2-yl, 4-methoxycarbonyl-thiazol-2-yl, 4-methyl-thiazol-2-yl, 4-t-butyl-thiazol-2-yl, 4-trifluoromethyl-thiazol-2-yl, 5-(2-hydroxy-ethylcarbamoyl)-4-methyl-thiazol-2-yl, 5-acetyl-4-methyl-thiazol-2-yl, 5-bromo-thiazol-2-yl, 5-bromo-thiazol-2-yl, 5-bromo-thiazol-2-yl, 5-chloro-thiazol-2-yl, 5-chloro-thiazol-2-yl, 5-chloro-thiazolo[5,4-b]pyridin-2-yl, 5-ethoxycarbonyl-4-methyl-thiazol-2-yl, 5-ethoxycarbonylmethylsulfanyl-thiazol-2-yl, 5-ethoxycarbonyl-thiazol-2-yl, 5-fluoro-thiazol-2-yl, 5-fluoro-thiazol-2-yl, 5-formyl-thiazol-2-yl, 5-hydroxymethyl-thiazol-2-yl, 5-isopropyl-4-methoxycarbonyl-thiazol-2-yl, 5-methanesulfonyl-thiazol-2-yl, 5-methoxycarbonylmethyl-thiazol-2-yl, 5-methoxycarbonyl-thiazol-2-yl, 5-methoxy-thiazol-2-yl, 5-methoxy-thiazolo[5,4-b]pyridin-2-yl, 5-methyl-4,5,6,7-tetrahydro-thiazolo[5,4-c]pyridin-2-yl, 5-methyl-thiazol-2-yl, 5-nitro-thiazol-2-yl, 5-thiocyanato-thiazol-2-yl, 6,7-dihydro-4H-pyrano[4,3-d]thiazol-2-yl, 6-bromo-thiazolo[4,5-b]pyrazin-2-yl, 6-carboxymethyl-benzothiazol-2-yl, 6-fluoro-benzothiazol-2-yl, 6-methanesulfonyl-benzothiazol-2-yl, 6-nitro-benzothiazol-2-yl, benzothiazol-2-yl, thiazol-2-yl, thiazolo[5,4-b]pyridin-2-yl, 4-chloromethyl-thiazol-2-yl, or 4,5,6,7-tetrahydro-benzothiazol-2-yl, are commercially available.

Compounds of formula IX, wherein $R_4$ is 5-(3-cyano-phenoxy)-thiazol-2-yl, 5-(3-methoxycarbonyl-phenoxy)-thiazol-2-yl, 5-(4-methoxycarbonyl-phenoxy)-thiazol-2-yl, 5-(5-methoxycarbonyl-pyridin-3-yloxy)-thiazol-2-yl, 5-(6-fluoro-pyridin-3-yloxy)-thiazol-2-yl, or 5-(3,4-bis-methoxycarbonyl-phenoxy)-thiazol-2-yl, can be prepared as described in PCT Int. Appl. WO 2008005914.

Compounds of formula IX, wherein $R_4$ is 4-(diethoxy-phosphorylmethyl)-5-isopropyl-thiazol-2-yl, 4-(diisopropoxy-phosphorylmethyl)-thiazol-2-yl, 4-(dimethyl-phosphinoyloxymethyl)-thiazol-2-yl, 4-(ethoxy-methyl-phosphinoylmethyl)-thiazol-2-yl, 4-(ethoxy-methyl-phosphinoyloxymethyl)-thiazol-2-yl, 4-[2-(diethoxy-phosphoryl)-1-hydroxy-ethyl]-thiazol-2-yl, 4-[2-(diethoxy-phosphoryl)-ethyl]-thiazol-2-yl, 5-(diethoxy-phosphoryl)-thiazol-2-yl, 5-(diethoxy-phosphorylmethyl)-thiazol-2-yl, 4-(2-oxido-[1,3,2]dioxaphosphinan-2-ylmethyl)-thiazol-2-yl, 4-((S)-ethoxy-methyl-phosphinoylmethyl)-thiazol-2-yl, 4-(diethoxy-phosphorylmethyl)-thiazol-2-yl, 4-(diethoxy-phosphoryl)-thiazol-2-yl or 4-bromo-thiazol-2-yl, can be prepared as described in PCT Int. Appl. WO 2008005964.

Compounds of formula IX, wherein $R_4$ is 4-(2-ethoxycarbonyl-ethylsulfanylmethyl)-thiazol-2-yl, 4-carboxymethylsulfanylmethyl-thiazol-2-yl, or 5-(2-ethoxycarbonyl-ethylsulfanyl)-thiazol-2-yl, can be prepared as described in PCT Int. Appl. WO 2007125103.

The compound of formula IX, wherein $R_4$ is 4-methoxy-6-methoxycarbonyl-benzothiazol-2-yl, can be prepared as described in PCT Int. Appl. WO 2007122482.

The compound of formula IX, wherein $R_4$ is 4-(1-acetyl-piperidin-4-yl)-thiazol-2-yl, can be prepared as described in PCT Int. Appl. WO 2007089512.

The compound of formula IX, wherein $R_4$ is 5-bromo-thiazolo[5,4-b]pyridin-2-yl, can be prepared as described in PCT Int. Appl. WO 2007041365.

Compounds of formula IX, wherein $R_4$ is 4-(1,2-bis-benzoyloxy-ethyl)-thiazol-2-yl, 4-(1,3-diacetoxy-propyl)-thiazol-2-yl, 4-(2,2,4-trimethyl-[1,3]dioxolan-4-yl)-thiazol-2-yl, 4-(2,2,5,5-tetramethyl-[1,3]dioxolan-4-yl)-thiazol-2-yl, 4-(2,2-dimethyl-[1,3]dioxolan-4-yl)-thiazol-2-yl, 4-(2-acetoxy-1-acetoxymethyl-1-methyl-ethyl)-thiazol-2-yl, 4-(2-acetoxy-1-acetoxymethyl-ethyl)-thiazol-2-yl, 4-(3-acetoxy-2-acetoxymethyl-propyl)-thiazol-2-yl, 4-(4-ethyl-2,2-dimethyl-[1,3]dioxolan-4-yl)-thiazol-2-yl, 4-(ethoxycarbonyl-hydroxy-methyl)-5-ethyl-thiazol-2-yl, 5-bromo-4-ethoxyoxalyl-thiazol-2-yl, 5-chloro-4-ethoxyoxalyl-thiazol-2-yl, 4-(1,1-bis-ethoxycarbonyl-ethyl)-thiazol-2-yl, 5-(ethoxycarbonyl-hydroxy-methyl)-thiazol-2-yl or 4-((S)-1,2-bis-benzoyloxy-ethyl)-thiazol-2-yl, can be prepared as described in PCT Int. Appl. WO 2007026761.

Compounds of formula IX, wherein $R_4$ is 5-(1-ethoxycarbonyl-1-methyl-ethylsulfanyl)-thiazol-2-yl, 5-(1-ethoxycarbonyl-cyclopropylsulfamoyl)-thiazol-2-yl, 5-(1-methoxycarbonyl-cyclobutylsulfamoyl)-thiazol-2-yl, 5-(2,6-dimethyl-piperidine-1-sulfonyl)-thiazol-2-yl, 5-(2-ethoxycarbonyl-ethylsulfamoyl)-thiazol-2-yl, 5-(2-methoxycarbonyl-ethylsulfanyl)-thiazol-2-yl, 5-(2-methoxycarbonyl-pyrrolidine-1-sulfonyl)-thiazol-2-yl, 5-(ethoxycarbonylmethyl-sulfamoyl)-4-methyl-thiazol-2-yl, 5-(ethoxycarbonylmethyl-sulfamoyl)-thiazol-2-yl, 5-(methoxycarbonylmethyl-methyl-sulfamoyl)-4-methyl-thiazol-2-yl, 5-(methoxycarbonylmethyl-sulfamoyl)-thiazol-2-yl, 5-(piperidine-1-sulfonyl)-thiazol-2-yl, 5-imidazol-1-yl-thiazol-2-yl, 5-isopropylsulfamoyl-thiazol-2-yl, 5-t-butylsulfamoyl-thiazol-2-yl, or 5-((S)-2-methoxycarbonyl-pyrrolidine-1-sulfonyl)-thiazol-2-yl, can be prepared as described in PCT Int. Appl. WO 2007006760.

The compound of formula IX, wherein $R_4$ is 5-(2-carboxy-ethylsulfanyl)-thiazol-2-yl, can be prepared as described in PCT Int. Appl. WO 2007006814.

Compounds of formula IX, wherein $R_4$ is 4-methyl-5-(4-methyl-piperazine-1-sulfonyl)-thiazol-2-yl, 5-(4-methyl-piperazin-1-yl)-thiazol-2-yl, 5-chloro-4-ethoxycarbonylmethyl-thiazol-2-yl, or 5-chloro-4-ethoxycarbonylmethyl-thiazol-2-yl, can be prepared as described in PCT Int. Appl. WO 2006058923.

Compounds of formula IX, wherein $R_4$ is 5-fluoro-thiazolo[5,4-b]pyridin-2-yl or thiazolo[4,5-b]pyrazin-2-yl, can be prepared as described in PCT Int. Appl. WO 2005090332.

Compounds of formula IX, wherein $R_4$ is 4-ethoxycarbonylmethyl-5-imidazol-1-yl-thiazol-2-yl, 4-methyl-5-(1-methyl-piperidin-4-ylsulfamoyl)-thiazol-2-yl, 5-(2-ethoxycarbonyl-ethylsulfanyl)-4-methyl-thiazol-2-yl, 5-(4-methyl-piperazine-1-sulfonyl)-thiazol-2-yl, 5-(ethoxycarbonylmethyl-methyl-amino)-thiazol-2-yl, or 4-carboxymethylsulfanyl-thiazol-2-yl, can be prepared as described in PCT Int. Appl. WO 2005066145.

Compounds of formula IX, wherein $R_4$ is 4-methoxymethyl-thiazol-2-yl, 5-(1-amino-1-methyl-ethyl)-thiazol-2-yl, 5-trifluoromethyl-thiazol-2-yl, 4-acetoxymethyl-thiazol-2-yl or thiazolo[4,5-b]pyridin-2-yl, can be prepared as described in PCT Int. Appl. WO 2004081001.

Compounds of formula IX, wherein $R_4$ is 4-(1-hydroxy-1-methyl-ethyl)-thiazol-2-yl, 4-(t-butyl-dimethyl-silanyloxymethyl)-thiazol-2-yl, 4-[1-(t-butyl-dimethyl-silanyloxy)-ethyl]-thiazol-2-yl, 4-[(R)-1-(t-butyl-dimethyl-silanyloxy)-ethyl]-thiazol-2-yl, thieno[3,2-d]thiazol-2-yl or 4-[1-(t-butyl-dimethyl-silanyloxy)-ethyl]-thiazol-2-yl, can be prepared as described in PCT Int. Appl. WO 2004076420.

The compound of formula IX, wherein $R_4$ is 5-fluoro-thiazol-2-yl, can be prepared as described in PCT Int. Appl. WO 2004072031.

Compounds of formula IX, wherein $R_4$ is 4-(2-methoxycarbonyl-ethylsulfanylmethyl)-thiazol-2-yl, 4-[2-(t-butyl-dimethyl-silanyloxy)-ethyl]-thiazol-2-yl, 4-azidomethyl-thiazol-2-yl, or 4-methylcarbamoylmethyl-thiazol-2-yl, can be prepared as described in PCT Int. Appl. WO 2004002481.

The compound of formula IX, wherein $R_4$ is 5-ethoxyoxalyl-thiazol-2-yl, can be prepared as described in U.S. Pat. No. 6,610,846.

The compound of formula IX, wherein $R_4$ is 4-hydroxymethyl-thiazol-2-yl, can be prepared as described in PCT Int. Appl. WO 2001085706.

Compounds of formula IX, wherein $R_4$ is 5-formyl-thiazol-2-yl, 5-methoxymethyl-thiazol-2-yl, 5-(2-dimethylamino-ethoxy)-thiazolo[5,4-b]pyridin-2-yl, 5-ethoxycarbonylmethoxy-thiazolo[5,4-b]pyridin-2-yl, 5-t-butoxycarbonylmethoxy-thiazolo[5,4-b]pyridin-2-yl, 5-(2-hydroxy-ethoxy)-thiazolo[5,4-b]pyridin-2-yl, 5-carbamoylmethoxy-thiazolo[5,4-b]pyridin-2-yl, 5-methylcarbamoylmethoxy-thiazolo[5,4-b]pyridin-2-yl, 5-(2-t-butoxycarbonylamino-ethoxy)-thiazolo[5,4-b]pyridin-2-yl, 5-(2-amino-ethoxy)-thiazolo[5,4-b]pyridin-2-yl, 5-[2-(t-butoxycarbonyl-methyl-amino)-ethoxy]-thiazolo[5,4-b]pyridin-2-yl, 5-dimethylsulfamoyl-thiazol-2-yl, 4-(2-dimethylcarbamoyl-ethyl)-thiazol-2-yl, 5-(3-dimethylamino-propyl)-thiazol-2-yl, 5-(3-dimethylamino-propyl)-thiazol-2-yl, 5-[2-(t-butyl-dimethyl-silanyloxy)-ethoxy]-thiazolo[5,4-b]pyridin-2-yl, 5-(2-dimethylamino-ethylsulfanyl)-thiazol-2-yl, 5-(4-methyl-4H-[1,2,4]triazol-3-ylsulfanyl)-thiazol-2-yl, 5-(2-hydroxy-ethylsulfanyl)-thiazol-2-yl, 5-(3-hydroxy-propylsulfanyl)-thiazol-2-yl, 5-(2-t-butoxycarbonylamino-ethylsulfanyl)-thiazol-2-yl, 6-methoxy-thiazolo[4,5-b]pyrazin-2-yl, thiazolo[5,4-d]pyrimidin-2-yl, 5-methoxy-thiazolo[5,4-d]pyrimidin-2-yl, 5-dimethylamino-thiazolo[5,4-b]pyridin-2-yl, 5-hydroxymethyl-thiazolo[5,4-b]pyridin-2-yl, 5-(t-butyl-dimethyl-silanyloxymethyl)-thiazolo[5,4-b]pyridin-2-yl, 5-[(2-dimethylamino-ethyl)-methyl-amino]-thiazolo[5,4-b]pyridin-2-yl, 6-{[2-(t-butoxycarbonyl-methyl-amino)-ethyl]-methyl-amino}-thiazolo[5,4-b]pyridin-2-yl, 5-(2-dimethylamino-ethylamino)-thiazolo[5,4-b]pyridin-2-yl, 5-{[2-(t-butyl-dimethyl-silanyloxy)-ethyl]-methyl-amino}-thiazolo[5,4-b]pyridin-2-yl, 5-[2-(t-butyl-dimethyl-silanyloxy)-ethylamino]-thiazolo[5,4-b]pyridin-2-yl, 5-methylamino-thiazolo[5,4-b]pyridin-2-yl, 5-(1-t-butoxycarbonyl-piperidin-4-yloxy)-thiazolo[5,4-b]pyridin-2-yl, 5-((S)-1-t-butoxycarbonyl-pyrrolidin-3-yloxy)-thiazolo[5,4-b]pyridin-2-yl, 5-(1-t-butoxycarbonyl-pyrrolidin-3-yloxy)-thiazolo[5,4-b]pyridin-2-yl, 5-(1-t-butoxycarbonyl-azetidin-3-yloxy)-thiazolo[5,4-b]pyridin-2-yl, 5-(2-t-butoxycarbonylamino-2-methyl-propoxy)-thiazolo[5,4-b]pyridin-2-yl, 5-[3-(t-butoxycarbonyl-methyl-amino)-propoxy]-thiazolo[5,4-b]pyridin-2-yl, 4-(4-methyl-piperazin-1-ylmethyl)-thiazol-2-yl, 4-(4-methyl-[1,4]diazepan-1-ylmethyl)-thiazol-2-yl, 5-(4-acetyl-3-methyl-piperazin-1-ylmethyl)-thiazol-2-yl, 5-(4-methyl-piperazin-1-ylmethyl)-thiazol-2-yl, 5-(1-t-butoxycarbonyl-piperidin-4-ylsulfanyl)-thiazol-2-yl, 6-[2-(t-butyl-dimethyl-silanyloxy)-ethoxy]-benzothiazol-2-yl, 6-[2-(t- butoxycarbonyl-methyl-amino)-ethoxy]-benzothiazol-2-yl, 6-(2-dimethylamino-ethoxy)-benzothiazol-2-yl, 5-aminothiazolo[5,4-b]pyridin-2-yl, or 5-oxo-4,5-dihydro-thiazolo [5,4-b]pyridin-2-yl, can be prepared as described in PCT Int. Appl. WO 2007007886.

Compounds of formula IX, wherein $R_4$ is 5-hydroxymethyl-pyridin-2-yl, 5-trifluoromethyl-pyridin-2-yl, 5-sulfamoyl-pyridin-2-yl, 5-bromo-6-methyl-pyridin-2-yl, 5-carboxymethyl-pyridin-2-yl, 5-methoxycarbonyl-pyridin-2-yl, 5-phenyl-pyridin-2-yl, 4-ethyl-pyridin-2-yl, isoquinolin-3-yl, 5-fluoro-pyridin-2-yl, 5-acetyl-pyridin-2-yl, 6-bromo-pyridin-2-yl, 4-ethoxycarbonyl-pyridin-2-yl, 4-methoxy-pyridin-2-yl, 5-nitro-pyridin-2-yl, 5-cyano-pyridin-2-yl, 5-carboxy-pyridin-2-yl, 6-methyl-pyridin-2-yl, 5-methylpyridin-2-yl, 5-chloro-pyridin-2-yl, 5-bromo-pyridin-2-yl, 4-methyl-pyridin-2-yl, quinolin-2-yl, pyridin-2-yl, or 5-carbamoyl-pyridin-2-yl, are commercially available.

Compounds of formula IX, wherein $R_4$ is 4-bromo-pyridin-2-yl or 5-(diethoxy-phosphorylmethyl)-pyridin-2-yl, can be prepared as described in PCT Int. Appl. WO 2008005964.

The compound of formula IX, wherein $R_4$ is 5-(t-butyldimethyl-silanyloxymethyl)-pyridin-2-yl, can be prepared as described in PCT Int. Appl. WO 2007122482.

The compound of formula IX, wherein $R_4$ is 5-benzyloxy-pyridin-2-yl, can be prepared as described in PCT Int. Appl. WO 2007117381.

Compounds of formula IX, wherein $R_4$ is 4-(2,6-difluorophenoxy)-pyridin-2-yl, 4-(quinolin-5-yloxy)-pyridin-2-yl, 5-bromo-4-(2,6-difluoro-phenoxy)-pyridin-2-yl, 5-bromo-4-(5-ethoxycarbonyl-2,4-dimethyl-pyridin-3-yloxy)-pyridin-2-yl, 5-bromo-4-ethoxycarbonylmethyl-pyridin-2-yl, 4-ethoxycarbonylmethyl-pyridin-2-yl, 4-benzyloxy-5-bromo-pyridin-2-yl, 5-bromo-4-(4-methoxy-benzylsulfanyl)-pyridin-2-yl, 4-(4-methoxy-benzylsulfanyl)-pyridin-2-yl, 4-(2-chloro-5-ethoxycarbonyl-phenoxy)-pyridin-2-yl, or 4-benzyloxy-pyridin-2-yl, can be prepared as described in PCT Int. Appl. WO 2007089512.

The compound of formula IX, wherein $R_4$ is 5-[5-(2-methoxy-phenyl)-1H-pyrazol-3-yl]-pyridin-2-yl, can be prepared as described in PCT Int. Appl. WO 2007061923.

Compounds of formula IX, wherein $R_4$ is 5-benzyloxycarbonyl-pyridin-2-yl, 5-methoxymethoxymethyl-pyridin-2-yl, 3-trimethylsilyloxycarbonyl-pyridin-2-yl, 5-((E)-2-ethoxycarbonyl-vinyl)-pyridin-2-yl, or 5-methanesulfonyl-pyridin-2-yl, can be prepared as described in U.S. Pat. Appl. US 2007099930.

Compounds of formula IX, wherein $R_4$ is 5-(4-acetyl-3-methyl-piperazin-1-ylmethyl)-pyridin-2-yl, 5-methoxycarbonylmethylsulfanyl-pyridin-2-yl, or 2-amino-thiazolo[5,4-b]pyridin-5-yl, can be prepared as described in PCT Int. Appl WO 2007007886.

The compound of formula IX, wherein $R_4$ is 5-((E)-2-ethoxycarbonyl-vinyl)-pyridin-2-yl, can be prepared as described in PCT Int. Appl. WO 2005066145.

Compounds of formula IX, wherein $R_4$ is 5-(tetrahydrofuran-2-yl)-pyridin-2-yl, 5-methanesulfonylamino-pyridin-2-yl or 5-dimethylamino-pyridin-2-yl, can be prepared as described in PCT Int. Appl. WO 2004052869.

The compound of formula IX, wherein $R_4$ is 5-[t-butoxycarbonyl-(2-methoxy-ethyl)-amino]-pyridin-2-yl, can be prepared as described in PCT Int. Appl. WO 2003015774.

Compounds of formula IX, wherein $R_4$ is 3-methoxy-[1,2,4]thiadiazol-5-yl, 3-methyl-[1,2,4]thiadiazol-5-yl, [1,2,4]thiadiazol-5-yl, or 3-methylsulfanyl-[1,2,4]thiadiazol-5-yl are commercially available.

Compounds of formula IX, wherein $R_4$ is 3-hydroxymethyl-[1,2,4]thiadiazol-5-yl or 3-cyclopropyl-[1,2,4]thiadiazol-5-yl, can be prepared as described in PCT Int. Appl. WO 2004081001.

The compound of formula IX, wherein $R_4$ is 3-(t-butyldimethyl-silanyloxymethyl)-[1,2,4]thiadiazol-5-yl, can be prepared as described in PCT Int. Appl. WO 2004076420.

The compound of formula IX, wherein $R_4$ is 3-(2-hydroxyethyl)-[1,2,4]thiadiazol-5-yl, can be prepared as described in Jpn. Kokai Tokkyo Koho JP 08151386.

Compounds of formula IX, wherein $R_4$ is 2-methyl-2H-[1,2,3]triazol-4-yl, can be prepared as described in PCT Int. Appl. WO 2007122482. 2-fluoro-phenyl-2H-[1,2,4]triazol-3-yl, 3,5-dimethoxy-phenyl-2H-[1,2,4]triazol-3-yl, 2,4-dinitro-phenyl-2H-[1,2,4]triazol-3-yl, 2-methoxy-phenyl-2H-[1,2,4]triazol-3-yl, 4-chloro-phenyl-2H-[1,2,4]triazol-3-yl, 3,4,5-trimethoxy-phenyl-2H-[1,2,4]triazol-3-yl, 5-isopropyl-2H-[1,2,4]triazol-3-yl, or 2H-[1,2,4]triazol-3-yl, are commercially available.

The compound of formula IX, wherein $R_4$ is 5-hydroxymethyl-[1,3,4]thiadiazol-2-yl can be prepared as described in *Pharmazie* 2003, 58, 367.

Compounds of formula IX, wherein $R_4$ is 5-(thiazol-2-ylcarbamoylmethylsulfanyl)-[1,3,4]thiadiazol-2-yl, 5-(1-t-butoxycarbonyl-1-methyl-ethylsulfanyl)-[1,3,4]thiadiazol-2-yl, 5-ethoxycarbonylmethyl-[1,3,4]thiadiazol-2-yl, 5-ethoxycarbonyl-[1,3,4]thiadiazol-2-yl, 5-cyclopropyl-[1,3,4]thiadiazol-2-yl, 5-ethoxycarbonylmethylsulfanyl-[1,3,4]thiadiazol-2-yl, 5-ethylsulfanyl-[1,3,4]thiadiazol-2-yl, 5-trifluoromethyl-[1,3,4]thiadiazol-2-yl, 5-methylsulfanyl-[1,3,4]thiadiazol-2-yl, 5-furan-2-yl-[1,3,4]thiadiazol-2-yl, [1,3,4]thiadiazol-2-yl, 5-thioxo-4,5-dihydro-[1,3,4]thiadiazol-2-yl, 5-phenyl-[1,3,4]thiadiazol-2-yl, or 5-methyl-[1,3,4]thiadiazol-2-yl, are commercially available.

Compounds of formula IX, wherein $R_4$ is 5-phenylsulfamoyl-[1,3,4]thiadiazol-2-yl, 5-isopropylsulfamoyl-[1,3,4]thiadiazol-2-yl, 5-(2-methoxy-ethylsulfamoyl)-[1,3,4]thiadiazol-2-yl, 5-(piperidine-1-sulfonyl)-[1,3,4]thiadiazol-2-yl, 5-(ethoxycarbonylmethyl-methyl-sulfamoyl)-[1,3,4]thiadiazol-2-yl, or 5-(ethoxycarbonylmethyl-sulfamoyl)-[1,3,4]thiadiazol-2-yl, can be prepared as described in PCT Int. Appl. WO2007006760.

The compound of formula IX, wherein $R_4$ is 5-(3-ethoxycarbonyl-propylsulfanyl)-[1,3,4]thiadiazol-2-yl, can be prepared as described in PCT Int. Appl. WO 2005080360.

Compounds of formula IX, wherein $R_4$ is 5-(2-ethoxycarbonyl-ethylsulfanyl)-[1,3,4]thiadiazol-2-yl or 5-(2-methoxycarbonyl-ethyl)-[1,3,4]thiadiazol-2-yl, can be prepared as described in PCT Int. Appl. WO 2007006814.

Compounds of formula IX, wherein $R_4$ is 2-methyl-2H-[1,2,3]triazol-4-yl, can be prepared as described in PCT Int. Appl. WO 2007122482.

Compounds of formula IX, wherein $R_4$ is 2-fluoro-phenyl-2H-[1,2,4]triazol-3-yl, 3,5-dimethoxy-phenyl-2H-[1,2,4]triazol-3-yl, 2,4-dinitro-phenyl-2H-[1,2,4]triazol-3-yl, 2-methoxy-phenyl-2H-[1,2,4]triazol-3-yl, 4-chloro-phenyl-2H-[1,2,4]triazol-3-yl, 3,4,5-trimethoxy-phenyl-2H-[1,2,4]triazol-3-yl, 5-isopropyl-2H-[1,2,4]triazol-3-yl, or 2H-[1,2,4]triazol-3-yl, are commercially available.

Compounds of formula IX, wherein $R_4$ is a substituted or unsubstituted pyrimidin-4-yl group, for example, pyrimidin-4-yl and 2-methyl-pyrimidin-4-yl, are commercially available.

Compounds of formula IX, wherein $R_4$ is a substituted pyridazin-3-yl group, for example, 6-methyl-pyridazin-3-yl, pyridazin-3-yl and 6-chloro-pyridazin-3-yl, are commercially available.

Compounds of formula IX, wherein $R_4$ is a thiazol-4-yl group, can be prepared as described in PCT Int. Appl. WO 2004081001.

Compounds of formula IX, wherein $R_4$ is a substituted dihydro-1H-[1,2,4]triazol-3-yl group, for example, 5-thioxo-2,5-dihydro-1H-[1,2,4]triazol-3-yl, are commercially available.

The compound of formula IX, wherein $R_4$ is a 1H-imidazol-2-yl group, is commercially available.

The compound of formula IX, wherein $R_4$ is a 1H-benzoimidazol-2-yl group, is commercially available.

The compound of formula IX, wherein $R_4$ is a [1,2,5]thiadiazol-3-yl group, is commercially available.

The compound of formula IX, wherein $R_4$ is an oxazol-2-yl group, is commercially available.

The compound of formula IX, wherein $R_4$ is a benzooxazol-2-yl group, is commercially available.

Compounds of formula IX, wherein $R_4$ is a substituted 4,5-dihydro-oxazol-2-yl group, for example, 4-trifluoromethyl-phenyl-4,5-dihydro-oxazol-2-yl, are commercially available.

Compounds of formula IX, wherein $R_4$ is a substituted or unsubstituted pyrimidin-2-yl group, for example, pyrimidin-2-yl and 4-methyl-pyrimidin-2-yl, are commercially available.

Compounds of formula IX, wherein $R_4$ is a substituted [1,2,4]oxadiazol-5-yl group, for example, 3-methyl-[1,2,4]oxadiazol-5-yl, are commercially available.

Compounds of formula IX, wherein $R_4$ is a substituted or unsubstituted isoxazol-3-yl group, for example, isoxazol-3-yl and 5-methyl-isoxazol-3-yl, are commercially available.

The compound of formula IX, wherein $R_4$ is a [1,2,4]triazin-3-yl group, is commercially available.

The compound of formula IX, wherein $R_4$ is a [1,2,4]triazolo[1,5-a]pyridin-2-yl group, can be prepared as described in PCT Int. Appl. WO 2004081001.

The following schemes describe how to make certain compounds of formula IX.

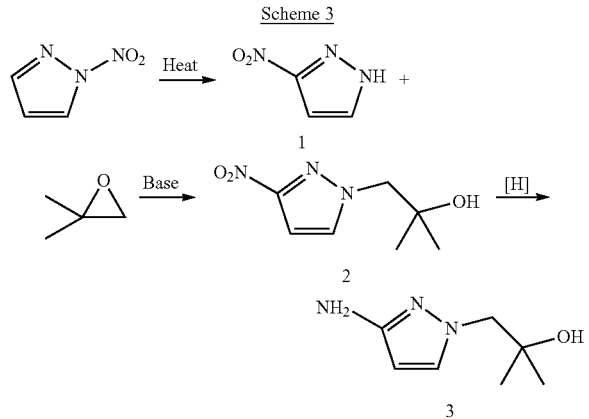

Compound 3 may be synthesized following the reactions outlined in Scheme 3. The nitropyrazole of compound 1 can be prepared by methods described in the literature (under similar conditions to those described in *J. Org. Chem.*, 1971, 36, 3081; *J. Org. Chem.*, 1973, 38, 1777). Compound 1 may then be treated with an epoxide, such as 2,2-dimethyl-oxirane, under basic conditions to produce compound 2 (under similar conditions to those described in *Tet. Lett.* 1992, 33, 4069; *J. Med. Chem.* 1990, 33, 868; *J. Med. Chem.*, 2005, 48, 5162). The nitro group of compound 2 may then be converted to an amino group under standard reduction conditions to produce compound 3 as shown in Scheme 1 (under similar conditions to those described in *J. Chem. Soc., Perkin Trans.* 1 1977, 672; U.S. Pat. Appl. US 2008021032).

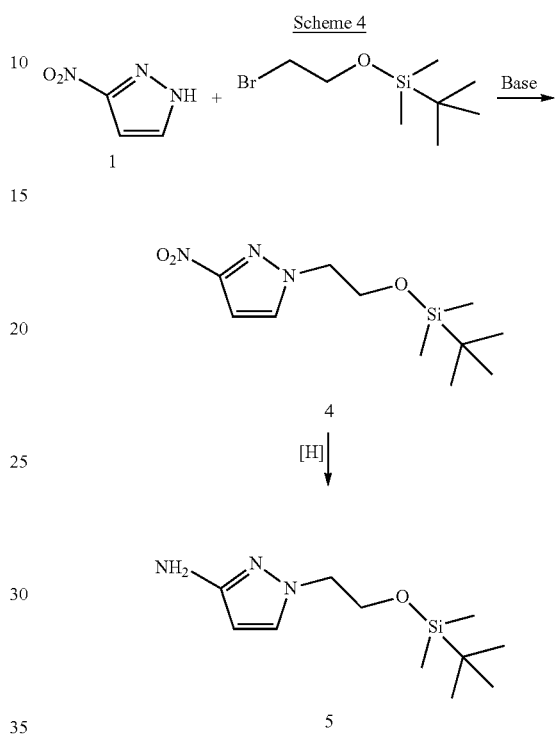

Compound 5 may be synthesized following the reactions outlined in Scheme 4. The nitropyrazole of compound 1 can be prepared by methods described in the literature (under similar conditions to those described in *J. Org. Chem.*, 1971, 36, 3081-4; *J. Org. Chem.*, 1973, 38, 1777-82). Compound 1 may then be treated with a commercially available reagent, for example, (2-bromo-ethoxy)-t-butyl-dimethyl-silane, under basic conditions to produce compound 4 (under similar conditions to those described in *J. Med. Chem.*, 2005, 48, 5162). A commercially available alkyl halide containing an unprotected hydroxyl group may also be converted to an appropriate reagent for this alkylation (for representative examples see Greene, T. W. *Protective Groups in Organic Synthesis*; John Wiley & Sons, Inc.: New York, 1991, p. 77-81). The nitro group of compound 4 may then be converted to an amino group under standard reduction conditions to produce compound 5 as shown in Scheme 2 (under similar conditions to those described in *J. Chem. Soc., Perkin Trans. I*, 1977, 672; U.S. Pat. Appl. US 2008021032).

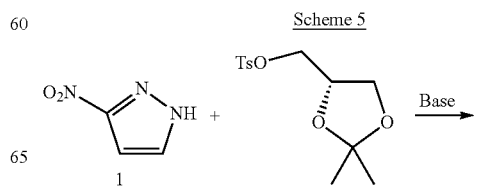

-continued

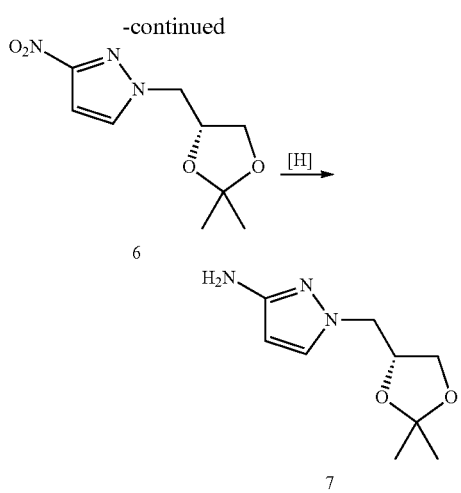

Compound 7 may be synthesized following the reactions outlined in Scheme 3. The nitropyrazole of compound 1 can be prepared by methods described in the literature (under similar conditions to those described in *J. Org. Chem.*, 1971, 36, 3081; *J. Org. Chem.*, 1973, 38, 1777). Compound 1 may then be treated with a commercially available reagent, for example, p-toluenesulfonic acid ((4R)-2,2-dimethyl-1,3-dioxolan-4-yl)methyl ester, under basic conditions to produce compound 6 (under similar conditions to those described in *J. Med. Chem.*, 1987, 30, 552; *J. Med. Chem.*, 2005, 48, 5162). The nitro group of compound 6 may then be converted to an amino group under standard reduction conditions to produce compound 7 as shown in Scheme 3 (under similar conditions to those described in *J. Chem. Soc., Perkin Trans. I*, 1977, 672). The opposite enantiomer may be made in the same manner utilizing starting materials of the opposite chirality.

Compound 10 may be synthesized following the reactions outlined in Scheme 6. The nitropyrazole of compound 1 can be prepared by methods described in the literature (under similar conditions to those described in *J. Org. Chem.*, 1971, 36, 3081; *J. Org. Chem.*, 1973, 38, 1777). Compound 1 may then be treated with a commercially available reagent, for example, (R)-1-oxiranyl-methanol, under basic conditions to produce compound 8 (under similar conditions to those described in *Tet. Lett.* 1992, 33, 4069; *J. Med. Chem.* 1990, 33, 868; *J. Med. Chem.*, 2005, 48, 5162). Compound 8 may then be treated with 2,2-dimethoxypropane under acidic conditions to produce the compound 9 (for representative examples see Greene, T. W. *Protective Groups in Organic Synthesis*; John Wiley & Sons, Inc.: New York, 1991, p. 123-127; *J. Org. Chem.* 1986, 51, 2637). The nitro group of compound 9 may then be converted to an amino group under standard reduction conditions to produce compound 10 as shown in Scheme 4 (under similar conditions to those described in *J. Chem. Soc., Perkin Trans. I*, 1977, 672; U.S. Pat. Appl. US 2008021032). The opposite enantiomer may be made in the same manner utilizing starting materials of the opposite chirality.

Scheme 7

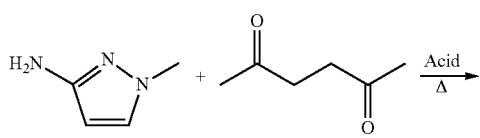

Scheme 6

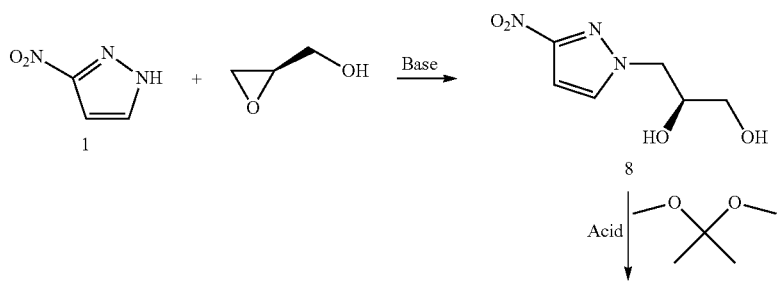

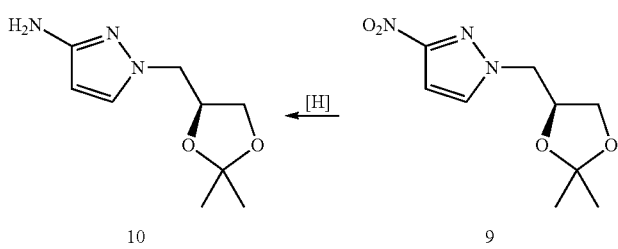

-continued

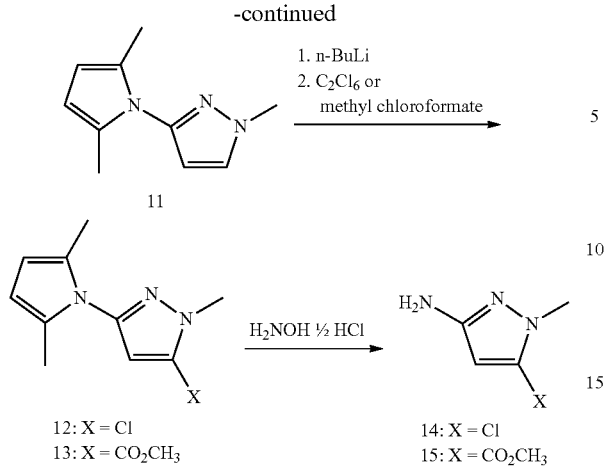

11

12: X = Cl
13: X = CO$_2$CH$_3$

14: X = Cl
15: X = CO$_2$CH$_3$

Compounds 14 and 15 may be synthesized following the reactions outlined in Scheme 7. Commercially available 1-methyl-1H-pyrazole-3-amine may be treated with acetonylacetone to afford compound 11 (under similar conditions to those described in *Synthesis*, 1998, 1599; PCT Int. Appl. WO 2005044264). The pyrazole of compound 11 can then be converted to either compound 12 or compound 13 by methods described in the literature (under similar conditions to those described in PCT Int. Appl WO 2003087098; Eur. Pat. Appl EP 0138622) The dimethylpyrrole protecting group then can be removed to unmask the corresponding free amine to produce compound 14 and 15 as shown in Scheme 5 (under similar conditions to those described in *Synthesis*, 1998, 1599; PCT Int. Appl. WO 2005044264 Eur. Pat. Appl. EP 0138622).

Scheme 8

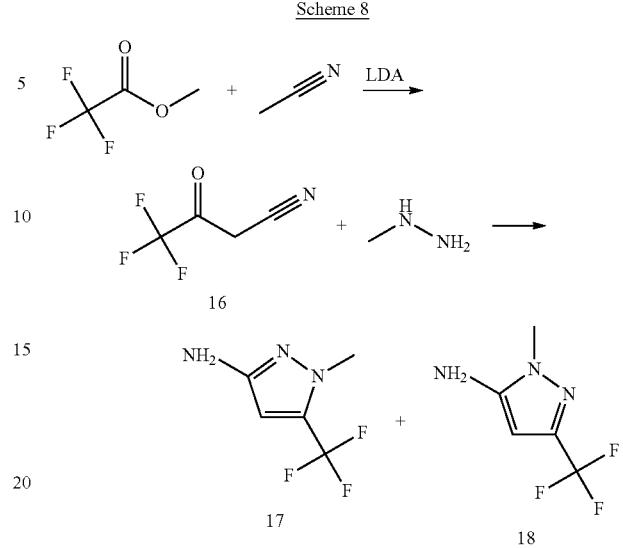

Compounds 17 and 18 may be synthesized following the reactions outlined in Scheme 8. Commercially available methyl trifluoracetate may be treated with acetonitrile in the presence of base to afford compound 16 (under similar conditions to those described in Eur. Pat. App. EP 0220025). Compound 16 can then be treated with methylhydrazine at elevated temperatures to afford a mixture of compounds 17 and 18 as shown in Scheme 6 (under similar conditions to those described in Eur. Pat. Appl. EP 0542388).

Scheme 9

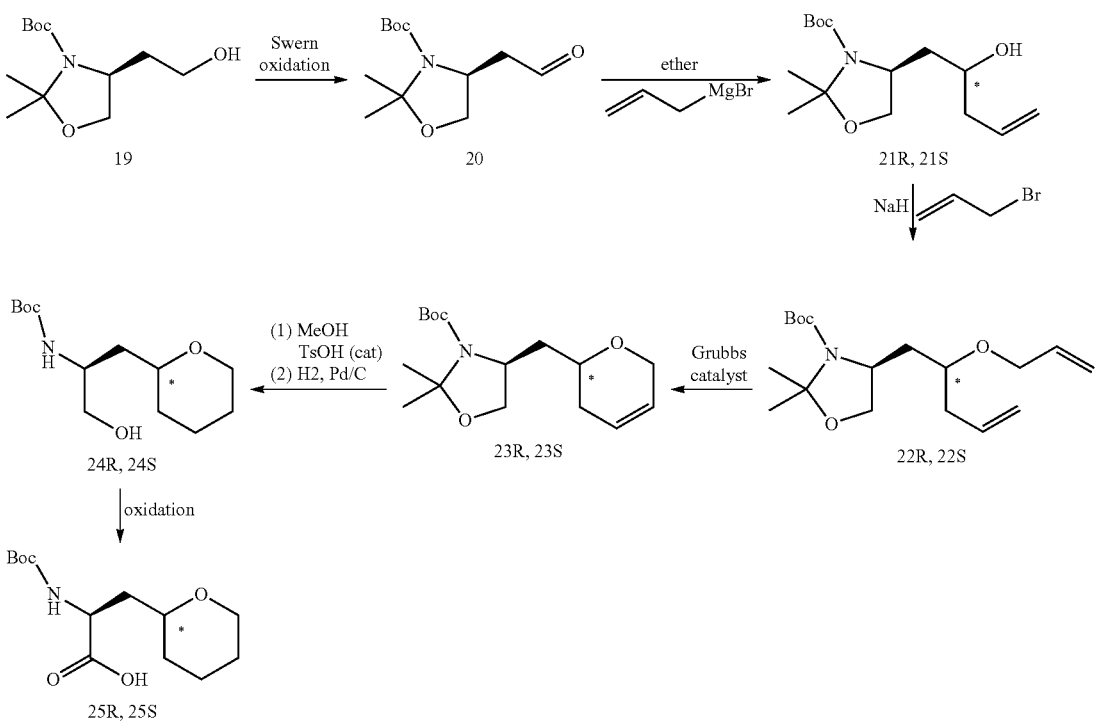

Compounds 25R and 25S may be synthesized following the reactions outlined in Scheme 9. Compound 19 can be prepared and oxidized under Swern conditions to give the corresponding aldehyde 20 as described in PCT Int. Appl. 2006094770; *J. Org. Chem.* 2001, 66, 206. Aldehyde 20 can be treated with allyl magnesium bromide to afford a mixture of diasteromeric alcohols 21R and 21S (under similar conditions to those described in *Synlett*, 2005, 13, 2083) which can be chromatographically separated. Either diastereomer 21R or 21S can be treated with base, such as sodium hydride and then allylated with allyl bromide to afford the corresponding ethers 22R or 22S. Either ether can be cyclized under Grubbs ring closing methasis conditions to give dihydropyrans 23R or 23S (under similar conditions to those described in *Tetrahedron Lett.*, 2007, 48, 1417). These compounds can be treated with methanol under acidic conditions and further hydrogenated to give the corresponding protected amino alcohols 24R or 24S. Oxidation of the alcohol to an acid yields the corresponding protected amino acids 25R or 25S.

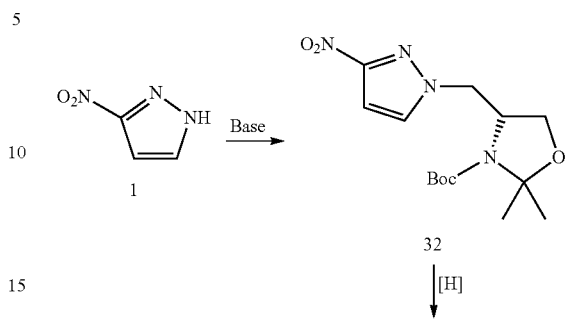

Compounds 29R and 29S may be synthesized following the reactions outlined in Scheme 10. Aldehyde 20 can be treated with alkyl magnesium bromides (under similar conditions to those described in *Synlett*, 2005, 13, 2083) to afford a mixture of diasteromeric alcohols 26R and 26S which can be chromatographically separated. Either diastereomer 26R or 26S can be treated with base, such as sodium hydride and then allylated with alkyl halides to afford the corresponding ethers 27R or 27S. These compounds can be treated with methanol under acidic conditions to give the corresponding protected amino alcohols 28R or 28S. Oxidation of the alcohol to an acid yields the corresponding protected amino acids 29R or 29S.

Compound 33 may be synthesized following the reactions outlined in Scheme 11. The nitropyrazole of compound 1 can be prepared by methods described in the literature (under similar conditions to those described in *J. Org. Chem.*, 1971, 36, 3081; *J. Org. Chem.*, 1973, 38, 1777). Compound 31 may be prepared by treating commercially available Compound 30 by a two step procedure involving first the reduction of the aldehyde to an alcohol followed by treatment with tosyl chloride. Compound 1 may then be treated with Compound 30 under basic conditions to produce compound 32 (under similar conditions to those described in *J. Med. Chem.*, 1987, 30, 552; *J. Med. Chem.*, 2005, 48, 5162). The nitro group of compound 32 may then be converted to an amino group under standard reduction conditions to produce compound 33 as shown in Scheme 9 (under similar conditions to those described in *J. Chem. Soc., Perkin Trans. I*, 1977, 672). The opposite enantiomer may be made in the same manner utilizing starting materials of the opposite chirality.

Scheme 12

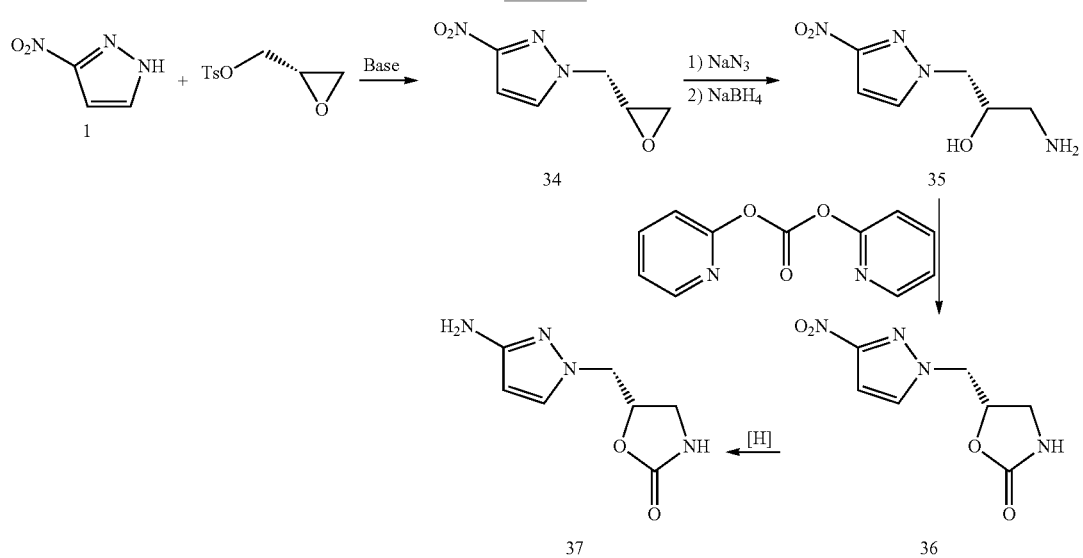

Compound 37 may be synthesized following the reactions outlined in Scheme 12. The nitropyrazole of compound 1 can be prepared by methods described in the literature (under similar conditions to those described in *J. Org. Chem.*, 1971, 36, 3081; *J. Org. Chem.*, 1973, 38, 1777). Compound 1 may then be treated with a commercially available reagent, for example, (S)-glycidol tosylate, under basic conditions to produce compound 34 (under similar conditions to those described in *Tet. Lett.* 1992, 33, 4069; *J. Med. Chem.* 1990, 33, 868; *J. Med. Chem.*, 2005, 48, 5162). Compound 34 may then be treated sodium azide, followed by sodium borohydride reduction to produce the compound 35. Compound 35 may then be treated with di-2-pyridyl carbonate to give compound 36. The nitro group of compound 36 may then be converted to an amino group under standard reduction conditions to produce compound 37 as shown in Scheme 10 (under similar conditions to those described in *J. Chem. Soc., Perkin Trans. 1*, 1977, 672; U.S. Pat. Appl. US 2008021032). The opposite enantiomer may be made in the same manner utilizing starting materials of the opposite chirality.

Scheme 13

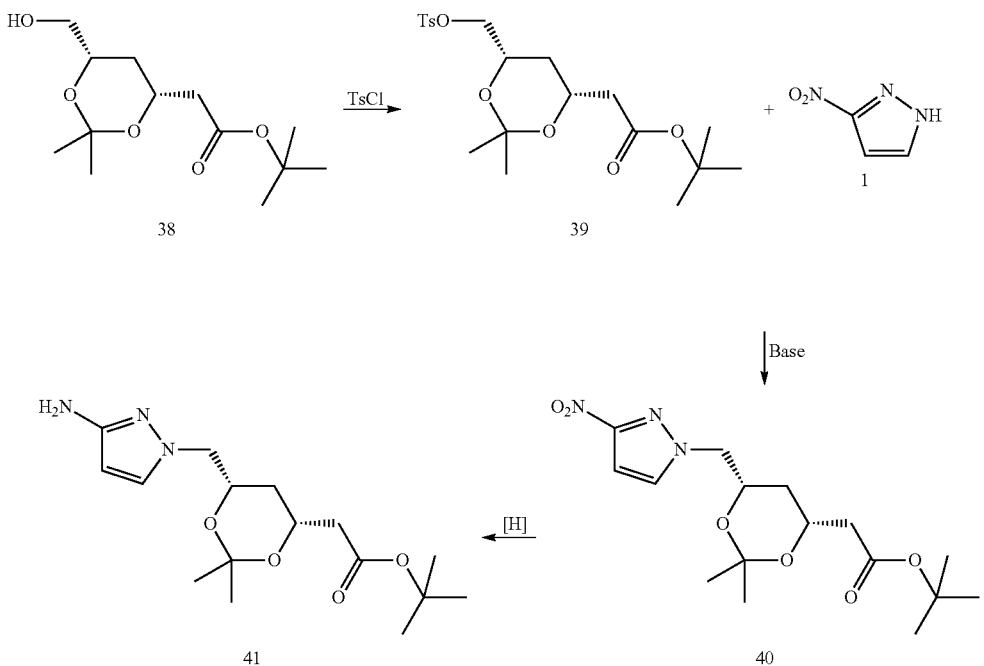

Compound 41 may be synthesized following the reactions outlined in Scheme 13. The nitropyrazole of compound 1 can be prepared by methods described in the literature (under similar conditions to those described in *J. Org. Chem.*, 1971, 36, 3081; *J. Org. Chem.*, 1973, 38, 1777). Compound 39 may be prepared by treating commercially available compound 38 by treatment with tosyl chloride. Compound 1 may then be treated with compound 39 under basic conditions to produce compound 40 (under similar conditions to those described in *J. Med. Chem.*, 1987, 30, 552; *J. Med. Chem.*, 2005, 48, 5162). The nitro group of compound 40 may then be converted to an amino group under standard reduction conditions to produce compound 41 as shown in Scheme 11 (under similar conditions to those described in *J. Chem. Soc., Perkin Trans. I*, 1977, 672).

described in *Angew. Chem., Int. Ed.*, 2007, 46, 8266). The opposite enantiomer may be made in the same manner utilizing starting materials of the opposite chirality.

Scheme 15

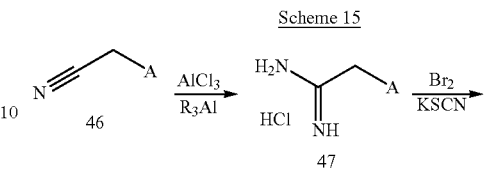

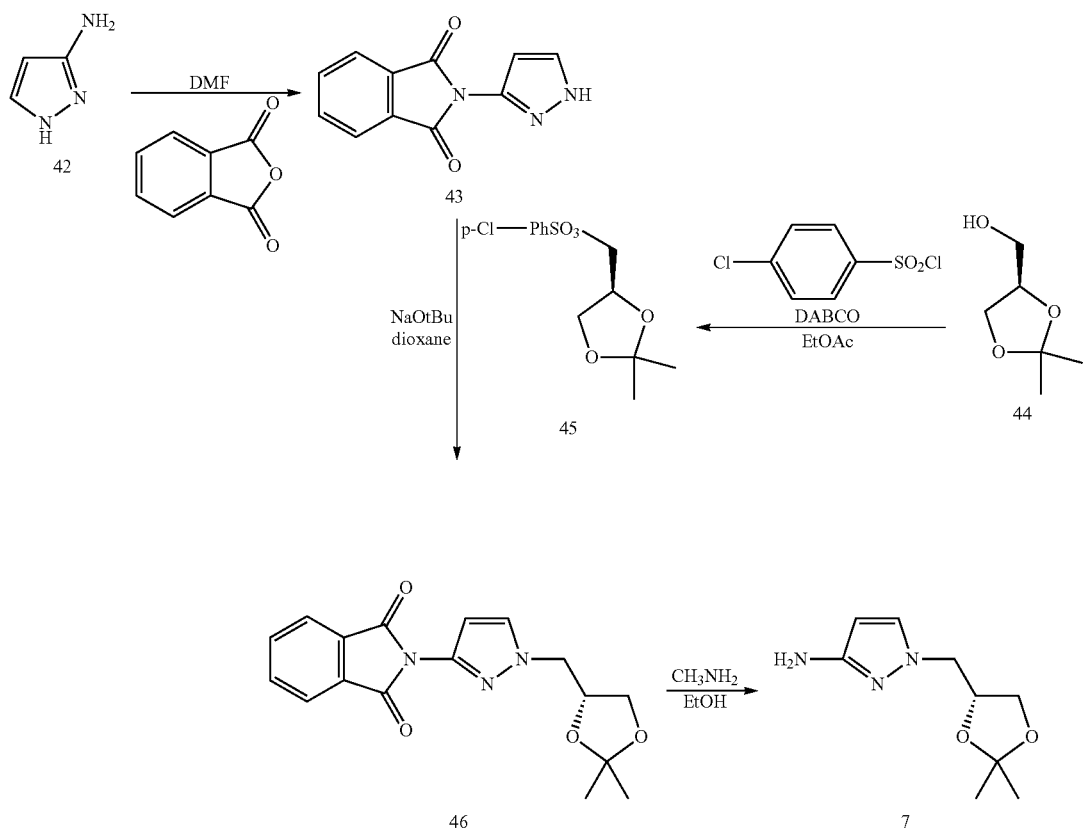

Scheme 14

Compound 7 may also be synthesized following the reactions outlined in Scheme 14. Aminopyrazole, compound 42, is commercially available and can be treated with phthalic anhydride to give compound 43 (under similar conditions to those described in *J. Med. Chem.* 2007, 50, 1584). Compound 44 may be treated with 4-chlorobenzenesulfonyl chloride under basic conditions to produce compound 45 (under similar conditions to those described in *Eur. J. Org. Chem.* 2006, 24, 5543). Compound 43 may then be treated with compound 45 under basic conditions to give compound 46 (under similar conditions to those described in *J. Med. Chem.*, 1987, 30, 552; *J. Med. Chem.*, 2005, 48, 5162). The phthalimide group of compound 46 may then be converted to an amino group under standard deprotection conditions to produce compound 7 as shown in Scheme 12 (under similar conditions to those -continued

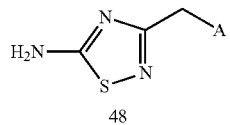

A = e.g. OMe, CH₂OMe, CH₂CF₃

Compounds of formula 48 may be synthesized following the reactions outlined in Scheme 15. Nitriles of formula 46, such as methoxy acetonitrile, 3-methoxy-propionitrile, and 4,4,4-trifluoro-butyronitrile are commercially available, or can be prepared using standard methods from alkyl halides, alkyl mesylates, alkyl tosylates or aldehydes and can be converted to Compounds of formula 47 by treatment with Lewis acids (under similar conditions to those described in PCT Int. Appl., 2005090291). Compounds of formula 47 can then be treated with bromine and potassium thiocyanate to give the corresponding thiadiazole compounds of formula 48 (under similar conditions to those described in Jpn. Kokai Tokkyo Koho, 04077477).

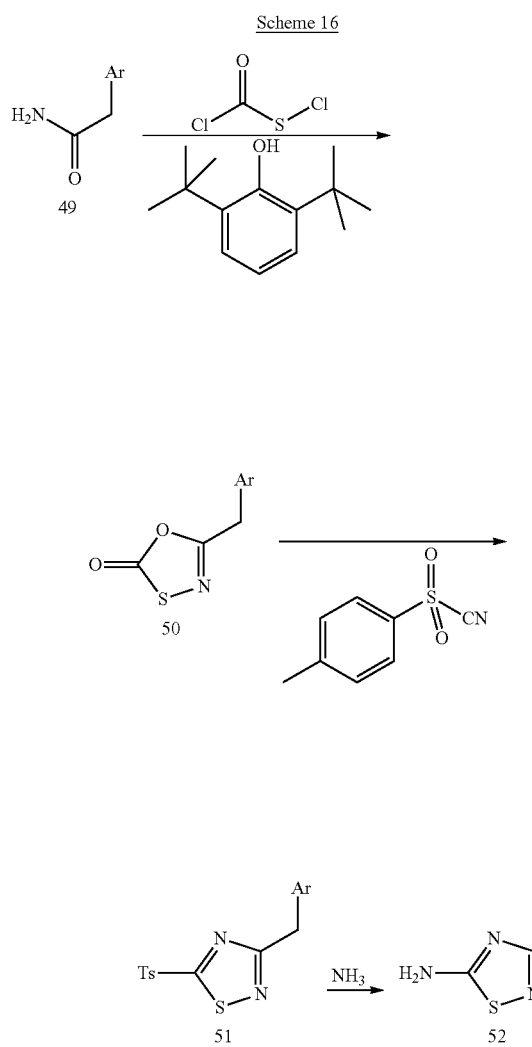

Compounds of formula 52 may be synthesized following the reactions outlined in Scheme 16. Aryl acetamides of formula 49, such as p-methoxyphenylacetamide are commercially available and can be converted to compounds of formula 50 by treatment with chlorocarbonylsulfenyl chloride (under similar conditions to those described in *J. Chem. Soc., Perk. Trans.* 1; 1981, 11, 2991). Compounds of formula 50 can then be treated with 4-toluenesulfonylcyanide to give the corresponding tosyl thiadiazole compounds of formula 51 which can then be treated with ammonia to give compounds of formula 52 (under similar conditions to those described in *Bioorg. & Med. Chem.*, 2003, 11, 5529).

The carboxylic acid of the compounds of formula VIII and the amines of formula IX may be converted to the compounds of formula I through any conventional means to form an amide bond between a carboxylic acid and an amine (see for example, Montalbetti, C. A. G. N., Falque, V., Tetrahedron, 2005, 61, 10827-10852).

EXAMPLES

The invention will be more fully understood by reference to the following examples. The examples should not, however, be construed as limited the scope of the invention.

Example 1

(S)-2-(8-Chloro-3-oxo-3,9-dihydro-1H-chromeno[2,3-c]pyrrol-2-yl)-3-cyclohexyl-N-pyridin-2-yl-propionamide

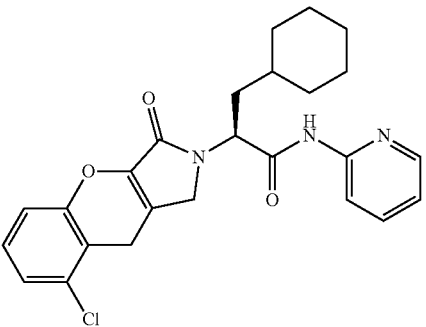

Step 1

(E)-4-Oxo-but-2-enoic acid ethyl ester (4.60 mL, 38.32 mmol), 2-nitrobenzoic acid (1.08 g, 6.39 mmol), and pyrrolidine (0.53 mL, 6.39 mmol) were added simultaneously to a solution of commercially available 2-chloro-6-hydroxy-benzaldehyde (5.0 g, 31.93 mmol) in dimethysulfoxide (30 mL) at 25° C. and the solution was stirred for 78 hours at 25° C. The reaction was quenched by the addition of water. The reaction mixture was then partitioned between water and ethyl acetate. The combined organics were washed with a saturated brine solution, dried over anhydrous sodium sulfate, filtered, rinsed and concentrated in vacuo. The residue obtained was purified on a silica gel Flash column chromatography using ethyl acetate-hexanes (1:1.2) as eluents, yielding 5-chloro-3-formyl-2H-chromene-2-carboxylic acid ethyl ester as a solid (2.08 g, 49.5%).

Step 2 a) To a solution of 5-chloro-3-formyl-2H-chromene-2-carboxylic acid ethyl ester (1.0 g, 3.74 mmol) in methanol (20 mL) containing molecular sieves (0.7 g) was added commercially available (S)-2-amino-3-cyclohexyl-propionic acid methyl ester (0.83 g, 3.74 mmol) and N,N'-diisopropylethylamine (1.30 mL, 7.49 mmol). The mixture was stirred at 25° C. for 10 h. At this time, sodium cyanoborohydride (0.47 g, 7.49 mmol) and acetic acid (0.47 mL, 7.49 mmol) were added simultaneously to the reaction mixture, and the reaction mixture was stirred for additional 16 hours at 25° C. The reaction mixture was then filtered through celite and washed with methanol. The filtrate was concentrated in vacuo. Flash column chromatography (eluant-ethyl acetate:petroleum ether 1:19, $R_f$=0.6) over neutral alumina afforded 5-chloro-3-[((S)-2-cyclohexyl-1-methoxycarbonyl-ethylamino)-methyl]-2H-chromene-2-carboxylic acid ethyl ester (0.6 g, 35.7%) as an oil.

A solution of 5-chloro-3-[((S)-2-cyclohexyl-1-methoxy-carbonyl-ethylamino)-methyl]-2H-chromene-2-carboxylic acid ethyl ester (0.75 g, 1.37 mmol) and N,N'-diisopropylethyl amine (0.98 mL, 5.50 mmol) in acetonitrile (2 mL) was heated in a sealed tube at 140° C. for 48 hours. The reaction mixture, after aqueous work-up, was extracted with ethyl acetate (3×). The combined ethyl acetate layer was washed with brine, and dried over anhydrous sodium sulfate. The organic layer was concentrated in vacuo and the residue was purified over neutral alumina using hexanes-ethyl acetate (1:1.2) as eluents to afford (S)-2-(8-chloro-3-oxo-3,3a-dihydro-1H-chromeno[2,3-c]pyrrol-2-yl)-3-cyclohexyl-propionic acid methyl ester (0.4 g, 74.6%) as a solid.

c) A solution of (S)-2-(8-chloro-3-oxo-3,3a-dihydro-1H-chromeno[2,3-c]pyrrol-2-yl)-3-cyclohexyl-propionic acid methyl ester (1.5 g, 4.0 mmol) and lithium hydroxide monohydrate (0.22 g, 5.22 mmol) was stirred at 25° C. for 2 hours in tetrahydrofuran-water (3:1) mixture (50 mL). The reaction mixture was concentrated in vacuo to remove tetrahydrofuran, and the residue was acidified with 2N hydrochloric acid, and diluted with water. The resulting solution was extracted with ethyl acetate (3×). The combined organic layer was washed with brine and dried over anhydrous sodium sulfate. The solvent was removed in vacuo to afford (S)-2-(8-chloro-3-oxo-3,9-dihydro-1H-chromeno[2,3-c]pyrrol-2-yl)-3-cyclohexyl-propionic acid (1.2 g, 83.3%).

Step 3

A solution of (S)-2-(8-chloro-3-oxo-3,9-dihydro-1H-chromeno[2,3-c]pyrrol-2-yl)-3-cyclohexyl-propionic acid (200 mg, 2.1 mmol), commercially available 2-aminopyridine (60 mg, 0.63 mmol), N-ethyl-N-dimethyaminopropyl carbodiimide hydrochloride (EDCI. HCl) (112 mg, 0.59 mmol), and N-hydroxybenzotriazole (HOBt) (79 mg, 0.59 mmol) in methylene chloride (10 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradiant elution, to afford (S)-2-(8-chloro-3-oxo-3,9-dihydro-1H-chromeno[2,3-c]pyrrol-2-yl)-3-cyclohexyl-N-pyridin-2-ylpropionamide (50 mg, 20.8%), as a white solid. $^1$H NMR (DMSO-$d_6$) δ: 10.87 (s, 1H), 8.28-8.41 (m, 1H), 8.00 (d, J=8.8 Hz, 1H), 7.70-7.86 (m, 1H), 7.20-7.40 (m, 2H), 7.03-7.16 (m, 2H), 5.09 (br. s., 1H), 5.00-5.01 (m, 1H), 4.36-4.37 (m, 1H), 4.43 (d, J=18.6 Hz, 1H), 4.07 (d, J=18.6 Hz, 3H), 3.99-4.15 (m, 1H), 3.75 (s, 2H), 1.49-1.90 (m, 6H), 1.05-1.29 (m, 4H), 0.88-1.02 (m, 2H).

Example 2

(S)-2-(8-Chloro-3-oxo-3,9-dihydro-1H-chromeno[2,3-c]pyrrol-2-yl)-3-cyclohexyl-N-thiazol-2-yl-propionamide

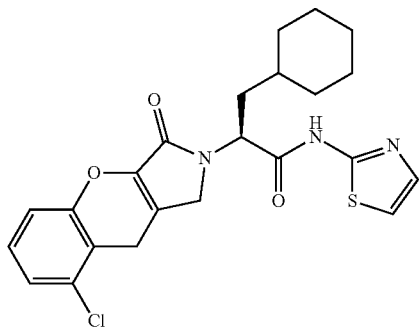

A solution of (S)-2-(8-chloro-3-oxo-3,9-dihydro-1H-chromeno[2,3-c]pyrrol-2-yl)-3-cyclohexyl-propionic acid (200 mg, 2.1 mmol) (from Example 1, Step 3), commercially available 2-aminothiazole (110 mg, 0.63 mmol), N-ethyl-N-dimethyaminopropyl carbodiimide hydrochloride (EDCI. HCl) (112 mg, 0.59 mmol), and N-hydroxybenzotriazole (HOBt) (79 mg, 0.59 mmol) in methylene chloride (10 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silical gel flash chromatography using hexane-ethyl acetate gradiant elution, afforded (S)-2-(8-Chloro-3-oxo-3,9-dihydro-1H-chromeno[2,3-c]pyrrol-2-yl)-3-cyclohexyl-N-thiazol-2-yl-propionamide (113 mg, 46.3%) as a white solid. $^1$H NMR (DMSO-$d_6$) δ: 12.56 (br. s., 1H), 7.50 (d, J=3.4 Hz, 3H), 7.20-7.36 (m, 10H), 7.05-7.15 (m, 3H), 5.06 (d, J=5.9 Hz, 3H), 4.40 (d, J=18.6 Hz, 3H), 4.09 (d, J=18.6 Hz, 3H), 3.76 (s, 6H), 1.52-1.91 (m, 24H), 1.04-1.32 (m, 17H), 0.90-1.03 (m, 7H), 0.79-0.88 (m, 3H).

Example 3

(S)-2-(8-Chloro-3-oxo-3,9-dihydro-1H-chromeno[2,3-c]pyrrol-2-yl)-4-methyl-pentanoic acid pyridin-2-ylamide

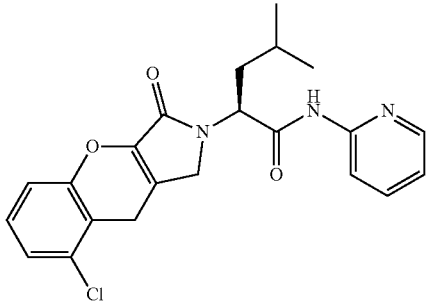

Step 1 a) To a solution of 5-chloro-3-formyl-2H-chromene-2-carboxylic acid ethyl ester (1.5 g, 5.62 mmol) (from Example 1, Step 1) in methanol (20 mL) containing molecular sieves (0.7 g) was added commercially available (S)-2-amino-4-methyl-pentanoic acid methyl ester (1.2 g, 5.62 mmol) and N,N'-diisopropylethylamine (2 mL, 11.24 mmol). The mixture was stirred at 25° C. for 10 hours. At this time, sodium cyanoborohydride (0.706 g, 11.24 mmol) and acetic acid (0.70 mL, 11.24 mmol) were added simultaneously to the reaction mixture, and the reaction mixture was stirred for additional 16 hours at 25° C. The reaction mixture was then filtered through celite and washed with methanol. The filtrate was concentrated in vacuo and the residue was purified using flash column chromatography over neutral alumina (eluant-ethyl acetate:petroleum ether 1:19, $R_f$=0.7) to afford 5-chloro-3-[((S)-1-methoxycarbonyl-3-methyl-butylamino)-methyl]-2H-chromene-2-carboxylic acid methyl ester (1.2 g, 54.5%) as an oil.

b) A solution of 5-chloro-3-[((S)-1-methoxycarbonyl-3-methyl-butylamino)-methyl]-2H-chromene-2-carboxylic acid methyl ester (1.4 g, 3.53 mmol) and N,N'-diisopropylethyl amine (2.44 mL, 14.14 mmol) in acetonitrile (3 mL) was heated in a sealed tube at 140° C. for 48 hours. The reaction mixture, after aqueous work-up, was extracted with ethyl acetate (3×). The combined ethyl acetate layer was washed with brine, and dried over anhydrous sodium sulfate. The organic layer was concentrated in vacuo and the residue was purified using flash chromatography over neutral alumina (eluant-hexanes-ethyl acetate 1:3, $R_f$=0.3) to afford (S)-2-[(5-chloro-2-formyl-2H-chromen-3-ylmethyl)-methyl-amino]-4-methyl-pentanoic acid methyl ester (1.02 g, 71.4%) as a solid.

c) A solution of (S)-2-[(5-chloro-2-formyl-2H-chromen-3-ylmethyl)-methyl-amino]-4-methyl-pentanoic acid methyl ester (2.0 g, 5.71 mmol) and lithium hydroxide monohydrate (0.312 g, 7.40 mmol) was stirred at 25° C. for 2 hours in tetrahydrofuran-water (3:1) mixture (90 mL). The reaction mixture was concentrated in vacuo to remove tetrahydrofuran, and the residue was acidified with 2N hydrochloric acid, and diluted with water. The resulting solution was extracted with ethyl acetate (3×). The combined organic layer was washed with brine and dried over anhydrous sodium sulfate. The solvent was removed in vacuo to afford (S)-2-[(5-chloro-2-formyl-4H-chromen-3-ylmethyl)-methyl-amino]-4-methyl-pentanoic acid (1.78 g, 93.6%).

Step 2

A solution of (S)-2-[(5-chloro-2-formyl-4H-chromen-3-ylmethyl)-methyl-amino]-4-methyl-pentanoic acid (300 mg, 2.1 mmol), commercially available 2-aminopyridine (101 mg, 1.07 mmol), N-ethyl-N-dimethyaminopropyl carbodiimide hydrochloride (EDCI. HCl) (190 mg, 0.98 mmol), and N-hydroxybenzotriazole (HOBt) (132 mg, 0.982 mmol) in methylene chloride (15 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradiant elution, to afford S)-2-(8-Chloro-3-oxo-3,9-dihydro-1H-chromeno[2,3-c]pyrrol-2-yl)-4-methyl-pentanoic acid pyridin-2-ylamide (970 mg, 26.4%), as a white solid. $^1$H NMR (DMSO-$d_6$) δ: 10.89 (s, 1H), 8.34 (d, J=3.9 Hz, 1H), 8.01 (d, J=7.8 Hz, 1H), 7.77 (t, J=7.3 Hz, 1H), 7.21-7.42 (m, 2H), 7.02-7.17 (m, 2H), 5.07 (d, J=4.9 Hz, 1H), 4.44 (d, J=18.6 Hz, 1H), 4.07 (d, J=18.6 Hz, 1H), 3.75 (s, 2H), 1.75-1.90 (m, 1H), 1.61-1.74 (m, 1H), 1.46 (br. s., 1H), 1.24 (s, 1H), 0.93 (t, J=5.9 Hz, 6H).

Example 4

(S)-2-(8-Chloro-3-oxo-3,9-dihydro-1H-chromeno[2,3-c]pyrrol-2-yl)-4-methyl-pentanoic acid (5-chloro-pyridin-2-yl)-amide

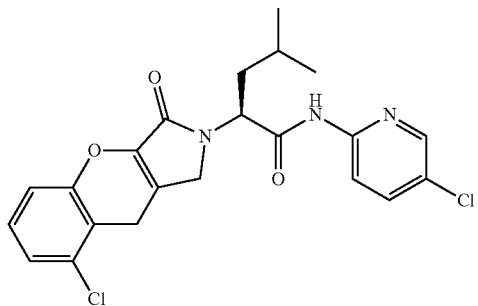

A solution of (S)-2-(8-chloro-3-oxo-3,9-dihydro-1H-chromeno[2,3-c]pyrrol-2-yl)-3-cyclohexyl-propionic acid (200 mg, 2.1 mmol) (from Example 3, Step 1c), in methylene chloride (10 mL) was treated with oxalyl chloride (0.12 mL, 1.07 mmol) at 0° C. The mixture was warmed to 25° C. and stirred for additional 2 hours. Then, the reaction mixture was cooled to 0° C., and N,N'-diisopropylethyl amine (0.61 mL, 3.57 mmol) and commercially available 5-chloro-pyridin-2-ylamine (137 mg, 1.07 mmol), were added. The reaction mixture was stirred for 16 hours at 25° C. The reaction mixture was diluted with water and extracted with ethyl acetate (2×). The combined organic layers were dried over anhydrous sodium sulfate and concentrated in vacuo. The resulting residue, upon silica gel flash chromatography using hexane-ethyl acetate gradiant elution, afforded (S)-2-(8-chloro-3-oxo-3,9-dihydro-1H-chromeno[2,3-c]pyrrol-2-yl)-4-methyl-pentanoic acid (5-chloro-pyridin-2-yl)-amide (145 mg, 36.3%), as a white solid. $^1$H NMR (DMSO-$d_6$) δ: 11.11 (s, 1H), 8.40 (d, J=2.4 Hz, 1H), 8.05 (d, J=8.8 Hz, 1H), 7.90 (dd, J=8.8, 2.4 Hz, 1H), 7.21-7.38 (m, 2H), 7.09 (dd, J=7.1, 2.2 Hz, 1H), 5.06 (dd, J=10.5, 4.6 Hz, 1H), 4.42 (d, J=18.6 Hz, 1H), 4.07 (d, J=19.1 Hz, 1H), 3.75 (s, 2H), 1.77-1.89 (m, 1H), 1.61-1.73 (m, 1H), 1.46 (br. s., 1H), 0.93 (t, J=6.4 Hz, 6H).

Example 5

(S)-2-(8-Chloro-3-oxo-3,9-dihydro-1H-chromeno[2,3-c]pyrrol-2-yl)-4-methyl-pentanoic acid thiazol-2-ylamide

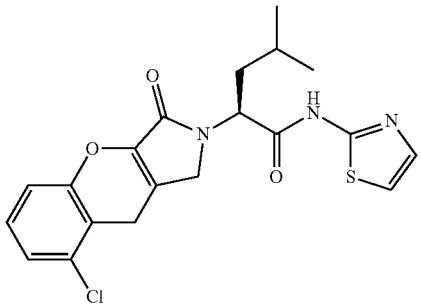

A solution of (S)-2-[(5-chloro-2-formyl-4H-chromen-3-ylmethyl)-methyl-amino]-4-methyl-pentanoic acid (300 mg, 2.1 mmol) (Example 3, Step 1c), commercially available 2-aminothiazole (109 mg, 1.07 mmol), N-ethyl-N-dimethyaminopropyl carbodiimide hydrochloride (EDCI. HCl) (190 mg, 0.98 mmol), and N-hydroxybenzotriazole (HOBt) (132 mg, 0.982 mmol) in methylene chloride (15 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded (S)-2-(8-chloro-3-oxo-3,9-dihydro-1H-chromeno[2,3-c]pyrrol-2-yl)-4-methyl-pentanoic acid thiazol-2-yl-amide (200 mg, 53%), as a light yellow solid. $^1$H NMR (DMSO-$d_6$) δ: 12.58 (br. s., 1H), 7.50 (d, J=3.4 Hz, 1H), 7.19-7.36 (m, 3H), 7.09 (dd, J=7.1, 2.2 Hz, 1H), 5.05 (dd, J=10.8, 4.9 Hz, 1H), 4.40 (d, J=19.1 Hz, 1H), 4.09 (d, J=18.6 Hz, 1H), 3.76 (br. s., 2H), 1.78-1.92 (m, 1H), 1.63-1.76 (m, 1H), 1.46 (br. s., 1H), 0.93 (t, J=7.1 Hz, 6H).

Example 6

6-[(S)-2-(8-Chloro-3-oxo-3,9-dihydro-1H-chromeno[2,3-c]pyrrol-2-yl)-4-methyl-pentanoylamino]-nicotinic acid methyl ester

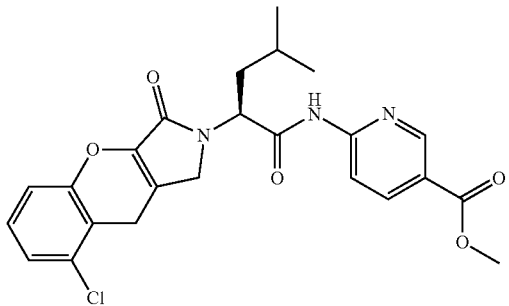

A solution of (S)-2-[(5-chloro-2-formyl-4H-chromen-3-ylmethyl)-methyl-amino]-4-methyl-pentanoic acid (300 mg, 2.1 mmol) (Example 3, Step 1), commercially available 6-amino-nicotinic acid methyl ester (163 mg, 1.07 mmol), N-ethyl-N-dimethyaminopropyl carbodiimide hydrochloride (EDCI. HCl) (190 mg, 0.98 mmol), and N-hydroxybenzotriazole (HOBt) (132 mg, 0.982 mmol) in methylene chloride (15 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded 6-[(S)-2-(8-chloro-3-oxo-3,9-dihydro-1H-chromeno[2,3-c]pyrrol-2-yl)-4-methyl-pentanoylamino]-nicotinic acid methyl ester (143 mg, 3%), as a white solid. $^1$H NMR (DMSO-$d_6$) δ: 11.36 (s, 1H), 8.87 (s, 1H), 8.29 (dd, J=8.8, 2.0 Hz, 1H), 8.15 (d, J=8.8 Hz, 1H), 7.18-7.39 (m, 2H), 7.09 (dd, J=6.8, 2.0 Hz, 1H), 5.09 (dd, J=10.8, 4.4 Hz, 1H), 4.43 (d, J=19.1 Hz, 1H), 4.08 (d, J=19.1 Hz, 1H), 3.86 (s, 3H), 3.75 (s, 2H), 1.78-1.92 (m, 1H), 1.63-1.76 (m, 1H), 1.47 (br. s., 1H), 0.93 (t, J=5.9 Hz, 6H).

Example 7

(S)-3-Cyclohexyl-2-(8-methoxy-3-oxo-3,9-dihydro-1H-chromeno[2,3-c]pyrrol-2-yl)-N-pyridin-2-yl-propionamide

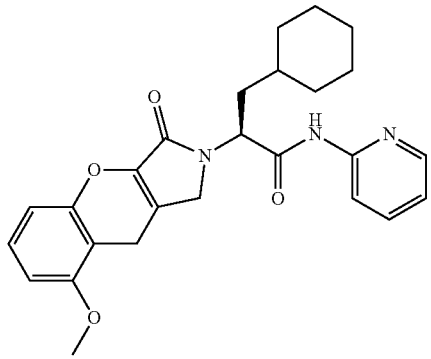

Step 1

(E)-4-oxo-but-2-enoic acid ethyl ester (7.63 mL, 63.09 mmol), 2-nitro benzoic acid (1.77 g, 10.52 mmol), and pyrrolidine (0.87 mL, 10.52 mmol) were added simultaneously to a solution of commercially available 2-hydroxy-6-methoxy-benzaldehyde (8.0 g, 52.58 mmol) in dimethysulfoxide (50 mL) at 25° C. and the solution was stirred for 78 hours at 25° C. The reaction was quenched by the addition of water. The reaction mixture was then partitioned between water and ethyl acetate. The combined organics were washed with a saturated brine solution, dried over anhydrous sodium sulfate, filtered, rinsed and concentrated in vacuo. The residue obtained was purified on a silica gel flash column chromatography using ethyl acetate-hexanes as eluants, yielding 5-methoxy-3-formyl-2H-chromene-2-carboxylic acid ethyl ester as a solid (1.80 g, 51.9%).

Step 2 a) To a solution of 5-methoxy-3-formyl-2H-chromene-2-carboxylic acid ethyl ester (1.3 g, 4.96 mmol) in methanol (20 mL) containing molecular sieves (0.7 g) was added commercially available (S)-2-amino-3-cyclohexyl-propionic acid methyl ester (1.2 g, 5.45 mmol) and N,N'-diisopropylethylamine (1.71 mL, 9.91 mmol). The mixture was stirred at 25° C. for 10 hours. At this time, sodium cyanoborohydride (0.62 g, 9.91 mmol) and acetic acid (0.47 mL, 7.49 mmol) were added simultaneously to the reaction mixture, and the reaction mixture was stirred for additional 16 hours at 25° C. The reaction mixture was then filtered through celite and washed with methanol. The filtrate was concentrated in vacuo. Flash column chromatography (eluant-ethyl acetate:petroleum ether 1:19, $R_f$=0.6) over neutral alumina afforded 5-methoxy-3-[((S)-2-cyclohexyl-1-methoxycarbonyl-ethylamino)-methyl]-2H-chromene-2-carboxylic acid ethyl ester (1.0 g, 45.5%) as an oil.

b) A solution of 5-methoxy-3-[((S)-2-cyclohexyl-1-methoxycarbonyl-ethylamino)-methyl]-2H-chromene-2-carboxylic acid ethyl ester (1.0 g, 2.32 mmol) and N,N'-diisopropylethyl amine (1.60 mL, 9.27 mmol) in acetonitrile (2 mL) was heated in a sealed tube at 140° C. for 48 h. The reaction mixture, after aqueous work-up, was extracted with ethyl acetate (3×). The combined ethyl acetate layer was washed with brine, and dried over anhydrous sodium sulfate. The organic layer was concentrated in vacuo and the residue was purified over neutral alumina using hexanes-ethyl acetate as eluents to afford (S)-2-(8-methoxy-3-oxo-3,3a-dihydro-1H-chromeno[2,3-c]pyrrol-2-yl)-3-cyclohexyl-propionic acid methyl ester (0.25 g, 87.3%) as a solid.

c) A solution of (S)-2-(8-methoxy-3-oxo-3,3a-dihydro-1H-chromeno[2,3-c]pyrrol-2-yl)-3-cyclohexyl-propionic acid methyl ester (1.2 g, 3.13 mmol) and lithium hydroxide monohydrate (0.17 g, 4.04 mmol) was stirred at 25° C. for 2 hours in tetrahydrofuran-water (3:1) mixture (20 mL). The reaction mixture was concentrated in vacuo to remove tetrahydrofuran, and the residue was acidified with 2N hydrochloric acid, and diluted with water. The resulting solution was extracted with ethyl acetate (3×). The combined organic layer was washed with brine and dried over anhydrous sodium sulfate. The solvent was removed in vacuo to afford (S)-2-(8-methoxy-3-oxo-3,9-dihydro-1H-chromeno[2,3-c]pyrrol-2-yl)-3-cyclohexyl-propionic acid (1.1 g, 95.7%).

Step 3

A solution of (S)-2-(8-methoxy-3-oxo-3,9-dihydro-1H-chromeno[2,3-c]pyrrol-2-yl)-3-cyclohexyl-propionic acid (200 mg, 0.64 mmol), in methylene chloride (10 mL) was treated with oxalyl chloride (0.07 mL, 0.64 mmol) at 0° C. The mixture was warmed to 25° C. and stirred for additional 2 hours. Then, the reaction mixture was cooled to 0° C., and N,N'-diisopropylethyl amine (0.34 mL, 1.92 mmol) and commercially available 2-amino-pyridine (68 mg, 0.64 mmol), were added. The reaction mixture was stirred for 16 hours at 25° C. The reaction mixture was diluted with water and extracted with ethyl acetate (2×). The combined organic layers were dried over anhydrous sodium sulfate and concentrated in vacuo. The resulting residue, upon silica gel flash chromatography using hexane-ethyl acetate gradiant elution, afforded (S)-3-cyclohexyl-2-(8-methoxy-3-oxo-3,9-dihydro-1H-chromeno[2,3-c]pyrrol-2-yl)-N-pyridin-2-yl-propionamide (42 mg, 17.4%), as a white solid. $^1$H NMR (DMSO-$d_6$) δ: 10.85 (s, 1H), 8.33 (d, J=3.9 Hz, 1H), 8.00 (d, J=8.3 Hz, 1H), 7.77 (t, J=7.3 Hz, 1H), 7.22 (t, J=8.3 Hz, 1H), 7.12 (t, J=5.9 Hz, 1H), 6.77 (d, J=7.8 Hz, 1H), 6.68 (d, J=8.3 Hz, 1H), 5.08 (br. s., 1H), 4.39 (d, J=18.6 Hz, 1H), 4.03 (d, J=19.1 Hz, 1H), 3.82 (s, 3H), 3.55 (s, 2H), 1.49-1.88 (m, 7H), 0.85-1.32 (m, 6H).

Example 8

(S)—N-(5-Chloro-pyridin-2-yl)-3-cyclohexyl-2-(8-methoxy-3-oxo-3,9-dihydro-1H-chromeno[2,3-c]pyrrol-2-yl)-propionamide

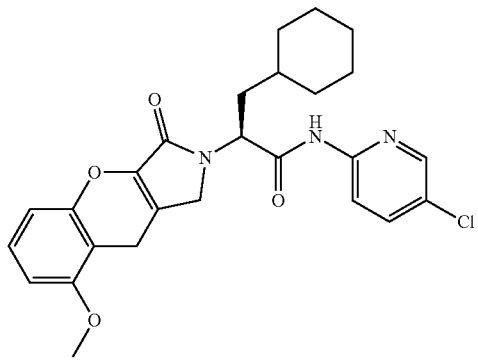

A solution of (S)-2-(8-methoxy-3-oxo-3,9-dihydro-1H-chromeno[2,3-c]pyrrol-2-yl)-3-cyclohexyl-propionic acid (200 mg, 0.64 mmol) (from Example 7, Step 2c), in methylene chloride (10 mL) was treated with oxalyl chloride (0.07 mL, 0.64 mmol) at 0° C. The mixture was warmed to 25° C. and stirred for additional 2 hours. Then, the reaction mixture was cooled to 0° C., and N,N'-diisopropylethyl amine (0.34 mL, 1.92 mmol) and commercially available 5-chloro-pyridin-2-ylamine (83 mg, 0.64 mmol), were added. The reaction mixture was stirred for 16 hours at 25° C. The reaction mixture was diluted with water and extracted with ethyl acetate (2×). The combined organic layers were dried over anhydrous sodium sulfate and concentrated in vacuo. The resulting residue, upon silica gel flash chromatography using hexane-ethyl acetate gradiant elution, afforded (S)—N-(5-chloro-pyridin-2-yl)-3-cyclohexyl-2-(8-methoxy-3-oxo-3,9-dihydro-1H-chromeno[2,3-c]pyrrol-2-yl)-propionamide (68 mg, 26.3%), as a white solid. $^1$H NMR (DMSO-$d_6$) δ: 11.07 (s, 1H), 8.39 (s, 1H), 8.04 (d, J=8.8 Hz, 1H), 7.90 (d, J=8.8 Hz, 1H), 7.22 (t, J=8.3 Hz, 1H), 6.77 (d, J=8.3 Hz, 1H), 6.68 (d, J=8.3 Hz, 1H), 5.07 (d, J=5.9 Hz, 1H), 4.37 (d, J=18.6 Hz, 1H), 4.03 (d, J=19.1 Hz, 1H), 3.82 (s, 3H), 3.55 (s, 2H), 1.48-2.00 (m, 7H), 0.85-1.32 (m, 6H).

Example 9

(S)-3-Cyclohexyl-2-(8-methoxy-3-oxo-3,9-dihydro-1H-chromeno[2,3-c]pyrrol-2-yl)-N-thiazol-2-yl-propionamide

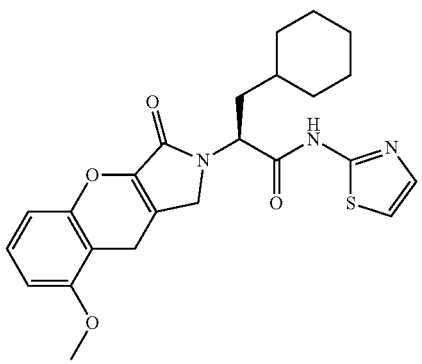

A solution of (S)-2-(8-methoxy-3-oxo-3,9-dihydro-1H-chromeno[2,3-c]pyrrol-2-yl)-3-cyclohexyl-propionic acid (200 mg, 0.54 mmol) (Example 7, Step 2c), commercially available 2-amino-thiazole (66 mg, 0.64 mmol), N-ethyl-N-dimethyaminopropyl carbodiimide hydrochloride (EDCI.HCl) (113 mg, 0.59 mmol), and N-hydroxybenzotriazole (HOBt) (80 mg, 0.59 mmol) in methylene chloride (10 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded (S)-3-Cyclohexyl-2-(8-methoxy-3-oxo-3,9-dihydro-1H-chromeno[2,3-c]pyrrol-2-yl)-N-thiazol-2-yl-propionamide (68 mg, 27.9%), as an off white solid. $^1$H NMR (DMSO-$d_6$) δ: 12.56 (br. s., 1H), 7.49 (d, J=3.4 Hz, 1H), 7.11-7.31 (m, 2H), 6.77 (d, J=7.8 Hz, 1H), 6.68 (d, J=8.3 Hz, 1H), 5.05 (d, J=5.4 Hz, 1H), 4.36 (d, J=19.1 Hz, 1H), 4.05 (d, J=18.6 Hz, 1H), 3.82 (s, 3H), 3.55 (br. s., 2H), 1.47-1.89 (m, 7H), 0.78-1.29 (m, 6H).

Example 10

6-[(S)-3-Cyclohexyl-2-(8-methoxy-3-oxo-3,9-dihydro-1H-chromeno[2,3-c]pyrrol-2-yl)-propionylamino]-nicotinic acid methyl ester

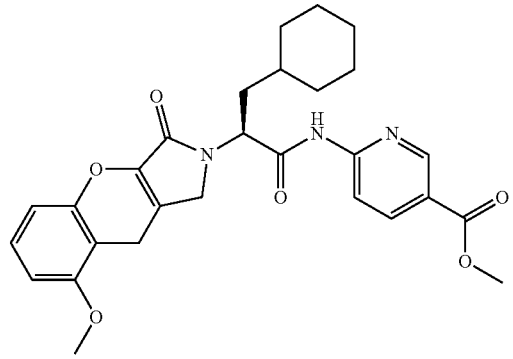

A solution of (S)-2-(8-methoxy-3-oxo-3,9-dihydro-1H-chromeno[2,3-c]pyrrol-2-yl)-3-cyclohexyl-propionic acid (200 mg, 0.54 mmol) (Example 7, Step 2c), commercially available 6-amino-nicotinic acid methyl ester (98 mg, 0.64 mmol), N-ethyl-N-dimethyaminopropyl carbodiimide hydrochloride (EDCI. HCl) (113 mg, 0.59 mmol), and N-hydroxybenzotriazole (HOBt) (80 mg, 0.59 mmol) in methylene chloride (10 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded 6-[(S)-3-cyclohexyl-2-(8-methoxy-3-oxo-3,9-dihydro-1H-chromeno[2,3-c]pyrrol-2-yl)-propionylamino]-nicotinic acid methyl ester (50 mg, 18.4%), as a white solid. $^1$H NMR (DMSO-$d_6$) δ: 11.32 (br. s., 1H), 8.87 (br. s., 1H), 8.28 (d, J=8.8 Hz, 1H), 8.14 (d, J=8.3 Hz, 1H), 7.22 (t, J=8.1 Hz, 1H), 6.76 (d, J=7.8 Hz, 1H), 6.68 (d, J=8.3 Hz, 1H), 5.10 (br. s., 1H), 4.38 (d, J=18.6 Hz, 1H), 4.04 (d, J=19.1 Hz, 1H), 3.84 (d, J=15.7 Hz, 6H), 3.55 (br. s., 2H), 1.48-1.89 (m, 7H), 0.85-1.29 (m, 6H).

Example 11

(S)-2-(8-Methoxy-3-oxo-3,9-dihydro-1H-chromeno[2,3-c]pyrrol-2-yl)-4-methyl-pentanoic acid thiazol-2-ylamide

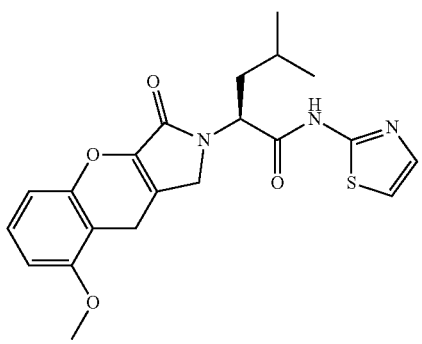

Step 1 a) To a solution of 5-methoxy-3-formyl-2H-chromene-2-carboxylic acid ethyl ester (Example 7, step 1) (1.0 g, 3.81 mmol) in methanol (20 mL) containing molecular sieves (0.7 g) was added commercially available (S)-2-amino-4-methyl-pentanoic acid methyl ester (0.77 g, 6.86 mmol) and N,N'-diisopropylethylamine (0.99 mL, 7.63 mmol). The mixture was stirred at 25° C. for 10 hours. At this time, sodium cyanoborohydride (0.48 g, 7.63 mmol) and acetic acid (0.8 mL, 13.72 mmol) were added simultaneously to the reaction mixture, and the reaction mixture was stirred for additional 16 hours at 25° C. The reaction mixture was then filtered through celite and washed with methanol. The filtrate was concentrated in vacuo. Flash column chromatography (eluant-ethyl acetate:petroleum ether 1:9, $R_f$=0.45) over neutral alumina afforded 5-methoxy-3-[((S)-1-methoxycarbonyl-3-methyl-butylamino)-methyl]-2H-chromene-2-carboxylic acid ethyl ester (0.45 g, 43.3%) as an oil.

b) A solution of 5-methoxy-3-[((S)-1-methoxycarbonyl-3-methyl-butylamino)-methyl]-2H-chromene-2-carboxylic acid ethyl ester (0.45 g, 1.14 mmol) and N,N'-diisopropylethyl amine (0.8 mL, 4.50 mmol) in acetonitrile (2 mL) was heated in a sealed tube at 140° C. for 48 hours. The reaction mixture, after aqueous work-up, extracted with ethyl acetate (3×). The combined ethyl acetate layer was washed with brine, and dried over anhydrous sodium sulfate. The organic layer was concentrated in vacuo and the residue was purified over neutral alumina using hexanes-ethyl acetate as eluents to afford (S)-2-(8-methoxy-3-oxo-3,3a-dihydro-1H-chromeno[2,3-c]pyrrol-2-yl)-4-methyl-pentanoic acid methyl ester (0.25 g, 62.9%) as a solid.

a) A solution of (S)-2-(8-methoxy-3-oxo-3,3a-dihydro-1H-chromeno[2,3-c]pyrrol-2-yl)-4-methyl-pentanoic acid methyl ester (0.75 g, 2.17 mmol) and lithium hydroxide monohydrate (0.12 g, 2.82 mmol) was stirred at 25° C. for 2 hours in tetrahydrofuran-water (3:1) mixture (30 mL). The reaction mixture was concentrated in vacuo to remove tetrahydrofuran, and the residue was acidified with 2N hydrochloric acid, and diluted with water. The resulting solution was extracted with ethyl acetate (3×). The combined organic layer was washed with brine and dried over anhydrous sodium sulfate. The solvent was removed in vacuo to afford (S)-2-(8-methoxy-3-oxo-3,9-dihydro-1H-chromeno[2,3-c]pyrrol-2-yl)-4-methyl-pentanoic acid (0.52 g, 72.3%).

Step 2

A solution of (S)-2-(8-methoxy-3-oxo-3,9-dihydro-1H-chromeno[2,3-c]pyrrol-2-yl)-4-methyl-pentanoic acid (100 mg, 0.30 mmol), commercially available 2-amino-thiazole (37 mg, 0.36 mmol), N-ethyl-N-dimethyaminopropyl carbodiimide hydrochloride (EDCI. HCl) (66 mg, 0.33 mmol), and N-hydroxybenzotriazole (HOBt) (44 mg, 0.33 mmol) in methylene chloride (10 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded (S)-2-(8-methoxy-3-oxo-3,9-dihydro-1H-chromeno[2,3-c]pyrrol-2-yl)-4-methyl-pentanoic acid thiazol-2-ylamide (34 mg, 27.2%), as an off white solid. $^1$H NMR (DMSO-$d_6$) δ: 12.58 (br. s., 1H), 7.50 (d, J=3.4 Hz, 1H), 7.12-7.34 (m, 2H), 6.76 (d, J=7.8 Hz, 1H), 6.68 (d, J=8.3 Hz, 1H), 5.04 (d, J=5.9 Hz, 1H), 4.36 (d, J=19.1 Hz, 1H), 4.05 (d, J=18.6 Hz, 1H), 3.82 (s, 3H), 3.55 (br. s., 2H), 1.83 (d, J=9.3 Hz, 1H), 1.68 (br. s., 1H), 1.45 (br. s., 1H), 0.93 (t, J=7.3 Hz, 6H).

Example 12

6-[(S)-2-(8-Methoxy-3-oxo-3,9-dihydro-1H-chromeno[2,3-c]pyrrol-2-yl)-4-methyl-pentanoylamino]-nicotinic acid methyl ester

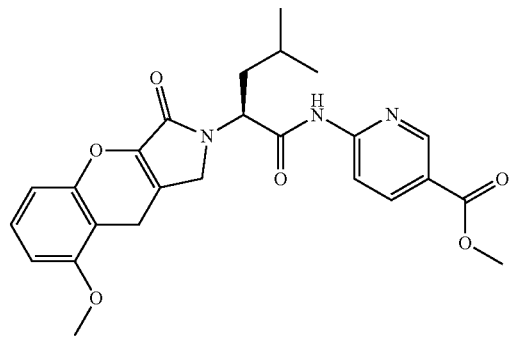

A solution of (S)-2-(8-methoxy-3-oxo-3,9-dihydro-1H-chromeno[2,3-c]pyrrol-2-yl)-4-methyl-pentanoic acid (Example 11, step 1c) (100 mg, 0.30 mmol), commercially available 6-amino-nicotinic acid methyl ester (55 mg, 0.36 mmol), N-ethyl-N-dimethyaminopropyl carbodiimide hydrochloride (EDCI. HCl) (66 mg, 0.33 mmol), and N-hydroxybenzotriazole (HOBt) (44 mg, 0.33 mmol) in methylene chloride (10 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded (S)-2-(8-methoxy-3-oxo-3,9-dihydro-1H-chromeno[2,3-c]pyrrol-2-yl)-4-methyl-pentanoic acid thiazol-2-ylamide (18 mg, 12.8%), as an off white solid. $^1$H NMR (DMSO-d$_6$) δ: 11.36 (br. s., 1H), 8.87 (br. s., 1H), 8.06-8.41 (m, 2H), 7.22 (br. s., 1H), 6.61-6.89 (m, 1H), 7.21 (m, 1H), 5.08 (br. s., 1H), 4.39 (d, J=17.1 Hz, 1H), 4.04 (d, J=19.1 Hz, 1H), 3.84 (d, J=16.6 Hz, 6H), 3.54 (br. s., 2H), 1.84 (m, 1H), 1.69 (m, 1H), 1.23 (br. s., 1H), 0.93 (br. s., 6H).

Example 13

(S)-3-Cyclohexyl-2-(5,8-dimethoxy-3-oxo-3,9-dihydro-1H-chromeno[2,3-c]pyrrol-2-yl)-N-pyridin-2-yl-propionamide

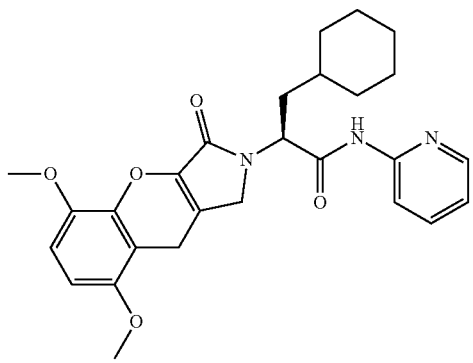

Step 1

(E)-4-oxo-but-2-enoic acid ethyl ester (7.30 mL, 60.37 mmol), 2-nitro benzoic acid (1.852 g, 10.98 mmol), and pyrrolidine (0.91 mL, 10.98 mmol) were added simultaneously to a solution of commercially available 2-hydroxy-3,6-dimethoxy-benzaldehyde (10.0 g, 54.89 mmol) in dimethysulfoxide (50 mL) at 25° C. and the solution was stirred for 78 hours at 25° C. The reaction was quenched by the addition of water. The reaction mixture was then partitioned between water and ethyl acetate. The combined organics were washed with a saturated brine solution, dried over anhydrous sodium sulfate, filtered, rinsed and concentrated in vacuo. The residue obtained was purified on a silica gel flash column chromatography using ethyl acetate-hexanes (1:1.2) as eluents, yielding 3-formyl-5,8-dimethoxy-2H-chromene-2-carboxylic acid ethyl ester (3.5 g, 62.3%).

Step 2 a) To a solution of 3-formyl-5,8-dimethoxy-2H-chromene-2-carboxylic acid ethyl ester (2.0 g, 6.48 mmol) in methanol (40 mL) containing molecular sieves (0.7 g) was added commercially available (S)-2-amino-3-cyclohexyl-propionic acid methyl ester (1.51 g, 6.84 mmol) and N,N'-diisopropylethylamine (1.76 mL, 13.68 mmol). The mixture was stirred at 25° C. for 10 hours. At this time, sodium cyanoborohydride (0.86 g, 13.68 mmol) and acetic acid (0.78 mL, 13.68 mmol) were added simultaneously to the reaction mixture, and the reaction mixture was stirred for additional 16 hours at 25° C. The reaction mixture was then filtered through celite and washed with methanol. The filtrate was concentrated in vacuo. Flash column chromatography (eluant-ethyl acetate: petroleum ether 1:19, R$_f$=0.6) over neutral alumina afforded 3-[((S)-2-cyclohexyl-1-methoxycarbonyl-ethylamino)-methyl]-5,8-dimethoxy-2H-chromene-2-carboxylic acid methyl ester (1.2 g, 37.5%) as an oil.

A solution of 3-[((S)-2-cyclohexyl-1-methoxycarbonyl-ethylamino)-methyl]-5,8-dimethoxy-2H-chromene-2-carboxylic acid methyl ester (1.2 g, 4.10 mmol) and N,N'-diisopropylethyl amine (2.83 mL, 16.42 mmol) in acetonitrile (3 mL) was heated in a sealed tube at 140° C. for 48 hours. The reaction mixture, after aqueous work-up, extracted with ethyl acetate (3×). The combined ethyl acetate layer was washed with brine, and dried over anhydrous sodium sulfate. The organic layer was concentrated in vacuo and the residue was purified over neutral alumina using hexanes-ethyl acetate (1:1.2) as eluents to afford (S)-2-(5,8-dimethoxy-3-oxo-3,3a-dihydro-1H-chromeno[2,3-c]pyrrol-2-yl)-4-methyl-pentanoic acid methyl ester (0.6 g, 55.5%) as a solid.

c) A solution of (S)-2-(5,8-dimethoxy-3-oxo-3,3a-dihydro-1H-chromeno[2,3-c]pyrrol-2-yl)-4-methyl pentanoic acid methyl ester (0.58 g, 1.39 mmol) and lithium hydroxide monohydrate (0.64 g, 5.22 mmol) was stirred at 25° C. for 2 hours in tetrahydrofuran-water (3:1) mixture (25 mL). The reaction mixture was concentrated in vacuo to remove tetrahydrofuran, and the residue was acidified with 2N hydrochloric acid, and diluted with water. The resulting solution was extracted with ethyl acetate (3×). The combined organic layer was washed with brine and dried over anhydrous sodium sulfate. The solvent was removed in vacuo to afford (S)-3-cyclohexyl-2-(5,8-dimethoxy-3-oxo-3,9-dihydro-1H-chromeno[2,3-c]pyrrol-2-yl)-propionic acid (0.4 g, 71.4%).

Step 3

A solution of (S)-3-cyclohexyl-2-(5,8-dimethoxy-3-oxo-3,9-dihydro-1H-chromeno[2,3-c]pyrrol-2-yl)-propionic acid (100 mg, 0.24 mmol), in tetrahydrofuran (5 mL) was treated with N-methylmorpholine (70 mg, 0.56 mmol), 2-(1H-7-azabenzotriazol-1-yl)-1,1,3,3-tetramethyl uronium hexafluorophosphate (HATU) (212 mg, 0.56 mmol) and commercially available 2-aminopyridine (25 mg, 0.26 mmol). The mixture was heated in a sealed tube was heated for 16 hours at 90° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded (S)-3-cyclohexyl-2-(5,8-dimethoxy-3-oxo-3,9-dihydro-1H-chromeno[2,3-c]pyrrol-2-yl)-N-pyridin-2-yl-propionamide (19 mg, 17.8%), as a white solid. $^1$H NMR (DMSO-d$_6$) δ: 10.83 (br. s., 1H), 8.34 (br. s., 1H), 8.00 (d, J=7.8 Hz, 1H), 7.77 (br. s., 1H), 7.12 (br. s., 1H), 6.92 (d, J=8.8 Hz, 1H), 6.67 (d, J=8.8 Hz, 1H), 5.09 (br. s., 1H), 4.39 (d, J=18.6 Hz, 1H), 4.02 (d, J=19.1 Hz, 1H), 3.76 (s, 6H), 3.55 (br. s., 2H), 1.50-1.89 (m, 7H), 0.87-1.28 (m, 6H).

Example 14

(S)-2-(5,8-Dimethoxy-3-oxo-3,9-dihydro-1H-chromeno[2,3-c]pyrrol-2-yl)-4-methyl-pentanoic acid (5-chloro-pyridin-2-yl)-amide

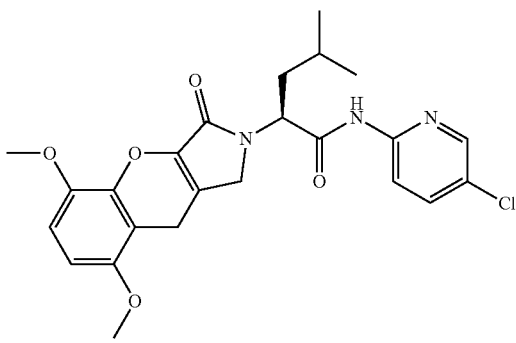

Step 1

To a solution of 3-formyl-5,8-dimethoxy-2H-chromene-2-carboxylic acid ethyl ester (5.0 g, 17.11 mmol) (Example 13, Step 1) in methanol (40 mL) containing molecular sieves (0.7 g) was added commercially available (S)-2-amino-4-methyl-pentanoic acid methyl ester (3.1 g, 17.11 mmol) and N,N'-diisopropylethylamine (4.42 mL, 34.21 mmol). The mixture was stirred at 25° C. for 10 hours. At this time, sodium cyanoborohydride (2.15 g, 34.21 mmol) and acetic acid (1.95 mL, 34.21 mmol) were added simultaneously to the reaction mixture, and the reaction mixture was stirred for additional 16 hours at 25° C. The reaction mixture was then filtered through celite and washed with methanol. The filtrate was concentrated in vacuo. Flash column chromatography (eluant-ethyl acetate:petroleum ether 1:19, $R_f$=0.6) over neutral alumina afforded 5,8-dimethoxy-3-[((S)-1-methoxycarbonyl-3-methyl-butylamino)-methyl]-2H chromene-2-carboxylic acid methyl ester (2.90 g, 39.2%) as an oil.

b) A solution of 5,8-dimethoxy-3-[((S)-1-methoxycarbonyl-3-methyl-butylamino)-methyl]-2H-chromene-2-carboxylic acid ethyl ester (3.0 g, 7.12 mmol) and N,N'-diisopropylethylamine (5.1 mL, 28.5 mmol) in acetonitrile (4 mL) was heated in a sealed tube at 140° C. for 48 h. The reaction mixture, after aqueous work-up, was extracted with ethyl acetate (3×). The combined ethyl acetate layer was washed with brine, and dried over anhydrous sodium sulfate. The organic layer was concentrated in vacuo and the residue was purified over neutral alumina using hexanes-ethyl acetate (1:1.2) as eluents to afford (S)-2-(5,8-dimethoxy-3-oxo-3,9-dihydro-1H-chromeno[2,3-c]pyrrol-2-yl)-4-methyl-pentanoic acid methyl ester (1.4 g, 53.8%) as a solid.

c) A solution of (S)-2-(5,8-dimethoxy-3-oxo-3,9-dihydro-1H-chromeno[2,3-c]pyrrol-2-yl)-4-methyl-pentanoic acid methyl ester (1.4 g, 1.39 mmol) and lithium hydroxide monohydrate (0.18 g, 4.26 mmol) was stirred at 25° C. for 2 hours in tetrahydrofuran-water (3:1) mixture (30 mL). The reaction mixture was concentrated in vacuo to remove tetrahydrofuran, and the residue was acidified with 2N hydrochloric acid, and diluted with water. The resulting solution was extracted with ethyl acetate (3×). The combined organic layer was washed with brine and dried over anhydrous sodium sulfate. The solvent was removed in vacuo to afford (S)-2-(5,8-dimethoxy-3-oxo-3,9-dihydro-1H-chromeno[2,3-c]pyrrol-2-yl)-4-methyl-pentanoic acid (1.23 g, 89.5%).

Step 2

A solution of (S)-2-(5,8-dimethoxy-3-oxo-3,9-dihydro-1H-chromeno[2,3-c]pyrrol-2-yl)-4-methyl-pentanoic acid (100 mg, 0.24 mmol), in tetrahydrofuran (10 mL) was treated with N-methylmorpholine (760 mg, 0.69 mmol), 2-(1H-7-azabenzotriazol-1-yl)-1,1,3,3-tetramethyl uronium hexafluorophosphate (HATU) (263 mg, 0.69 mmol) and commercially available 2-amino-5-chloropyridine (42 mg, 0.33 mmol). The mixture was heated in a sealed tube was heated for 16 hours at 90° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded (S)-2-(5,8-dimethoxy-3-oxo-3,9-dihydro-1H-chromeno[2,3-c]pyrrol-2-yl)-4-methyl-pentanoic acid (5-chloro-pyridin-2-yl)-amide (21 mg, 16.2%), as an off white solid. $^1$H NMR (DMSO-$d_6$) δ: 11.09 (br. s., 1H), 8.40 (br. s., 1H), 8.05 (d, J=8.8 Hz, 1H), 7.90 (d, J=8.8 Hz, 1H), 6.91 (d, J=8.8 Hz, 1H), 6.66 (d, J=8.8 Hz, 1H), 5.05 (br. s., 1H), 4.38 (d, J=19.1 Hz, 1H), 4.03 (d, J=18.6 Hz, 1H), 3.76 (s, 6H), 3.55 (br. s., 2H), 1.82 (br. s., 1H), 1.67 (br. s., 1H), 1.45 (br. s., 1H), 0.93 (t, J=6.1 Hz, 6H).

Example 15

(S)—N-(5-Chloro-pyridin-2-yl)-3-cyclohexyl-2-(5,8-dimethoxy-3-oxo-3,9-dihydro-1H-chromeno[2,3-c]pyrrol-2-yl)-propionamide

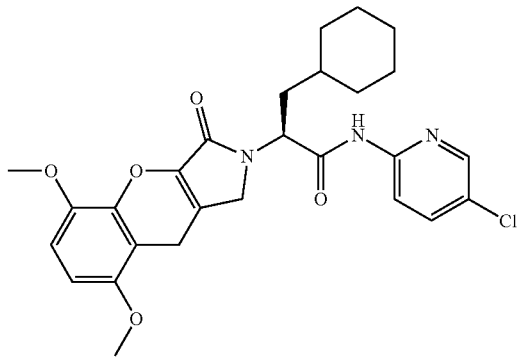

A solution of (S)-2-(5,8-dimethoxy-3-oxo-3,9-dihydro-1H-chromeno[2,3-c]pyrrol-2-yl)-4-methyl-pentanoic acid (Example 13, step 2c) (100 mg, 0.24 mmol), in tetrahydrofuran (10 mL) was treated with N-methylmorpholine (100 mg, 0.74 mmol), 2-(1H-7-azabenzotriazol-1-yl)-1,1,3,3-tetramethyl uronium hexafluorophosphate (HATU) (284 mg, 0.74 mmol) and commercially available 2-amino-5-chloropyridine (38 mg, 0.29 mmol). The mixture was heated in a sealed tube was heated for 16 hours at 90° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded ((S)—N-(5-chloro-pyridin-2-yl)-3-cyclohexyl-2-(5,8-dimethoxy-3-oxo-3,9-dihydro-1H-chromeno[2,3-c]pyrrol-2-yl)-propionamide (31 mg, 24.4%), as a white solid. $^1$H NMR (DMSO-$d_6$) δ: 11.05 (br. s., 1H), 8.39 (br. s., 1H), 8.04 (d, J=8.3 Hz, 1H), 7.89 (d, J=8.8 Hz, 1H), 6.91 (d, J=8.8 Hz, 1H), 6.66 (d, J=8.8 Hz, 1H), 5.08 (d, J=5.9 Hz, 1H), 4.37 (d, J=19.1 Hz, 1H), 4.02 (d, J=18.6 Hz, 1H), 3.76 (s, 6H), 3.55 (br. s., 2H), 1.53-1.85 (m, 7H), 0.75-1.29 (m, 6H).

Example 16

(S)-3-Cyclohexyl-2-(5,8-dimethoxy-3-oxo-3,9-dihydro-1H-chromeno[2,3-c]pyrrol-2-yl)-N-thiazol-2-yl-propionamide

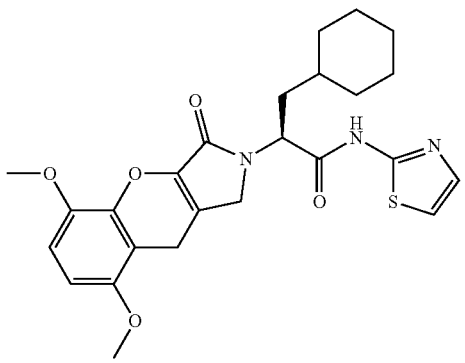

A solution of (S)-2-(5,8-dimethoxy-3-oxo-3,9-dihydro-1H-chromeno[2,3-c]pyrrol-2-yl)-4-methyl-pentanoic acid (Example 13, step 2c) (100 mg, 0.21 mmol), commercially available 2-aminothiazole (30 mg, 0.30 mmol), N-ethyl-N-dimethyaminopropyl carbodiimide hydrochloride (EDCI. HCl) (52 mg, 0.27 mmol), and N-hydroxybenzotriazole (HOBt) (37 mg, 0.27 mmol) in methylene chloride (10 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded (S)-3-cyclohexyl-2-(5,8-dimethoxy-3-oxo-3,9-dihydro-1H-chromeno[2,3-c]pyrrol-2-yl)-N-thiazol-2-yl-propionamide (68 mg, 56.6%), as a white solid. $^1$H NMR (DMSO-$d_6$) δ: 12.55 (br. s., 1H), 7.50 (d, J=2.9 Hz, 1H), 7.25 (br. s., 1H), 6.92 (d, J=8.8 Hz, 1H), 6.67 (d, J=8.8 Hz, 1H), 5.06 (d, J=5.4 Hz, 1H), 4.35 (d, J=18.6 Hz, 1H), 4.04 (d, J=18.6 Hz, 1H), 3.76 (s, 6H), 3.56 (br. s., 2H), 1.45-1.91 (m, 7H), 0.76-1.30 (m, 6H).

Example 17

6-[(S)-3-Cyclohexyl-2-(5,8-dimethoxy-3-oxo-3,9-dihydro-1H-chromeno[2,3-c]pyrrol-2-yl)-propionylamino]-nicotinic acid methyl ester

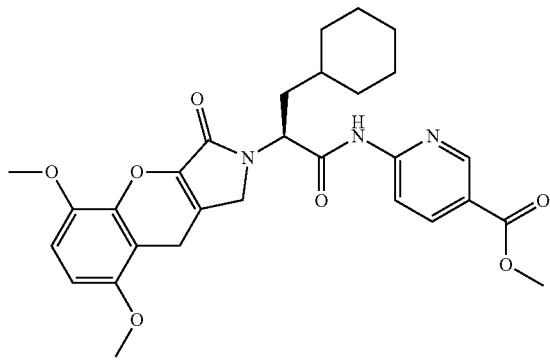

A solution of (S)-2-(5,8-dimethoxy-3-oxo-3,9-dihydro-1H-chromeno[2,3-c]pyrrol-2-yl)-4-methyl-pentanoic acid (Example 13, step 2c) (100 mg, 0.21 mmol), commercially available 6-aminonicotinic acid methyl ester (45 mg, 0.30 mmol), N-ethyl-N-dimethyaminopropyl carbodiimide hydrochloride (EDCI. HCl) (52 mg, 0.27 mmol), and N-hydroxybenzotriazole (HOBt) (37 mg, 0.27 mmol) in methylene chloride (10 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded 6-[(S)-3-cyclohexyl-2-(5,8-dimethoxy-3-oxo-3,9-dihydro-1H-chromeno[2,3-c]pyrrol-2-yl)-propionylamino]-nicotinic acid methyl ester (41 mg, 30.8%), as a white solid. $^1$H NMR (DMSO-$d_6$) δ: 11.31 (s, 1H), 8.87 (br. s., 1H), 8.28 (d, J=8.3 Hz, 1H), 8.14 (d, J=8.8 Hz, 1H), 6.91 (d, J=8.8 Hz, 1H), 6.67 (d, J=9.3 Hz, 1H), 5.10 (d, J=5.4 Hz, 1H), 4.38 (d, J=18.6 Hz, 1H), 4.03 (d, J=19.1 Hz, 1H), 3.86 (s, 3H), 3.76 (s, 6H), 3.55 (br. s., 2H), 1.41-1.90 (m, 7H), 0.78-1.31 (m, 6H).

Example 18

(S)-2-(5,8-Dimethoxy-3-oxo-3,9-dihydro-1H-chromeno[2,3-c]pyrrol-2-yl)-4-methyl-pentanoic acid pyridin-2-ylamide

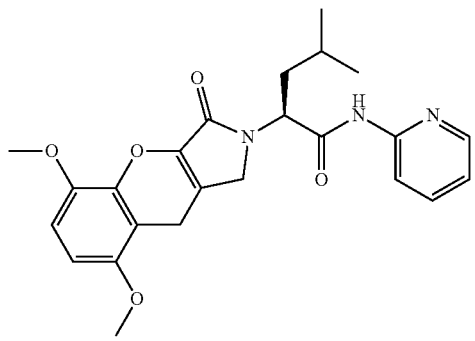

A solution of (S)-2-(5,8-dimethoxy-3-oxo-3,9-dihydro-1H-chromeno[2,3-c]pyrrol-2-yl)-4-methyl-pentanoic acid (Example 13, step 2c) (100 mg, 0.24 mmol), in tetrahydrofuran (10 mL) was treated with N-methylmorpholine (760 g, 0.69 mmol), 2-(1H-7-azabenzotriazol-1-yl)-1,1,3,3-tetramethyl uronium hexafluorophosphate (HATU) (263 mg, 0.69 mmol) and commercially available 2-aminopyridine (32 mg, 0.33 mmol). The mixture was heated in a sealed tube was heated for 16 hours at 90° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded (S)-2-(5,8-dimethoxy-3-oxo-3,9-dihydro-1H-chromeno[2,3-c]pyrrol-2-yl)-4-methyl-pentanoic acid (5-chloro-pyridin-2-yl)-amide (40 mg, 33.1%), as a white solid. $^1$H NMR (DMSO-$d_6$) δ: 10.78-10.92 (m, 1H), 8.34 (br. s., 1H), 8.00 (d, J=7.3 Hz, 1H), 7.77 (br. s., 1H), 7.12 (br. s., 1H), 6.91 (d, J=8.3 Hz, 1H), 6.66 (d, J=8.8 Hz, 1H), 5.08 (br. s., 1H), 4.39 (d, J=18.6 Hz, 1H), 4.02 (d, J=18.6 Hz, 1H), 3.76 (br. s., 6H), 3.55 (br. s., 2H), 1.82 (br. s., 1H), 1.61-1.74 (m, 1H), 1.46 (br. s., 1H), 0.86-1.01 (m, 6H).

Example 19

6-[(S)-2-(5,8-Dimethoxy-3-oxo-3,9-dihydro-1H-chromeno[2,3-c]pyrrol-2-yl)-4-methyl-pentanoylamino]-nicotinic acid methyl ester

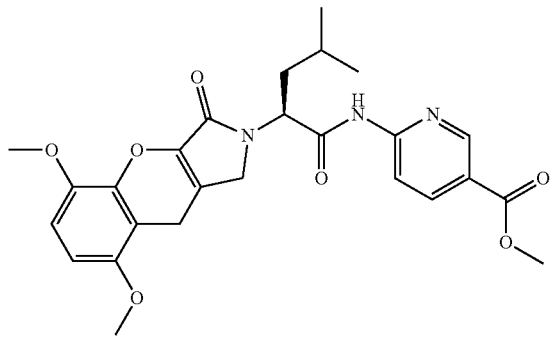

A solution of (S)-2-(5,8-dimethoxy-3-oxo-3,9-dihydro-1H-chromeno[2,3-c]pyrrol-2-yl)-4-methyl-pentanoic acid (Example 13, step 2c) (200 mg, 0.55 mmol), commercially available 6-aminonicotinic acid methyl ester (116 mg, 0.66 mmol), N-ethyl-N-dimethyaminopropyl carbodiimide hydrochloride (EDCI. HCl) (116 mg, 0.60 mmol), and N-hydroxybenzotriazole (HOBt) (82 mg, 0.60 mmol) in methylene chloride (10 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded 6-[(S)-2-(5,8-dimethoxy-3-oxo-3,9-dihydro-1H-chromeno[2,3-c]pyrrol-2-yl)-4-methyl-pentanoylamino]-nicotinic acid methyl ester (41 mg, 30.8%), as a white solid. $^1$H NMR (DMSO-$d_6$) δ: 11.35 (s, 1H), 8.88 (br. s., 1H), 8.28 (d, J=6.8 Hz, 1H), 8.15 (d, J=8.8 Hz, 1H), 6.91 (d, J=8.8 Hz, 1H), 6.66 (d, J=8.8 Hz, 1H), 5.09 (d, J=5.9 Hz, 1H), 4.41 (s, 1H), 4.36 (br. s., 1H), 4.04 (d, J=18.6 Hz, 1H), 3.86 (s, 3H), 3.76 (s, 6H), 3.55 (br. s., 2H), 1.76-1.94 (m, 1H), 1.61-1.74 (m, 1H), 1.46 (br. s., 1H), 0.93 (t, J=5.9 Hz, 6H).

Example 20

(S)-2-(5-Chloro-3-oxo-3,9-dihydro-1H-chromeno[2,3-c]pyrrol-2-yl)-3-cyclohexyl-N-pyridin-2-yl-propionamide

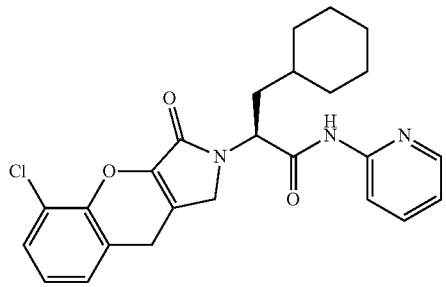

Step 1

(E)-4-Oxo-but-2-enoic acid ethyl ester (2.7 mL, 22.99 mmol), 2-nitro benzoic acid (0.648 g, 3.83 mmol), and pyrrolidine (0.31 mL, 3.83 mmol) were added simultaneously to a solution of commercially available 3-chloro-2-hydroxybenzaldehyde (5.0 g, 19.16 mmol) in dimethysulfoxide (20 mL) at 25° C. and the solution was stirred for 78 hours at 25° C. The reaction was quenched by the addition of water. The reaction mixture was then partitioned between water and ethyl acetate. The combined organics were washed with a saturated brine solution, dried over anhydrous sodium sulfate, filtered, rinsed and concentrated in vacuo. The residue obtained was purified on a silica gel Flash column chromatography using ethyl acetate-hexanes (1:1.2) as eluents, yielded 5-chloro-3-formyl-2H-chromene-2-carboxylic acid ethyl ester as a solid (2.10 g, 50.1%).

Step 2 a) To a solution of 5-chloro-3-formyl-2H-chromene-2-carboxylic acid ethyl ester (1.0 g, 3.74 mmol) in methanol (20 mL) containing molecular sieves (0.7 g) was added commercially available (S)-2-amino-3-cyclohexyl-propionic acid methyl ester (0.83 g, 3.74 mmol) and N,N'-diisopropylethylamine (1.30 mL, 7.49 mmol). The mixture was stirred at 25° C. for 10 hours. At this time, sodium cyanoborohydride (0.47 g, 7.49 mmol) and acetic acid (0.47 mL, 7.49 mmol) were added simultaneously to the reaction mixture, and the reaction mixture was stirred for additional 16 hours at 25° C. The reaction mixture was then filtered through celite and washed with methanol. The filtrate was concentrated in vacuo. Flash column chromatography (eluant-ethyl acetate:petroleum ether 1:19, $R_f$=0.6) over neutral alumina afforded 5-chloro-3-[((S)-2-cyclohexyl-1-methoxycarbonyl-ethylamino)-methyl]-4H-chromene-2 carboxylic acid methyl ester (0.75 g, 46.6%) as an oil.

A solution of 5-chloro-3-[((S)-2-cyclohexyl-1-methoxycarbonyl-ethylamino)-methyl]-2H-chromene-2-carboxylic acid ethyl ester (0.55 g, 1.26 mmol) and N,N'-diisopropylethyl amine (0.87 mL, 5.05 mmol) in acetonitrile (2 mL) was heated in a sealed tube at 140° C. for 48 hours. The reaction mixture, after aqueous work-up, was extracted with ethyl acetate (3×). The combined ethyl acetate layer was washed with brine, and dried over anhydrous sodium sulfate. The organic layer was concentrated in vacuo and the residue was purified over neutral alumina using hexanes-ethyl acetate (1:1.2) as eluents to afford (S)-2-(8-chloro-3-oxo-3,3a-dihydro-1H-chromeno[2,3-c]pyrrol-2-yl)-3-cyclohexyl-propionic acid methyl ester (0.24 g, 48.8%) as a off white solid.

c) A solution of (S)-2-(5-chloro-3-oxo-3,3a-dihydro-1H-chromeno[2,3-c]pyrrol-2-yl)-3-cyclohexyl-propionic acid methyl ester (1.5 g, 4.0 mmol) and lithium hydroxide monohydrate (0.22 g, 5.22 mmol) was stirred at 25° C. for 2 hours in tetrahydrofuran-water (3:1) mixture (50 mL). The reaction mixture was concentrated in vacuo to remove tetrahydrofuran, and the residue was acidified with 2N-hydrochloric acid, and diluted with water. The resulting solution was extracted with ethyl acetate (3×). The combined organic layer was washed with brine and dried over anhydrous sodium sulfate. The solvent was removed in vacuo to afford (S)-2-(5-chloro-3-oxo-3,9-dihydro-1H-chromeno[2,3-c]pyrrol-2-yl)-3-cyclohexyl-propionic acid (1.2 g, 83.3%) as off white solid.

Step 3

A solution of (S)-2-(5-chloro-3-oxo-3,9-dihydro-1H-chromeno[2,3-c]pyrrol-2-yl)-3-cyclohexyl-propionic acid (100 mg, 0.27 mmol), commercially available 2-aminopyridine (30 mg, 0.31 mmol), N-ethyl-N-dimethyaminopropyl carbodiimide hydrochloride (EDCI. HCl) (40 mg, 0.29 mmol), and N-hydroxybenzotriazole (HOBt) (56 mg, 0.29 mmol) in methylene chloride (5 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradiant elution, afforded (S)-2-(5-chloro-3-oxo-3,9-dihydro-1H-chromeno[2,3-c]pyrrol-2-yl)-3-cyclohexyl-N-pyridin-2-ylpropionamide (36 mg, 30%), as a white solid. $^1$H NMR (DMSO-$d_6$) δ: 10.86 (br. s., 1H), 8.34 (d, J=3.4 Hz, 1H), 8.00 (d, J=8.3 Hz, 1H), 7.77 (t, J=7.6 Hz, 1H), 7.40 (d, J=7.8 Hz, 1H), 7.23 (d, J=7.3 Hz, 1H), 7.05-7.16 (m, 2H), 5.10 (d, J=6.8 Hz, 1H), 4.43 (d, J=19.1 Hz, 1H), 4.06 (d, J=19.1 Hz, 1H), 3.83 (br. s., 2H), 1.51-1.87 (m, 7H), 0.75-1.30 (m, 6H).

Example 21

(S)-2-(5-Chloro-3-oxo-3,9-dihydro-1H-chromeno[2,3-c]pyrrol-2-yl)-3-cyclohexyl-N-thiazol-2-yl-propionamide

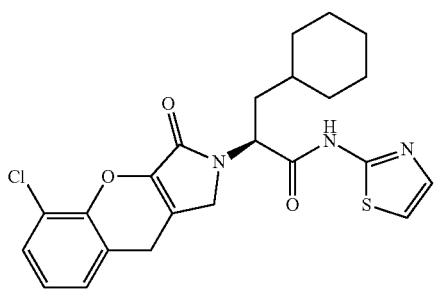

A solution of (S)-2-(5-chloro-3-oxo-3,9-dihydro-1H-chromeno[2,3-c]pyrrol-2-yl)-3-cyclohexyl-propionic acid (100 mg, 0.27 mmol) (Example 20, Step 2c), commercially available 2-aminothiazole (32 mg, 0.32 mmol), N-ethyl-N-dimethyaminopropyl carbodiimide hydrochloride (EDCI.HCl) (40 mg, 0.29 mmol), and N-hydroxybenzotriazole (HOBt) (56 mg, 0.29 mmol) in methylene chloride (5 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradiant elution, afforded (S)-2-(5-chloro-3-oxo-3,9-dihydro-1H-chromeno[2,3-c]pyrrol-2-yl)-3-cyclohexyl-N-thiazol-2-yl-propionamide (104 mg, 85.2%), as a white solid. $^1$H NMR (DMSO-$d_6$) δ: 12.55 (s, 1H), 7.50 (d, J=2.9 Hz, 1H), 7.40 (d, J=7.8 Hz, 1H), 7.20-7.28 (m, 2H), 7.07-7.17 (m, 1H), 5.07 (dd, J=10.5, 4.2 Hz, 1H), 4.39 (d, J=19.1 Hz, 1H), 4.08 (d, J=18.6 Hz, 1H), 3.84 (br. s., 2H), 1.52-1.90 (m, 7H), 0.76-1.29 (m, 6H).

Example 22

6-[(S)-2-(5-Chloro-3-oxo-3,9-dihydro-1H-chromeno[2,3-c]pyrrol-2-yl)-4-methyl-pentanoylamino]-nicotinic acid methyl ester

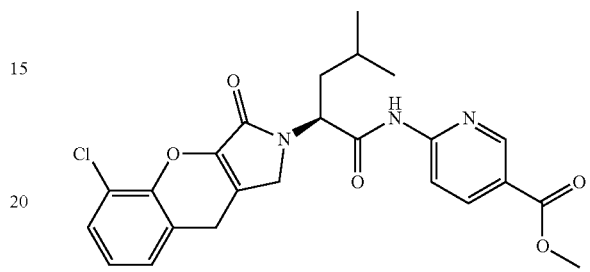

Step 1 a) To a solution of 5-chloro-3-formyl-2H-chromene-2-carboxylic acid ethyl ester (1.0 g, 3.74 mmol) (Example 20, Step 1) in methanol (20 mL) containing molecular sieves (0.7 g) was added commercially available (S)-2-amino-4-methyl-pentanoic acid methyl ester (0.68 g, 3.74 mmol) and N,N'-diisopropylethylamine (1.30 mL, 7.49 mmol). The mixture was stirred at 25° C. for 10 hours. At this time, sodium cyanoborohydride (0.47 g, 7.49 mmol) and acetic acid (0.43 mL, 7.20 mmol) were added simultaneously to the reaction mixture, and the reaction mixture was stirred for additional 16 hours at 25° C. The reaction mixture was then filtered through celite and washed with methanol. The filtrate was concentrated in vacuo. Flash column chromatography (eluant-ethyl acetate:petroleum ether 1:9, $R_f$=0.6) over neutral alumina afforded 5-chloro-3-[((S)-1-methoxycarbonyl-3-methyl-butylamino)-methyl]-4H-chromene-2 carboxylic acid methyl ester (0.46 g, 31%) as an oil.

b) A solution of 5-chloro-3-[((S)-1-methoxycarbonyl-3-methyl-butylamino)-methyl]-4H-chromene-2 carboxylic acid methyl ester (0.45 g, 1.13 mmol) and N,N'-diisopropylethyl amine (0.78 mL, 5.05 mmol) in acetonitrile (2 mL) was heated in a sealed tube at 140° C. for 48 hours. The reaction mixture, after aqueous work-up, extracted with ethyl acetate (3×). The combined ethyl acetate layer was washed with brine, and dried over anhydrous sodium sulfate. The organic layer was concentrated in vacuo and the residue was purified over neutral alumina using hexanes-ethyl acetate (1:1.2) as eluents to afford (S)-2-(5-chloro-3-oxo-3,9-dihydro-1H-chromeno[2,3-c]pyrrol-2-yl)-4-methyl-pentanoic acid methyl ester (0.225 g, 56.8%) as a red gum.

c) A solution of (S)-2-(5-chloro-3-oxo-3,9-dihydro-1H-chromeno[2,3-c]pyrrol-2-yl)-4-methyl-pentanoic acid methyl ester (2 g, 5.71 mmol) and lithium hydroxide monohydrate (0.312 g, 7.40 mmol) was stirred at 25° C. for 2 hours in tetrahydrofuran-water (3:1) mixture (50 mL). The reaction mixture was concentrated in vacuo to remove tetrahydrofuran, and the residue was acidified with 2N hydrochloric acid, and diluted with water. The resulting solution was extracted with ethyl acetate (3×). The combined organic layer was washed with brine and dried over anhydrous sodium sulfate. The solvent was removed in vacuo to afford (S)-2-(5-chloro- 3-oxo-3,9-dihydro-1H-chromeno[2,3-c]pyrrol-2-yl)-4-methyl-pentanoic acid (1.73 g, 93.6%) as white solid.

Step 2

A solution of (S)-2-(5-chloro-3-oxo-3,9-dihydro-1H-chromeno[2,3-c]pyrrol-2-yl)-4-methyl-pentanoic acid (100 mg, 0.27 mmol), commercially available 6-aminonicotinic acid methylester (109 mg, 0.71 mmol), N-ethyl-N-dimethyaminopropyl carbodiimide hydrochloride (EDCI. HCl) (125 mg, 0.66 mmol), and N-hydroxybenzotriazole (HOBt) (88 mg, 0.66 mmol) in methylene chloride (5 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded 6-[(S)-2-(5-chloro-3-oxo-3,9-dihydro-1H-chromeno[2,3-c]pyrrol-2-yl)-4-methyl-pentanoyl-amino]-nicotinic acid methyl ester (42 mg, 15%), as a white solid. $^1$H NMR (DMSO-d$_6$) δ: 11.35 (s, 1H), 8.88 (s, 1H), 8.29 (d, J=8.8 Hz, 1H), 8.15 (d, J=8.8 Hz, 1H), 7.40 (d, J=7.8 Hz, 1H), 7.23 (d, J=7.3 Hz, 1H), 7.08-7.16 (m, 1H), 5.10 (d, J=7.3 Hz, 1H), 4.42 (d, J=19.1 Hz, 1H), 4.07 (d, J=18.6 Hz, 1H), 3.86 (s, 3H), 3.83 (br. s., 2H), 1.76-2.02 (m, 1H), 1.69 (t, J=9.3 Hz, 1H), 1.48 (br. s., 1H), 0.87-0.99 (m, 6H).

Example 23

(S)-2-(5-Chloro-3-oxo-3,9-dihydro-1H-chromeno[2,3-c]pyrrol-2-yl)-4-methyl-pentanoic acid pyridin-2-ylamide

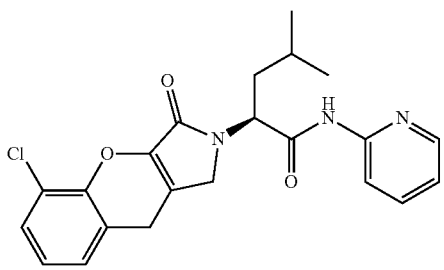

A solution of (S)-2-(5-chloro-3-oxo-3,9-dihydro-1H-chromeno[2,3-c]pyrrol-2-yl)-4-methyl-pentanoic acid (100 mg, 0.27 mmol) (Example 22, Step 1c), commercially available 2-aminopyridine (33 mg, 0.36 mmol), N-ethyl-N-dimethyaminopropyl carbodiimide hydrochloride (EDCI. HCl) (63 mg, 0.32 mmol), and N-hydroxybenzotriazole (HOBt) (44 mg, 0.32 mmol) in methylene chloride (1 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded (S)-2-(5-chloro-3-oxo-3,9-dihydro-1H-chromeno[2,3-c]pyrrol-2-yl)-4-methyl-pentanoic acid pyridin-2-ylamide (55 mg, 45%), as a white solid. $^1$H NMR (DMSO-d$_6$) δ: 10.88 (s, 1H), 8.34 (d, J=3.4 Hz, 1H), 8.01 (d, J=7.8 Hz, 1H), 7.77 (t, J=7.8 Hz, 1H), 7.40 (d, J=7.8 Hz, 1H), 7.23 (d, J=7.8 Hz, 1H), 7.13 (d, J=7.8 Hz, 2H), 5.08 (d, J=6.8 Hz, 1H), 4.43 (d, J=18.6 Hz, 1H), 4.06 (d, J=19.1 Hz, 1H), 3.82 (br. s., 2H), 1.78-1.94 (m, 1H), 1.61-1.74 (m, 1H), 1.47 (br. s., 1H), 0.94 (t, J=4.9 Hz, 6H).

Example 24

(S)-2-(5-Chloro-3-oxo-3,9-dihydro-1H-chromeno[2,3-c]pyrrol-2-yl)-4-methyl-pentanoic acid thiazol-2-ylamide

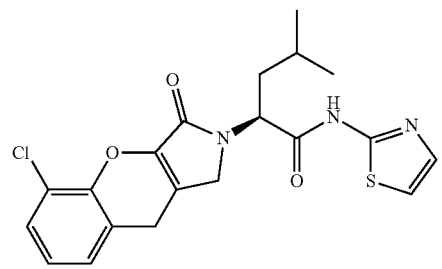

A solution of (S)-2-(5-chloro-3-oxo-3,9-dihydro-1H-chromeno[2,3-c]pyrrol-2-yl)-4-methyl-pentanoic acid (130 mg, 0.35 mmol) (Example 22, Step 1c), commercially available 2-aminothiazole (47 mg, 0.36 mmol), N-ethyl-N-dimethyaminopropyl carbodiimide hydrochloride (EDCI. HCl) (82 mg, 0.43 mmol), and N-hydroxybenzotriazole (HOBt) (57 mg, 0.43 mmol) in methylene chloride (15 mL) was stirred for 16 hours at 25° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded (S)-2-(5-chloro-3-oxo-3,9-dihydro-1H-chromeno[2,3-c]pyrrol-2-yl)-4-methyl-pentanoic acid thiazol-2-ylamide (145 mg, 58.2%), as a white solid. $^1$H NMR (DMSO-d$_6$) δ: 12.57 (s, 1H), 7.50 (d, J=3.4 Hz, 1H), 7.40 (d, J=7.8 Hz, 1H), 7.20-7.29 (m, 2H), 7.08-7.16 (m, 1H), 5.05 (dd, J=10.8, 4.4 Hz, 1H), 4.39 (d, J=19.1 Hz, 1H), 4.09 (d, J=19.1 Hz, 1H), 3.75-3.91 (m, 2H), 1.80-1.93 (m, 1H), 1.62-1.75 (m, 1H), 1.46 (br. s., 1H), 0.94 (t, J=6.6 Hz, 6H).

Example 25

(S)-3-Cyclohexyl-N-[1-((R)-2,3-dihydroxy-propyl)-1H-pyrazol-3-yl]-2-(8-methoxy-3-oxo-3,9-dihydro-1H-chromeno[2,3-c]pyrrol-2-yl)-propionamide

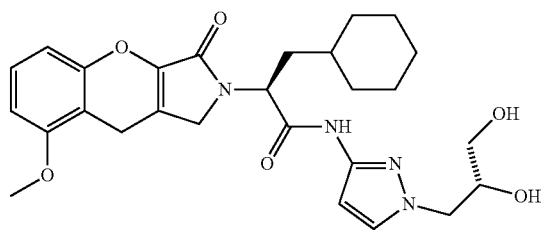

Step 1

A solution of (S)-2-(8-methoxy-3-oxo-3,9-dihydro-1H-chromeno[2,3-c]pyrrol-2-yl)-3-cyclohexyl-propionic acid (Example 7, step 2) (150 mg, 0.40 mmol), in tetrahydrofuran (5 mL) was treated with commercially available N-methyl-morpholine (0.11 mL, 1.01 mmol), 2-(1H-7-azabenzotriazol- 1-yl)-1,1,3,3-tetramethyl uronium hexafluorophosphate (HATU) (384 mg, 1.01 mmol) and 1-((R)-2,3-diethoxy-propyl)-1H-pyrazol-3-ylamine (96 mg, 0.48 mmol) (prepared following the procedure described in WO2009127546). The mixture was heated in a sealed tube was heated for 24 hours at 90° C. The reaction mixture was diluted with water and extracted with ethyl acetate (3×). The combined organic layers were dried over anhydrous sodium sulfate and concentrated in vacuo. The resulting residue, upon silica gel flash chromatography using hexane-ethyl acetate gradient elution, afforded (S)-3-cyclohexyl-N-[1-((R)-2,2-dimethyl-[1,3]dioxolan-4-ylmethyl)-1H-pyrazol-3-yl]-2-(8-methoxy-3-oxo-3,9-dihydro-1H-chromeno[2,3-c]pyrrol-2-yl)-propionamide (145 mg, 65.3%), as a white solid.

Step 2

A solution of (S)-3-cyclohexyl-N-[1-((R)-2,2-dimethyl-[1,3]dioxolan-4-ylmethyl)-1H-pyrazol-3-yl]-2-(8-methoxy-3-oxo-3,9-dihydro-1H-chromeno[2,3-c]pyrrol-2-yl)-propionamide (140 mg, 0.25 mmol) in tetrahydrofuran (5 mL) was treated with 2N HCl (2.05 mL, 0.31 mmol). The mixture was stirred for 4 hours at 23° C. The reaction mixture after aqueous work-up and silica gel flash chromatography using hexane-ethyl acetate gradient elution, afforded (S)-3-cyclohexyl-N-[1-((R)-2,3-dihydroxy-propyl)-1H-pyrazol-3-yl]-2-(8-methoxy-3-oxo-3,9-dihydro-1H-chromeno[2,3-c]pyrrol-2-yl)-propionamide (68.1 mg, 52.7%), as a white solid. $^1$H NMR (DMSO-$d_6$) δ: 10.80 (s, 1H), 7.52 (s, 1H), 7.22 (t, J=8.3 Hz, 1H), 6.76 (d, J=8.3 Hz, 1H), 6.68 (d, J=8.3 Hz, 1H), 6.39 (s, 1H), 4.93 (d, J=4.9 Hz, 2H), 4.70 (br. s., 1H), 4.37 (d, J=19.1 Hz, 1H), 4.09 (dd, J=13.4, 4.2 Hz, 1H), 3.99 (d, J=19.1 Hz, 2H), 3.88 (d, J=7.8 Hz, 1H), 3.83-3.86 (m, 1H), 3.76 (br. s., 2H), 3.53 (s, 3H), 1.50-1.83 (m, 7H), 0.81-1.31 (m, 6H).

Example 26

(S)-3-Cyclopentyl-N-[1-(2-hydroxy-2-methyl-propyl)-1H-pyrazol-3-yl]-2-(3-oxo-3,9-dihydro-1H-chromeno[2,3-c]pyrrol-2-yl)-propionamide

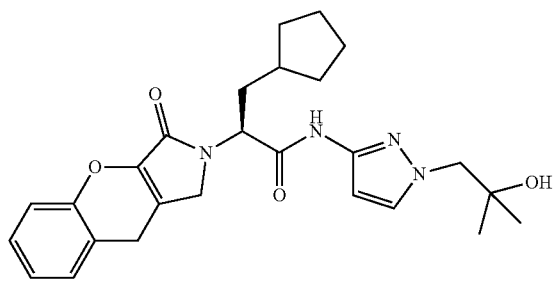

Step 1

To a stirred mixture of commercially available (S)-(−)-α̃αDiphenyl-2-pyrrolidinemethanol (0.83 g, 3.28 mmol) in toluene (40 mL) was added 2-nitrobenzoic acid (0.55 g, 3.28 mmol), commercially available 2-Hydroxybenzaldehyde (2.00 g, 16.38 mmol) and (E)-4-oxo-but-2-enoic acid ethyl ester (2.51 g, 19.65 mmol). After addition was complete the mixture was stirred at room temperature for 3 days. Upon completion of the reaction the toluene was removed by vacuum distillation. The residue was diluted with ethyl acetate and washed with water, a saturated sodium bicarbonate solution and a saturated sodium chloride solution. The organic fraction was then dried over magnesium sulfate. The crude product obtained was purified by ISCO flash chromatography (Teledyne Isco RediSep Flash Column 40 g; (0% to 100% ethyl acetate/hexane) to afford 3-formyl-2H-chromene-2-carboxylic acid ethyl ester as a yellow oil, 1.09 g (29% yield). (Ref: Chem. Eur. Journal; 2007, 13, pg 574).

Step 2

To an ice-cooled mixture of 3-formyl-2H-chromene-2-carboxylic acid ethyl ester (1.86 g, 8.02 mmol) in THF (10 mL) under nitrogen atmosphere was added commercially available BH$_3$-THF solution (8.0 mL of a 1M soln, 8.0 mmol). The mixture was stirred at 0° C. for 1 hour. Upon completion of the reaction, the mixture was quenched by the slow addition of a 1N HCl solution. The aqueous layer was extracted with three portions of ethyl acetate. The combined organic fractions were washed with a saturated sodium chloride solution and then dried over magnesium sulfate. The crude product obtained, 3-hydroxymethyl-2H-chromene-2-carboxylic acid ethyl ester, as a yellow oil, 1.73 g (92% yield) was used without further purification.

Step 3

To an ice-cooled mixture of 3-Hydroxymethyl-2H-chromene-2-carboxylic acid ethyl ester (1.73 g, 7.39 mmol) in methylene chloride (25 mL) was added commercially available carbon tetrabromide (2.70 g, 8.13 mmol) and commercially available triphenylphosphine (1.94 g, 7.39 mmol). After addition was complete the mixture was stirred at 0° C. for 6 hours. Upon completion of the reaction, the methylene chloride was removed under reduced pressure. The crude product obtained was purified by ISCO flash chromatography (Teledyne Isco RediSep Flash Column 40 g; (0% to 90% ethyl acetate/hexane) to afford 3-bromomethyl-2H-chromene-2-carboxylic acid ethyl ester as a yellow oil, 1.08 g (49% yield).

Step 4

To a stirred mixture of commercially available β-cyclopentyl-L-alanine methyl ester hydrochloride (0.83 g, 4.01 mmol) dissolved in acetonitrile (20 mL) under a nitrogen atmosphere was added N,N'-diisopropylethylamine (0.70 g, 4.10 mmol). After addition was complete, the mixture was stirred at 60° C. for 1 hour. The reaction was cooled to 25° C. and treated with N,N'-diisopropylethylamine (0.70 g, 4.10 mmol) and heated to 80° C. at which time 3-Bromomethyl-2H-chromene-2-carboxylic acid ethyl ester (1.08 g, 3.65 mmol) in acetonitrile (10 mL) was added slowly. After the addition was complete the reaction mixture was heated to 105° C. and stirred for 18 hours. The reaction mixture was cooled to 25° C. and concentrated. The residue was diluted with methylene chloride and washed with 2N HCl and a saturated sodium chloride solution and dried over magnesium sulfate. The crude product obtained was purified by ISCO flash chromatography (Teledyne Isco RediSep Flash Column 40 g; (0% to 100% ethyl acetate/hexane) to afford, (S)-3-Cyclopentyl-2-(3-oxo-3,3a-dihydro-1H-chromeno[2,3-c]pyrrol-2-yl)-propionic acid methyl ester as a heavy yellow oil, 0.64 g (52% yield).

Step 5

To a magnetically stirred mixture of (S)-3-Cyclopentyl-2-(3-oxo-3,3a-dihydro-1H-chromeno[2,3-c]pyrrol-2-yl)-propionic acid methyl ester (0.64 g, 1.88 mmol) in THF (9 mL) and water (3 mL) was added lithium hydroxide (0.102 g, 2.44 mmol). After addition was complete the mixture was stirred at 25° C. for 2 hours. The reaction mixture was poured into water and ether and the layers separated. The aqueous layer was made acidic with 2N HCl and extracted with three portions of ethyl acetate. The combined ethyl acetate fractions were washed with a saturated sodium chloride solution, dried over magnesium sulfate, filtered and concentrated to afford (S)-3-Cyclopentyl-2-(3-oxo-3,9-dihydro-1H-chromeno[2,3-c]pyrrol-2-yl)-propionic acid as a white solid, 500 mg (81% yield). ESI-LRMS m/e calcd for $C_{19}H_{21}NO_4$ [M$^+$] 327, found 328 [M+H⁺]. (Note: The double bond isomerizes during the course of the reaction based on NMR spectrum)

Step 6

A solution of (S)-3-Cyclopentyl-2-(3-oxo-3,9-dihydro-1H-chromeno[2,3-c]pyrrol-2-yl)-propionic acid (200 mg, 0.61 mmol) in methylene chloride (10 mL) was treated with 1-(3-dimethylaminopropyl)-3-ethylcarbodiimide hydrochloride (EDCI-HCl) (130 mg, 0.67 mmol), 1-hydroxybenzotriazole (HOBT) (90 mg, 0.67 mmol) and commercially available 1-(3-amino-pyrazol-1-yl)-2-methyl-propan-2-ol (114 mg, 0.73 mmol). The reaction mixture was stirred for 18 hours at 25° C., under $N_2$. The reaction mixture was diluted with methylene chloride, washed with 2N HCl, saturated sodium bicarbonate solution, and a saturated sodium chloride solution and dried over magnesium sulfate. The crude product obtained after concentration was purified by ISCO flash chromatography (Teledyne Isco RediSep Flash Column 12 g; (0% to 100% ethyl acetate/hexane) to afford (S)-3-Cyclopentyl-N-[1-(2-hydroxy-2-methyl-propyl)-1H-pyrazol-3-yl]-2-(3-oxo-3,9-dihydro-1H-chromeno[2,3-c]pyrrol-2-yl)-propionamide as a white powder, 205 mg (72% yield). $^1$H NMR (300 MHz, DMSO-$d_6$) δ ppm 1.04 (br. s., 3 H), 1.06 (br. s., 3 H), 1.09-1.83 (m, 10 H), 1.83-1.97 (m, 1 H), 3.75 (s, 2 H), 3.89 (s, 2 H), 4.03 (d, J=19.2 Hz, 1 H), 4.40 (d, J=19.2 Hz, 1 H), 4.67 (s, 1 H), 4.87 (dd, J=10.3, 4.8 Hz, 1 H), 6.44 (d, J=1.8 Hz, 1 H), 7.03-7.15 (m, 2 H), 7.20-7.28 (m, 2 H), 7.53 (d, J=1.8 Hz, 1 H), 10.86 (s, 1 H).

Example 27

In Vitro Glucokinase Activity

The compounds of formula I which include the compounds set forth in the Examples activated glucokinase in vitro by the procedure of this Example. In this manner, they increase the flux of glucose metabolism which causes increased insulin secretion. Therefore, the compounds of formula I are glucokinase activators useful for increasing insulin secretion.

Glucokinase In Vitro Assay Protocol: Glucokinase (GK) was assayed by coupling the production of glucose-6-phosphate to the generation of NADH with glucose-6-phosphate dehydrogenase (G6PDH, 0.75-1 kunits/mg; Boehringer Mannheim, Indianapolis, Ind.) from *Leuconostoc mesenteroides* as the coupling enzyme:

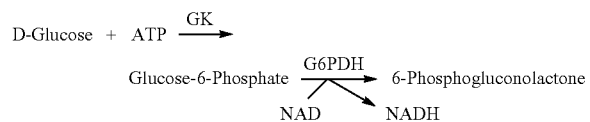

Recombinant human liver GK1 was expressed in *E. coli* as a glutathione S-transferase fusion protein (GST-GK) [Liang et al, 1995]and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 30° C. in a flat bottom 96-well tissue culture plate from Costar (Cambridge, Mass.) with a final incubation volume of 120 μL. The incubation reaction contained the following: 25 mM Hepes buffer (pH 7.1), 25 mM KCl, 5 mM D-glucose, 1 mM ATP, 1.8 mM NAD, 2 mM $MgCl_2$, 1 μM sorbitol-6-phosphate, 1 mM dithiothreitol, test drug or 10% DMSO, ~7 units/ml G6PDH, and GK (see below). All organic reagents were >98% pure and were from Boehringer Mannheim with the exceptions of D-glucose and Hepes which were from Sigma Chemical Co, St Louis, Mo. Test compounds were dissolved in DMSO and were added to the incubation reaction minus GST-GK in a volume of 12 μL to yield a final DMSO concentration of 10%. This mix was pre-incubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 μL GST-GK.

After addition of enzyme, the increase in optical density (OD) at 340 nm was monitored spectrophotometrically to determine the rate of change ($OD_{340}$ per min). The GK activity ($OD_{340}$/min) in control wells (10% DMSO minus GK activators) was compared with the activity in wells containing test GK activators, and the concentration of activator that produced a 50% increase in the activity of GK, i.e., the $SC_{1.5:0.1}$, was calculated. The table below provides the in vitro glucokinase activity for the compounds in the Examples:

| Example | SC 1.5:0.1 |
|---------|------------|
| 1 | 1.311 |
| 2 | 4.051 |
| 3 | 4.602 |
| 4 | 3.18 |
| 5 | 9.277 |
| 6 | 3.324 |
| 7 | 0.333 |
| 8 | 0.292 |
| 9 | 0.746 |
| 10 | 0.302 |
| 11 | 8.123 |
| 12 | 0.906 |
| 13 | 0.304 |
| 14 | 0.911 |
| 15 | 0.428 |
| 16 | 2.439 |
| 17 | 0.219 |
| 18 | 2.532 |
| 19 | 0.803 |
| 20 | 2.423 |
| 21 | 4.181 |
| 22 | 9.858 |
| 23 | 11.865 |
| 24 | 18.957 |
| 25 | 0.507 |
| 26 | 1.181 |

It is to be understood that the invention is not limited to the particular embodiments of the invention described above, as variations of the particular embodiments may be made and still fall within the scope of the appended claims.

What is claimed is:

1. A compound according to formula I,

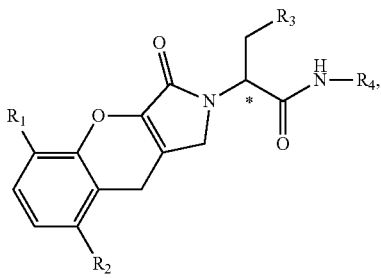

wherein:
$R_1$ and $R_2$ are each independently selected from the group consisting of H, Cl, Br, F and $OCH_3$;
$R_3$ is selected from the group consisting of lower alkyl, cycloalkyl, and heterocycloalkyl; and
$R_4$ is an unsubstituted or substituted heteroaryl connected by a ring carbon atom to the adjacent amine group, with at least one heteroatom being nitrogen which is adjacent to the connecting ring carbon atom, said substituted heteroaryl being substituted at a position other than adjacent to said connecting carbon atom independently with halogen, lower alkyl, ester, cyano, acid, cycloalkyl, aryl, —$CH_2$-aryl, heterocycloalkyl or —$CH_2$-heterocycloalkyl;

or a pharmaceutically acceptable salt thereof.

2. A compound according to claim 1 wherein $R_1$ and $R_2$ are each independently selected from the group consisting of H, Cl, and $OCH_3$.

3. A compound according to claim 1 wherein $R_1$ is H.

4. A compound according to claim 1 wherein $R_1$ is Cl.

5. A compound according to claim 1 wherein $R_1$ is $OCH_3$.

6. A compound according to claim 1 wherein $R_2$ is H.

7. A compound according to claim 1 wherein $R_2$ is Cl.

8. A compound according to claim 1 wherein $R_2$ is $OCH_3$.

9. A compound according to claim 1 wherein $R_3$ is lower alkyl or lower cycloalkyl.

10. A compound according to claim 1 wherein $R_3$ is cyclohexyl or cyclopentyl.

11. A compound according to claim 1 wherein $R_3$ is 2-propyl or cyclohexyl.

12. A compound according to claim 1 wherein $R_3$ is cyclopentyl.

13. A compound according to claim 1 wherein $R_4$ is an unsubstituted or substituted heteroaryl selected from the group consisting of pyridinyl, thioazolyl, and pyrrolyl, said substituted heteroaryl being substituted at a position other than adjacent to said connecting carbon atom independently with halogen, lower alkyl, ester, cyano, acid, cycloalkyl, aryl, —$CH_2$-aryl, heterocycloalkyl or —$CH_2$-heterocycloalkyl.

14. A compound according to claim 1 wherein $R_4$ is an unsubstituted or substituted heteroaryl which is pyridinyl or thioazolyl, said substituted heteroaryl being substituted at a position other than adjacent to said connecting carbon atom independently with chloro or methyl ester.

15. A compound according to claim 1 wherein $R_4$ is pyrazolyl substituted at a position other than adjacent to said connection carbon atom with lower alkyl, said lower alkyl being substituted once or twice by hydroxyl.

16. A compound according to claim 1 wherein:
$R_1$ and $R_2$ are each independently selected from the group consisting of H, Cl, and $OCH_3$;
$R_3$ is lower alkyl or lower cycloalkyl; and
$R_4$ is an unsubstituted or substituted heteroaryl connected by a ring carbon atom to the adjacent amine group, with at least one heteroatom being nitrogen which is adjacent to the connecting ring carbon atom, said substituted heteroaryl being substituted at a position other than adjacent to said connecting carbon atom independently with halogen, lower alkyl, ester, cyano, acid, cycloalkyl, aryl, —$CH_2$-aryl, heterocycloalkyl or —$CH_2$-heterocycloalkyl;

or a pharmaceutically acceptable salt thereof.

17. A compound according to claim 1 wherein:
$R_1$ and $R_2$ are each independently selected from the group consisting of H, Cl, and $OCH_3$;
$R_3$ is selected from the group consisting of: 2-propyl, cyclohexyl, and cyclopentyl; and
$R_4$ is an unsubstituted or substituted heteroaryl selected from the group consisting of pyridinyl, thioazolyl, and pyrazolyl, said substituted heteroaryl being substituted at a position other than adjacent to said connecting carbon atom independently with halogen, ester, or lower alkyl;

or a pharmaceutically acceptable salt thereof.

18. A compound according to claim 1 wherein:
$R_1$ and $R_2$ are each independently selected from the group consisting of H, Cl, and $OCH_3$;
$R_3$ is 2-propyl or lower cycloalkyl; and
$R_4$ is an unsubstituted or substituted pyridinyl or pyrazolyl;

or a pharmaceutically acceptable salt thereof.

19. A compound according to claim 1 selected from the group consisting of:
(S)-2-(8-Chloro-3-oxo-3,9-dihydro-1H-chromeno[2,3-c]pyrrol-2-yl)-3-cyclohexyl-N-pyridin-2-yl-propionamide;
(S)-2-(8-Chloro-3-oxo-3,9-dihydro-1H-chromeno[2,3-c]pyrrol-2-yl)-3-cyclohexyl-N-thiazol-2-yl-propionamide;
(S)-2-(8-Chloro-3-oxo-3,9-dihydro-1H-chromeno[2,3-c]pyrrol-2-yl)-4-methyl-pentanoic acid pyridin-2-ylamide;
(S)-2-(8-Chloro-3-oxo-3,9-dihydro-1H-chromeno[2,3-c]pyrrol-2-yl)-4-methyl-pentanoic acid (5-chloro-pyridin-2-yl)-amide;
(S)-2-(8-Chloro-3-oxo-3,9-dihydro-1H-chromeno[2,3-c]pyrrol-2-yl)-4-methyl-pentanoic acid thiazol-2-ylamide;
6-[(S)-2-(8-Chloro-3-oxo-3,9-dihydro-1H-chromeno[2,3-c]pyrrol-2-yl)-4-methyl-pentanoylamino]-nicotinic acid methyl ester;
(S)-3-Cyclohexyl-2-(8-methoxy-3-oxo-3,9-dihydro-1H-chromeno[2,3-c]pyrrol-2-yl)-N-pyridin-2-yl-propionamide;
(S)—N-(5-Chloro-pyridin-2-yl)-3-cyclohexyl-2-(8-methoxy-3-oxo-3,9-dihydro-1H-chromeno[2,3-c]pyrrol-2-yl)-propionamide;
(S)-3-Cyclohexyl-2-(8-methoxy-3-oxo-3,9-dihydro-1H-chromeno[2,3-c]pyrrol-2-yl)-N-thiazol-2-yl-propionamide;
6-[(S)-3-Cyclohexyl-2-(8-methoxy-3-oxo-3,9-dihydro-1H-chromeno[2,3-c]pyrrol-2-yl)-propionylamino]-nicotinic acid methyl ester;
(S)-2-(8-Methoxy-3-oxo-3,9-dihydro-1H-chromeno[2,3-c]pyrrol-2-yl)-4-methyl-pentanoic acid thiazol-2-ylamide;

6-[(S)-2-(8-Methoxy-3-oxo-3,9-dihydro-1H-chromeno[2,3-c]pyrrol-2-yl)-4-methyl-pentanoylamino]-nicotinic acid methyl ester;

(S)-3-Cyclohexyl-2-(5,8-dimethoxy-3-oxo-3,9-dihydro-1H-chromeno[2,3-c]pyrrol-2-yl)-N-pyridin-2-yl-propionamide;

(S)—N-(5-Chloro-pyridin-2-yl)-3-cyclohexyl-2-(5,8-dimethoxy-3-oxo-3,9-dihydro-1H-chromeno[2,3-c]pyrrol-2-yl)-propionamide;

(S)-3-Cyclohexyl-2-(5,8-dimethoxy-3-oxo-3,9-dihydro-1H-chromeno[2,3-c]pyrrol-2-yl)-N-thiazol-2-yl-propionamide;

6-[(S)-3-Cyclohexyl-2-(5,8-dimethoxy-3-oxo-3,9-dihydro-1H-chromeno[2,3-c]pyrrol-2-yl)-propionylamino]-nicotinic acid methyl ester;

(S)-2-(5,8-Dimethoxy-3-oxo-3,9-dihydro-1H-chromeno[2,3-c]pyrrol-2-yl)-4-methyl-pentanoic acid (5-chloro-pyridin-2-yl)-amide;

(S)-2-(5,8-Dimethoxy-3-oxo-3,9-dihydro-1H-chromeno[2,3-c]pyrrol-2-yl)-4-methyl-pentanoic acid pyridin-2-ylamide;

6-[(S)-2-(5,8-Dimethoxy-3-oxo-3,9-dihydro-1H-chromeno[2,3-c]pyrrol-2-yl)-4-methyl-pentanoylamino]-nicotinic acid methyl ester;

(S)-2-(5-Chloro-3-oxo-3,9-dihydro-1H-chromeno[2,3-c]pyrrol-2-yl)-3-cyclohexyl-N-pyridin-2-yl-propionamide;

(S)-2-(5-Chloro-3-oxo-3,9-dihydro-1H-chromeno[2,3-c]pyrrol-2-yl)-3-cyclohexyl-N-thiazol-2-yl-propionamide;

6-[(S)-2-(5-Chloro-3-oxo-3,9-dihydro-1H-chromeno[2,3-c]pyrrol-2-yl)-4-methyl-pentanoylamino]-nicotinic acid methyl ester;

(S)-2-(5-Chloro-3-oxo-3,9-dihydro-1H-chromeno[2,3-c]pyrrol-2-yl)-4-methyl-pentanoic acid pyridin-2-ylamide;

(S)-2-(5-Chloro-3-oxo-3,9-dihydro-1H-chromeno[2,3-c]pyrrol-2-yl)-4-methyl-pentanoic acid thiazol-2-ylamide;

(S)-3-Cyclohexyl-N-[1-((R)-2,3-dihydroxy-propyl)-1H-pyrazol-3-yl]-2-(8-methoxy-3-oxo-3,9-dihydro-1H-chromeno[2,3-c]pyrrol-2-yl)-propionamide; and (S)-3-Cyclopentyl-N-[1-(2-hydroxy-2-methyl-propyl)-1H-pyrazol-3-yl]-2-(3-oxo-3,9-dihydro-1H-chromeno[2,3-c]pyrrol-2-yl)-propionamide.

20. A composition comprising a compound according to claim 1 and a pharmaceutically acceptable carrier.

* * * * *

UNITED STATES PATENT AND TRADEMARK OFFICE
CERTIFICATE OF CORRECTION

PATENT NO.        : 8,178,689 B2
APPLICATION NO.   : 13/156394
DATED             : May 15, 2012
INVENTOR(S)       : Ramakanth Sarabu It is certified that error appears in the above-identified patent and that said Letters Patent is hereby corrected as shown below:

TITLE PAGE:

Assignee information reads: "(73) Assignee Hoffman-La Roche Inc., Nutley, NJ (US)". The Assignee information should read -- (73) Assignee Hoffmann-La Roche Inc., Nutley, NJ --.

Signed and Sealed this
Tenth Day of July, 2012

David J. Kappos
*Director of the United States Patent and Trademark Office*